United States Patent
Kesteleyn et al.

(10) Patent No.: US 11,491,148 B2
(45) Date of Patent: Nov. 8, 2022

(54) AMIDE DERIVATIVES USEFUL IN THE TREATMENT OF HBV INFECTION OR HBV-INDUCED DISEASES

(71) Applicant: Janssen Sciences Ireland Unlimited Company, County Cork (IE)

(72) Inventors: Bart Rudolf Romanie Kesteleyn, Berlare (BE); Jan Martin Berke, Düsseldorf (DE); Erwin Coesemans, Nijlen (BE); Sandrine Céline Grosse, Turnhout (BE); Edgar Jacoby, Vosselaar (BE); Tim Hugo Maria Jonckers, Heist-op-den-Berg (BE); Stefaan Julien Last, Beveren (BE); Wim Gaston Verschueren, Berchem (BE); Michel Obringer, Achen (FR); Christelle Catherine Cecile Doebelin, Illkirch (FR)

(73) Assignee: Janssen Sciences Ireland Unlimited Company, Ringaskiddy (IE)

( * ) Notice: Subject to any disclaimer, the term of this patent is extended or adjusted under 35 U.S.C. 154(b) by 1 day.

(21) Appl. No.: 16/867,249

(22) Filed: May 5, 2020

(65) Prior Publication Data

US 2020/0352925 A1    Nov. 12, 2020

(30) Foreign Application Priority Data

May 6, 2019 (EP) .................................... 19172736

(51) Int. Cl.

| | |
|---|---|
| *C07D 403/12* | (2006.01) |
| *A61K 31/4439* | (2006.01) |
| *A61P 31/20* | (2006.01) |
| *A61K 31/4192* | (2006.01) |
| *A61K 45/06* | (2006.01) |
| *C07D 403/14* | (2006.01) |

(52) U.S. Cl.
CPC ...... *A61K 31/4439* (2013.01); *A61K 31/4192* (2013.01); *A61K 45/06* (2013.01); *A61P 31/20* (2018.01); *C07D 403/12* (2013.01); *C07D 403/14* (2013.01)

(58) Field of Classification Search
CPC .................................................. C07D 403/12
See application file for complete search history.

(56) References Cited

U.S. PATENT DOCUMENTS

| | | |
|---|---|---|
| 3,843,662 A | 10/1974 | Holland |
| 4,569,940 A | 2/1986 | Watts |
| 4,962,101 A | 10/1990 | DiNinno et al. |
| 4,995,898 A | 2/1991 | Nasu et al. |
| 5,272,167 A | 12/1993 | Girijavallabhan et al. |
| 5,308,826 A | 5/1994 | Chin et al. |
| 5,314,880 A | 5/1994 | Whittaker et al. |
| 5,571,821 A | 11/1996 | Chan et al. |
| 5,585,327 A | 12/1996 | Chin et al. |
| 5,607,929 A | 3/1997 | Nicol et al. |
| 5,708,034 A | 1/1998 | Kleemann et al. |
| 5,723,411 A | 3/1998 | Stevenson |
| 5,756,524 A | 5/1998 | Riordan et al. |
| 5,795,907 A | 8/1998 | Kalindjian et al. |
| 5,912,260 A | 6/1999 | Kalindjian et al. |
| 5,919,970 A | 7/1999 | Song et al. |
| 5,939,423 A | 8/1999 | Karlin et al. |
| 6,025,367 A | 2/2000 | Forbes et al. |
| 6,143,776 A | 11/2000 | Erlanson |
| 6,265,408 B1 | 7/2001 | Forbes et al. |
| 6,476,025 B1 | 11/2002 | Gutterer |
| 6,650,463 B2 | 11/2003 | Obikawa et al. |
| 6,668,527 B2 | 12/2003 | Duplantier et al. |
| 6,780,389 B2 | 8/2004 | Karl et al. |
| 7,115,595 B2 | 10/2006 | Sunagawa et al. |
| 7,186,735 B2 | 3/2007 | Strobel et al. |
| 7,338,956 B2 | 3/2008 | Strobel et al. |
| 7,368,457 B2 | 5/2008 | Josien |
| 7,384,967 B2 | 6/2008 | Polisetti et al. |
| 7,541,373 B2 | 6/2009 | Polisetti et al. |

(Continued)

FOREIGN PATENT DOCUMENTS

| | | |
|---|---|---|
| CA | 2950807 A1 | 12/2013 |
| CN | 101039919 A | 9/2007 |

(Continued)

OTHER PUBLICATIONS

Berke, et al., "Capsid Assembly Modulators Have a Dual Mechanism of Action in Primary Human Hepatocytes Infected with Hepatitis B Virus", Antimicrobial Agents and Chemotherapy, vol. 61(8); pp. 1-14 (e00560-17) (Aug. 2017).

(Continued)

*Primary Examiner* — Brian E Mcdowell

(74) *Attorney, Agent, or Firm* — Ice Miller LLP

(57) ABSTRACT

The application relates to amide derivatives of formula (I), processes for their preparation, pharmaceutical compositions, and their uses, more particularly their uses in treating chronic hepatitis B virus (HBV) infection:

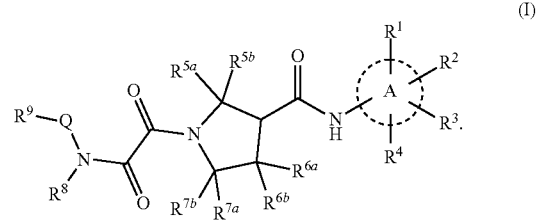

(I)

19 Claims, No Drawings

(56) References Cited

U.S. PATENT DOCUMENTS

| | | |
|---|---|---|
| 7,544,700 B2 | 6/2009 | Halazy et al. |
| 7,576,688 B2 | 8/2009 | Lehtinen |
| 7,595,322 B2 | 9/2009 | Morgan et al. |
| 7,608,723 B2 | 10/2009 | Boyce et al. |
| 7,750,158 B2 | 7/2010 | Shankar et al. |
| 7,786,104 B2 | 8/2010 | DuBois et al. |
| 7,790,726 B2 | 9/2010 | Zhang et al. |
| 7,838,525 B2 | 11/2010 | Jones et al. |
| 7,888,373 B2 | 2/2011 | Morgan et al. |
| 7,994,168 B2 | 8/2011 | Lennig et al. |
| 8,071,779 B2 | 12/2011 | Lampe et al. |
| 8,084,457 B2 | 12/2011 | Choidas et al. |
| 8,097,728 B2 | 1/2012 | Gu et al. |
| 8,101,620 B2 | 1/2012 | Morgan et al. |
| 8,153,650 B2 | 4/2012 | Dubois et al. |
| 8,153,803 B2 | 4/2012 | Kazantsev |
| 8,207,195 B2 | 6/2012 | Navratil et al. |
| 8,227,489 B2 | 7/2012 | Dubois et al. |
| 8,273,754 B2 | 9/2012 | Ali et al. |
| 8,299,096 B2 | 10/2012 | Navratil et al. |
| 8,299,114 B2 | 10/2012 | Dubois et al. |
| 8,354,425 B2 | 1/2013 | Dubois et al. |
| 8,394,820 B2 | 3/2013 | Dubois et al. |
| 8,399,491 B2 | 3/2013 | Dubois et al. |
| 8,404,747 B2 | 3/2013 | Kazantsev et al. |
| 8,410,141 B2 | 4/2013 | Murata et al. |
| 8,410,147 B2 | 4/2013 | Peterson et al. |
| 8,536,168 B2 | 9/2013 | Dai et al. |
| 8,609,668 B2 | 12/2013 | Cuconati et al. |
| 8,629,274 B2 | 1/2014 | Hartman et al. |
| 8,722,742 B2 | 5/2014 | Reyes |
| 8,808,702 B2 | 8/2014 | Reddy et al. |
| 8,889,716 B2 | 11/2014 | Prime et al. |
| 8,993,771 B2 | 3/2015 | Hartman |
| 9,051,296 B2 | 6/2015 | Yamagishi et al. |
| 9,061,008 B2 | 6/2015 | Hartman et al. |
| 9,066,932 B2 | 6/2015 | Hartman et al. |
| 9,115,101 B2 | 8/2015 | Bodil van Niel et al. |
| RE45,670 E | 9/2015 | Polisetti et al. |
| 9,156,839 B2 | 10/2015 | Vandyck et al. |
| 9,169,212 B2 | 10/2015 | Hartman et al. |
| 9,181,288 B2 | 11/2015 | Hartman et al. |
| 9,205,079 B2 | 12/2015 | Hartman |
| 9,339,510 B2 | 5/2016 | Hartman et al. |
| 9,400,280 B2 | 7/2016 | Hartman |
| 9,458,176 B2 | 10/2016 | Takaishi et al. |
| 9,505,722 B2 | 11/2016 | Hartman et al. |
| 9,567,299 B2 | 2/2017 | Vandyck et al. |
| 9,579,313 B2 | 2/2017 | Hartman |
| 9,676,747 B2 | 6/2017 | Hartman et al. |
| 9,884,818 B2 | 2/2018 | Vandyck et al. |
| 10,071,961 B2 | 9/2018 | Vandyck et al. |
| 10,125,094 B2 | 11/2018 | Vandyck |
| 10,160,743 B2 | 12/2018 | Vandyck et al. |
| 10,441,589 B2 | 10/2019 | Hartman et al. |
| 10,457,638 B2 | 10/2019 | Vandyck et al. |
| 10,676,429 B2 | 6/2020 | Vandyck et al. |
| 10,941,113 B2 | 3/2021 | Vandyck et al. |
| 2002/0049236 A1 | 4/2002 | Duplantier et al. |
| 2003/0114443 A1 | 6/2003 | Imamura et al. |
| 2004/0039009 A1 | 2/2004 | Jagtap et al. |
| 2004/0110802 A1 | 6/2004 | Thorarensen et al. |
| 2005/0009871 A1 | 1/2005 | Ramesh et al. |
| 2005/0054850 A1 | 3/2005 | Wu et al. |
| 2005/0129833 A1 | 6/2005 | Kincaid et al. |
| 2005/0148632 A1 | 7/2005 | Tokumasu et al. |
| 2005/0221272 A1 | 10/2005 | Housman et al. |
| 2005/0239833 A1 | 10/2005 | Kazantsev et al. |
| 2006/0040984 A1 | 2/2006 | Luckhurst et al. |
| 2006/0100228 A1 | 5/2006 | Shankar et al. |
| 2006/0100257 A1 | 5/2006 | Muto et al. |
| 2006/0122236 A1 | 6/2006 | Wood et al. |
| 2007/0142440 A1 | 6/2007 | Burgdorf et al. |
| 2007/0161578 A1 | 7/2007 | Hwa et al. |
| 2009/0018118 A1 | 1/2009 | Urleb et al. |
| 2009/0036420 A1 | 2/2009 | Galley et al. |
| 2009/0105218 A1 | 4/2009 | Ulven et al. |
| 2009/0163545 A1 | 6/2009 | Goldfarb |
| 2009/0259044 A1 | 10/2009 | Kazantsev |
| 2009/0325959 A1 | 12/2009 | Vittitow et al. |
| 2009/0325960 A1 | 12/2009 | Fulcher et al. |
| 2010/0008968 A1 | 1/2010 | Lampe et al. |
| 2010/0016310 A1 | 1/2010 | Ingraham |
| 2010/0022517 A1 | 1/2010 | Richards et al. |
| 2010/0087415 A1 | 4/2010 | Whitten et al. |
| 2010/0113421 A1 | 5/2010 | Williams et al. |
| 2010/0204210 A1 | 8/2010 | Sorensen |
| 2011/0009622 A1 | 1/2011 | Makoto et al. |
| 2011/0064695 A1 | 3/2011 | Qiu et al. |
| 2011/0064696 A1 | 3/2011 | Or et al. |
| 2011/0065686 A1 | 3/2011 | Mazola Reyes et al. |
| 2011/0184019 A1 | 7/2011 | Zitzmann et al. |
| 2011/0189771 A1 | 8/2011 | Block et al. |
| 2011/0275630 A1 | 11/2011 | Matulenko et al. |
| 2011/0301158 A1 | 12/2011 | Polisetti et al. |
| 2013/0005756 A1 | 1/2013 | Navratil et al. |
| 2013/0131059 A1 | 5/2013 | Lampe et al. |
| 2013/0131106 A1 | 5/2013 | Lampe et al. |
| 2013/0142827 A1 | 6/2013 | Block et al. |
| 2013/0203733 A1 | 8/2013 | Kazantsev et al. |
| 2013/0251673 A1 | 9/2013 | Hartman et al. |
| 2013/0267517 A1 | 10/2013 | Guo et al. |
| 2013/0303552 A1 | 11/2013 | Xu et al. |
| 2014/0178337 A1 | 6/2014 | Hartman et al. |
| 2014/0179665 A1 | 6/2014 | Hartman et al. |
| 2014/0275167 A1 | 9/2014 | Hartman |
| 2015/0152073 A1 | 6/2015 | Hartman et al. |
| 2015/0174115 A1 | 6/2015 | Hartman |
| 2015/0175602 A1 | 6/2015 | Brown et al. |
| 2015/0197493 A1 | 7/2015 | Hartman |
| 2015/0197533 A1 | 7/2015 | Hartman et al. |
| 2015/0216938 A1 | 8/2015 | Hartman |
| 2015/0225355 A1 | 8/2015 | Hartman |
| 2015/0252057 A1 | 9/2015 | Guo et al. |
| 2015/0259324 A1 | 9/2015 | Hartman et al. |
| 2015/0266890 A1 | 9/2015 | Vandyck et al. |
| 2015/0274652 A1 | 10/2015 | Hartman |
| 2015/0274653 A1 | 10/2015 | Vandyck et al. |
| 2016/0000812 A1 | 1/2016 | Hartman et al. |
| 2016/0002155 A1 | 1/2016 | Vandyck et al. |
| 2016/0051512 A1 | 2/2016 | Vandyck et al. |
| 2016/0083383 A1 | 3/2016 | Guo et al. |
| 2016/0115125 A1 | 4/2016 | Vandyck et al. |
| 2016/0115149 A1 | 4/2016 | Vandyck et al. |
| 2016/0158214 A1 | 6/2016 | Hartman |
| 2016/0176817 A1 | 6/2016 | Vandyck et al. |
| 2016/0272599 A1 | 9/2016 | Hartman et al. |
| 2016/0347741 A1 | 12/2016 | Vandyck et al. |
| 2017/0002025 A1 | 1/2017 | Vendeville et al. |
| 2017/0015629 A1 | 1/2017 | Hartman et al. |
| 2017/0114018 A1 | 4/2017 | Hartman |
| 2017/0158634 A1 | 6/2017 | Vandyck et al. |
| 2017/0182021 A1 | 6/2017 | Hartman |
| 2017/0334882 A1 | 11/2017 | Hartman et al. |
| 2018/0127361 A1 | 5/2018 | Vandyck et al. |
| 2019/0282542 A1 | 9/2019 | Vandyck et al. |
| 2020/0039931 A1 | 2/2020 | Vandyck et al. |
| 2021/0024462 A1 | 1/2021 | Vandyck et al. |

FOREIGN PATENT DOCUMENTS

| | | |
|---|---|---|
| CN | 102093320 A | 6/2011 |
| CN | 102206172 A | 10/2011 |
| EP | 0232067 A2 | 8/1987 |
| EP | 0742200 A1 | 11/1996 |
| EP | 2280001 A4 | 1/2012 |
| JP | 62142164 | 6/1987 |
| JP | 2008179621 A | 7/2008 |
| JP | 2008525406 A | 7/2008 |
| JP | 2010535172 A | 11/2010 |
| WO | 198403281 A1 | 8/1984 |
| WO | 1992/07835 A1 | 5/1992 |
| WO | 1998023285 A1 | 6/1998 |
| WO | 1999/09022 A1 | 2/1999 |

(56) References Cited

FOREIGN PATENT DOCUMENTS

| | | |
|---|---|---|
| WO | 1999038845 A1 | 8/1999 |
| WO | 199948492 A1 | 9/1999 |
| WO | 199965906 A1 | 12/1999 |
| WO | 200105390 A2 | 1/2001 |
| WO | 200119788 A2 | 3/2001 |
| WO | 2001051487 A1 | 7/2001 |
| WO | 200155121 A1 | 8/2001 |
| WO | 200185694 A2 | 11/2001 |
| WO | 2002051410 | 7/2002 |
| WO | 2002064618 A2 | 8/2002 |
| WO | 2003/002518 A1 | 1/2003 |
| WO | 2003007955 A2 | 1/2003 |
| WO | 2003044016 A1 | 5/2003 |
| WO | 2003101961 A1 | 12/2003 |
| WO | 2004010943 A2 | 2/2004 |
| WO | 2004011427 A2 | 2/2004 |
| WO | 2004022060 A2 | 3/2004 |
| WO | 2004058709 A2 | 7/2004 |
| WO | 2004086865 A1 | 10/2004 |
| WO | 2004099192 A2 | 11/2004 |
| WO | 2004100947 A2 | 11/2004 |
| WO | 2005016922 A1 | 2/2005 |
| WO | 2005000231 A3 | 5/2005 |
| WO | 2005044797 A1 | 5/2005 |
| WO | 2005087217 A1 | 9/2005 |
| WO | 2005105785 A2 | 11/2005 |
| WO | 2005115374 A1 | 12/2005 |
| WO | 2006002133 A1 | 1/2006 |
| WO | 2006012642 A2 | 2/2006 |
| WO | 2006024834 A1 | 3/2006 |
| WO | 2006/053109 A1 | 5/2006 |
| WO | 2006067445 A2 | 6/2006 |
| WO | 2006067446 A1 | 6/2006 |
| WO | 2006123257 A2 | 11/2006 |
| WO | 2006128129 A2 | 11/2006 |
| WO | 2006128172 A2 | 11/2006 |
| WO | 2007031791 A1 | 3/2007 |
| WO | 2007070556 A2 | 6/2007 |
| WO | 2008011476 A2 | 1/2008 |
| WO | 2008022171 A1 | 2/2008 |
| WO | 2008054605 A3 | 7/2008 |
| WO | 2008093614 A1 | 8/2008 |
| WO | 2008137794 A1 | 11/2008 |
| WO | 2008154819 A1 | 12/2008 |
| WO | 2009/018219 A2 | 2/2009 |
| WO | 2009016088 A1 | 2/2009 |
| WO | 2009062402 A1 | 5/2009 |
| WO | 2009086303 A2 | 7/2009 |
| WO | 2009131065 A1 | 10/2009 |
| WO | 2009146013 A1 | 12/2009 |
| WO | 2010018113 A2 | 2/2010 |
| WO | 2010043592 A1 | 4/2010 |
| WO | 2010059658 A1 | 5/2010 |
| WO | 2010088000 A2 | 8/2010 |
| WO | 2010123139 A1 | 10/2010 |
| WO | 2010138758 A1 | 12/2010 |
| WO | 2011/003191 | 1/2011 |
| WO | 2011002635 A1 | 1/2011 |
| WO | 2011035143 A2 | 3/2011 |
| WO | 2011088015 A1 | 7/2011 |
| WO | 2011088561 A1 | 7/2011 |
| WO | 2011109237 A1 | 9/2011 |
| WO | 2011112191 A1 | 9/2011 |
| WO | 2011123609 A1 | 10/2011 |
| WO | 2011140324 A1 | 11/2011 |
| WO | 2011155898 A1 | 12/2011 |
| WO | 2012016133 A2 | 2/2012 |
| WO | 2012018635 A2 | 2/2012 |
| WO | 2012033956 A1 | 3/2012 |
| WO | 2012049277 A1 | 4/2012 |
| WO | 2012075235 A1 | 6/2012 |
| WO | 2012080050 A1 | 6/2012 |
| WO | 2012117216 A1 | 9/2012 |
| WO | 2012136834 A1 | 10/2012 |
| WO | 2013006394 A1 | 1/2013 |
| WO | 2013096744 A1 | 6/2013 |
| WO | 2013102655 A1 | 7/2013 |
| WO | 2013130703 A2 | 9/2013 |
| WO | 2013144129 A1 | 10/2013 |
| WO | 2013/174962 | 11/2013 |
| WO | 2013181584 A2 | 12/2013 |
| WO | 2013184757 A1 | 12/2013 |
| WO | 2014/033176 | 3/2014 |
| WO | 2014033167 A1 | 3/2014 |
| WO | 2014033170 A1 | 3/2014 |
| WO | 2014037480 A1 | 3/2014 |
| WO | 2014106019 A2 | 7/2014 |
| WO | 2014131847 A1 | 9/2014 |
| WO | 2014151958 A1 | 9/2014 |
| WO | 2014161888 A1 | 10/2014 |
| WO | 2014165128 A2 | 10/2014 |
| WO | 2014184328 A1 | 11/2014 |
| WO | 2014184350 A1 | 11/2014 |
| WO | 2014184365 A1 | 11/2014 |
| WO | 2014191301 A1 | 12/2014 |
| WO | 2014191726 A1 | 12/2014 |
| WO | 2014198880 A1 | 12/2014 |
| WO | 2015011281 A1 | 1/2015 |
| WO | 2015055764 A1 | 4/2015 |
| WO | 2015057945 A1 | 4/2015 |
| WO | 2015059212 A1 | 4/2015 |
| WO | 2015073774 A1 | 5/2015 |
| WO | 2015109130 A1 | 7/2015 |
| WO | 2015116923 A1 | 8/2015 |
| WO | 2015118057 A1 | 8/2015 |
| WO | 2015132276 A1 | 9/2015 |
| WO | 2015138895 A1 | 9/2015 |
| WO | 2015144093 A1 | 10/2015 |
| WO | 2015180631 A1 | 12/2015 |
| WO | 2016089990 A1 | 6/2016 |
| WO | 2016109663 A2 | 7/2016 |
| WO | 2016109684 A2 | 7/2016 |
| WO | 2016109689 A1 | 7/2016 |
| WO | 2016149581 A1 | 9/2016 |
| WO | 2016113273 A1 | 10/2016 |
| WO | 2016161268 A1 | 10/2016 |
| WO | 2016168619 A1 | 10/2016 |
| WO | 2016183266 A1 | 11/2016 |
| WO | 2017181141 A2 | 10/2017 |
| WO | 2019011323 A1 | 1/2019 |

OTHER PUBLICATIONS

Corcuera, et al., "Novel non-heteroarylpyrimidine (HAP) capsid assembly modifiers have a different mode of action from HAPs in vitro", Antiviral Research, vol. 158; pp. 135-142 (2018).

Diab, et al., "The diverse functions of the hepatitis B core/capsid protein (HBc) in the viral life cycle: Implications for the development of HBc-targeting antivirals", Antiviral Research, vol. 149; pp. 211-220 (2018).

Huber, et al., "Novel Hepatitis B Virus Capsid-Targeting Antiviral that Aggregates Core Particles and Inhibits Nuclear Entry of Viral Cores", ACS Infectious Diseases, DOI: 10.1021; pp. 1-30 (Dec. 24, 2018).

Hughes, et al., "Hepatitis Delta Virus", The Lancet, vol. 378: pp. 73-85, (Jul. 2, 2011).

Sun, et al., "Stable HepG2- and Huh7-based human hepatoma cell lines for efficient regulated expression of infectious hepatitis B virus", Journal of Hepatology, vol. 45: pp. 636-645 (2006).

International Search Report and Written Opinion for PCT Patent Application No. PCT/EP2020/062360, dated Jul. 9, 2020.

Online Registry via STN Dec. 22, 2008, RN 1088200-12-7.

Online Registry via STN, Mar. 2, 2007, RN 924514-21-6.

Online Registry via STN, Sep. 2, 2003, RN 577752-12-6.

Basarab et al., Design of Helicobacter pylori glutamate racemase inhibitors as selective antibacterial agents : a novel pro-drug approach to increase exposure, Bioorg. Med. Chem. Lett., vol. 18; pp. 4716-4722 (Aug. 15, 2008).

Bennes, et al., "Recognition-induced control and acceleration of a pyroole Diels-Alder reaction", Tetrahedron Letters, vol. 42 : pp. 2377-2380 (2001).

(56) References Cited

OTHER PUBLICATIONS

Berke, et al., "Capsid Assembly Modulator JNJ-56136379 Prevents de Novo Infection of Primary Human Hepatocytes with Hepatitis B Virus", Hepatology, Oct. 2016, pp. 124A, 234.

Brahmania, et al., "New Therapeutic Agents for Chronic Hepatitis B", Lancet Infec Dis, vol. 16: pp. e10-21 (Feb. 2016).

Brezillon, et al., "Antiviral Activity of Bay 41-4109 on Hepatitis B Virus in Humanized Alb-uPA/SCID Mice", PLos ONE, vol. 6 (12): pp. e25096 (1-6) (Dec. 2011).

Cai, et al., "Identification of disubstituted sulfonamide compounds as specific inhibitors of hepatitis B virus covalently closed circular DNA formation, Antimicrobial agents and chemotherapy", pp. vol 56(8): pp. 4277-4288 (May 29, 2012).

Campagna et al., "Sulfamoylbenzamide Derivatives Inhibit the Assembly of Hepatitis B Virus Nucleocapsids", Journal of Virology, ),vol. 87 (12): pp. 6931-6942 (Jun. 2013).

Campagna, "Sulfamoylbenzamide Derivatives are a Novel Class of Hepatities B Virus Inhibitors Targeting PGRNA Encapsidation", 2011 International Meeting on Molecular Biology of Hepatitis B Viruses, Poster Presentation, (Oct. 9-12, 2011).

Carver, et al., Polyfunctionalisation of Imidazole via Sequential Imidazolyl Anion Formation, Tetrahedron, 1997, pp. 14481-14496, vol. 53 Issue 42.

Chang, et al., "NMR-spectroscopy-based Metabonomic Approach to the Analysis of Bay41-4109, a novel anti-HBV Compound, induced Hepatotoxicity in Rats", Toxicology Letters, vol. 173: pp. 161-167 (2007).

CHEMDIV, Inc., 1H-Pyrazole-4-carboxamide, 1-ethyl-N-phenyl-3-(4-thiomorpholinylaulfonyl1)—(CA Index Name), CHEMCATS, Mar. 2, 2012, pp. 1-1, RN 1359596-55-6 Registry.

CHEMDIV, Inc., 1H-PyraZole-4-carboxamide, N-(4-fluoro-3-methylphenyl)-3-{ (hexahydro-1H-azepin-1-y1) sulfonyl1]-1-methyl—(CA Index Name), CHEMCATS, Mar. 2, 2012, pp. 1-1, RN 1359583-56-4 Registry.

Cho, et al., "2-Amino-N-(2,6-dichloropyridin-3-yl)acetamide derivatives as a novel class of HBV capsid assembly inhibitor", Journal of Viral Hepatitis, vol. 21: pp. 843-852 (2014).

Cowie, et al., "Mortality due to viral hepatitis in the Global Burden of Disease Study 2010: new evidence of an urgent global public health priority demanding action", Antiviral Therapy,vol. 18: pp. 953-954 (2013).

Cremlyn, R.J. et al, Chlorosulphonation of Thiophene and Furan-2-Carboxanilides, Journal of the Chemical Society of Pakistan, Sep. 30, 1986, 323-330, vol. 8, No. 3.

Delaney, et al., "Phenylpropenamide Derivatives AT-61 and AT-130 Inhibit Replication of Wild-Tpe and Lamivudine-Resistant Strains of Hepatitis B Virus in Vitro", Antimicrobial Agents and Chemotherapy, vol. 46(9): pp. 3057-3060 (Sep. 2002).

Deres, et al., "Inhibition of Hepatitis B Virus Replication by Drug-Induced Depletion of Nucleocpsids", Science, vol. 299: pp. 893-896 (Feb. 7, 2003).

Duan, et al., 2-Phenylquinazolin-4(3H)-one, a class of potent PDE5 Inhibitors with High Selectivity Versus PDE6, Bioorganic & Medicinal Chemistry Letter, vol. 19: pp. 2777-2779 (2009).

El-Sayed, et al, "A Comparative Study of the 1-9 Reactions of Thiophene-2-Carboxanilides and related Compounds", Chemistry of Heterocyclic Compounds, vol. 34 (7): pp. 796-801 (Jan. 1, 1998).(XP000881506).

El-Sharief, et al., "Synthesis of Different Types of Chlorinated Sulphonamides with Expected Insecticidal and Bactericidal Activities", Proceedings of the Indian National Science Academy, vol. 53(1): pp. 179-188 (1987).

Ermann, et al., "Arylsulfonamide CB2 Receptor Agonists: SAR and Optimization of CB2 Selectivity", Bioorganic & Medicinal Chemistry Letters, vol. 18: pp. 1725-1729 (2008).

Foley, "An Effecient Synthesis of 2-Chloro-3-carboethoxy or 2-Chloro-3-cyano- 4,5-disubstituted and 5-substituted Pyrroles", Tetrahedron Letters, vol. 35(33): pp. 5989-5992, (1994).

Gane, et al., "Phase 1a Safety and Pharmacokinetics of NVR3-778, a Potential First-in-class HBV Core Inhibitor", The Abstract of the Liver Meeting 2014 (AASLD), Abstract LB-19, Boston, MA (2014).

Gang Liu et al, discovery of Highly Potent and Selective Pan-Aurora Kinase Inhibitors with Enhanced in Vivo Antitumor Therapeutic Index, Journal of Medicinal chemistry, Mar. 1, 2012, pp. 3250-3260, vol. 55.

Geies, et al., Synthesis of some Thiazolo-[3,2-a]Pyrimidines, Phosphorus, Sulfur and Silicon, vol. 56: pp. 87-93 (1991).

Geng et al., "Small-Molecule Inhibitors for the Treatment of Hepatitis B Virus Documented in Patents", Mini-Reviews in Medicinal Chemistry, Apr. 1, 2013, pp. 749-776 (XP055105561-XP009176654), vol. 13.

Goodman, et al, "Discovery of potent, selective sulfonylfuran urea endothelial lipase inhibitors", Bioorganic & Medicinal Chemistry Letters, vol. 19:pp. 27-30 (2009).

Guo, et al., "HBc binds to the CpG island of HBV cccDNA and promotes an epigenetic permissive state", Epigenetics, vol. 6 (6): pp. 720-726 (Jun. 2011).

Hogan, et al., "Aqueous Process Chemistry: The Preparation of Aryl Sulfonyl Chlorides", Organic Process Research & Development, vol. 13: pp. 875-879 (2009).

Horig, et al., "From bench to Clinic and back : Perspective on the 1st IQPC translational Research conference", Journal of Translational Medicine, vol. 2(44): pp. 1-8 (Dec. 20, 2004).

Huang, et al., "Blockage of HBV Virus Replication and Inhibition of cccDNA Establishment by Core Protein Allosteric Modifiers (CpAMs)", Hepatology, vol. 64 (1 Suppl): pp. 937A-938A, ( Oct. 2016).

Jayathilaka, et al, "A chemical compound that stimulated the human homologous recombination protein RAD51", Proceedings of the National Academy of Sciences on the United States of America, vol. 105 (41): pp. 15848-15853 (Oct. 14, 2008).

Katen, et al., "Assembly-Directed Antivirals Differentially Bind Quasiequivalend Pockets to Modify Hepatitis B Virus Capsid Tertiary and Quaternary Structure", Structure, vol. 21: pp. 1406-1416 (Aug. 6, 2013).

Kim, et al, Discovery of novel HCV polymerase inhibitors using pharmacophore-based virtual screening, Bioorganic & Medicinal Chemistry Letters, Apr. 9, 2011, pp. 3329-3334, vol. 21.

Klumpp, et al., "High Antiviral Activity of the HBV Core Inhibitor NVR 3-778 in the Humanized UPA/SCID Mouse Model", Journal of Hepatology, vol. 62:p. S235 (2015).

Klumpp, et al., "High-resolution crystal structure of a hepatitis B virus replication inhibitor bound to the viral core protein", PNAS, vol. 112(49): pp. 15196-15201 (Dec. 8, 2015).

Lam, et al., "HBV Corre Assembly Modulators Block Antigen Prouction When Present During Infection, but not during Persistent Infection", The Abstracts of the Liver Meeting 2016 (AASLD), vol. 64 (1 Suppl.), Boston, MA (Oct. 2016).

Lam, et al., "Inhibition of Hepatitis B Virus Replication by the HBV Core Inhibitors NVR3-778", The Abstract of the Liver Meeting 2015 (AASLD), Abstract 33: p. 223A, San Francisco, CA (Oct. 2015).

Lam, et al., "Serum HBV RNA as a Pharmacodynamic (PD) Marker of HBV Treatment Response to Core Assembly Modulator NVR 3-778 and Pegylate-Interferon Alpha", Poster Presented in the AASLD/EASL—HBV Treatment Endpoints Workshop, Poster No. 3774, Alexandria, VA (Sep. 9, 2016).

Lambeng, et al, "Arylsulfonamides as a new class of cannabinoid CB1 receptor ligands:identification of a lead and initial SAR studies", Bioorganic & Medicinal Chemistry Letters, vol. 17(1) pp. 272-277 (Jan. 1, 2007).

Lau, et al., "Peginterferon Alfa-2a, Lamivudine, and the Combination for HBeAg-Positive Chronic Hepatitis B", New England Journal of Medicine, vol. 352(26): pp. 2682-2695 (Jun. 30, 2005).

Li Bing, et al., Progress in anti Hepatitus B Virus non-nucleosidicdrugs, J. Liaoning Medical University, vol. 30(1): pp. 88-91 (Dec. 31, 2009.

Liaw, et al., "Hepatitis B Virus Infection", Lancet, vol. 373: pp. 582-592 (Feb. 14, 2009).

(56) References Cited

OTHER PUBLICATIONS

Lucifora, et al., "Specific and Nonhepatotoxic Degradation of Nuclear Hepatitis B Virus cccDNA", Science, vol. 343: pp. 1221-1228 (Mar. 14, 2014).
Mabrouk, "Discovering best candidates for Hepatocellular Carcinoma (HCC) by in-silico techniques and tools", Int. J. Bioinformatics Research and Applications, vol. 8 (1/2): pp. 141-152 (Jan. 1, 2012).
Manzoor, et al., "Hepatitis B Virus Therapy: What's the future holding for us?", World Journal of Gastroenterology, vol. 21(44): pp. 12558-12575 (Nov. 28, 2015).
Marcellin, et al., "Peginterferon Alfa-2a Alone, Lamivudine Alone, and the Two in Combination in Patients with HBeAg-Negative Chronic Hepatitis B", The New England Journal of Medicine, vol. 351(12): pp. 1206-1217 (Sep. 16, 2014).
Mohamed, et al., "Synthesis of Different Types of Chlorinated Sulphonamides with Expected Insecticidal and Antimicrobial Activities", Acta Pharmaceutica Jugoslavica, vol. 36 (3): pp. 301-310, (1986).
Mohebbi, et al., "An Overview of Hepatitis B Virus Surface Antigen Secretion Inhibitors", Frontier in Microbiology, vol. 9: pp. 1-9 (Apr. 2018).
Moranta et al., "Synthesis and properties of 1-alkyl-2-methyl-3-sulfonylpyrroles and 1-alkyl-2-methyl-3-sulfonylpyrrole-5-carboxylic acid derivates", J. Chem. Soc. Perkin Trans., vol. 19: pp. 3285-3292 (1998).
Nijampatnam et al., "Recent advances in the development of HBV capsid assembly modulators", Current Opinion in Chemical Biology, vol. 50; pp. 73-79 (2019).
Online Registr via STN, Dec. 28, 2008, RN 1090750-88-1.
Online Registry via STN Dec. 21, 2011, RN 1351507-46-4.
Online Registry via STN , Aug. 13, 2012, RN 1390589-54-4.
Online Registry via STN Feb. 2, 2007, RN 919040-39-1.
Online Registry via STN Feb. 2, 2007, RN 919040-53-2.
Online Registry via STN Feb. 2, 2007, RN 919040-55-1.
Online Registry via STN Feb. 3, 2012, RN 1359583-56-1.
Online Registry via STN Feb. 3, 2012, RN 1359596_55_6.
Online Registry via STN Aug. 6, 2012. RN 1386725-02-5.
Online Registry via STN Jun. 7, 2012, RN 1375909-37-7.
Online Registry via STN Dec. 8, 2012, RN 1389720-57-3.
Online Registry via STN Aug. 24, 2019, RN 1275589-30-1.
Online Registry via STN Aug. 24, 2019, RN 311800-19-8.
Online Registry via STN Aug. 24, 2019, RN 312756-74-1.
Online Registry via STN Aug. 24, 2019, RN 312756-75-5.
Online Registry via STN Aug. 24, 2019, RN 313225_30_8.
Online Registry via STN Aug. 24, 2019, RN 313254-27-2.
Online Registry via STN Oct. 10, 1987, RN 110644-97-8.
Online Registry via STN Oct. 10, 2001, RN 361373-90-2.
Online Registry via STN Dec. 11, 2007, RN 957487-45-5.
Online Registry via STN Dec. 11, 2007, RN 957487-49-9.
Online Registry via STN Aug. 12, 2012, RN 1389686-79-6.
Online Registry via STN Aug. 13, 2012, RN 1390500-09-0.
Online Registry via STN Jan. 16, 2001, RN 314043-17-9.
Online Registry via STN Jul. 16, 1992, RN 142428-99-7.
Online Registry via STN Mar. 17, 2013, RN 1424462-66-7.
Online Registry via STN Mar. 18, 2010 , RN 1211415-65-4.
Online Registry via STN Sep. 18, 2012, RN 1394742-82-5.
Online Registry via STN Aug. 20, 2006, RN 902846-15-5.
Online Registry via STN 2010, RN 1253220-91-5.
Online Registry via STN Aug. 30, 2011, RN 1325664-90-1.
Online Registry via STN, Jan. 24, 2008, RN 296790-26-6.
Online Registry via STN, Feb. 2, 2007, RN 9019040-48-5.
Online Registry via STN, Feb. 2, 2007, RN 919040-37-2.
Online Registry via STN, May. 6, 2011, RN 1291044-81-9.
Online Registry via STN, Sep. 6, 2011, RN 1328738-57-3.
Online Registry via STN, Oct. 7, 2008, RN 1057788-44-9.
Online Registry via STN, Oct. 7, 2008, RN 1057871-39-2.
Online Registry via STN, Jan. 1, 2001, RN 313253-89-3.
Online Registry via STN, Mar. 10, 2010, RN 1208400-27-4.
Online Registry via STN, Feb. 15, 2007, RN 921179-95-5.
Online Registry via STN, Aug. 15, 2011, RN 1317923-24-2.
Online Registry via STN, Aug. 15, 2011, RN 1318022-74-0.
Online Registry via STN, Mar. 17, 2003, RN 499189-09-2.
Online Registry via STN, May 18, 2011, RN 1296380-95-4.
Online Registry via STN, Oct. 18, 2000, RN 296894-70-7.
Online Registry via STN, Sep. 20, 2013, RN 1452780-00-5.
Online Registry via STN, Apr. 24, 2002, RN 406926-60-1.
Online Registry via STN, Apr. 28, 2011, RN 1286906-97-5.
Online Registry via STN. Apr. 19, 2008, RN 930914-71-9.
Patani, et al., "Bioisoterism: A rational Approach in Drug Design", Chem. Rev., vol. 96: pp. 3147-3176 (1996).
Patel, et al., "Synthesis N-Ethylpiperazinyl Sulfonyl Group Incorporated Benzamides", Indian Journal of Heterocyclic Chemistry, vol. 15: pp. 201-202 (Oct.-Dec. 2005).
Pubchem., N-(4-Fluorophenyl)-4-(piperidin-1-yusulfonyl)thiophene-2-carboxamide, http://pubchem.ncbi.nlm.nih.gov, Aug. 26, 2021, pp. 1-11, PubChem CID 1252955.
Pubchem., qHTS Assay for Lipid Storage Modulators in *Drosophila* S3 Cells, http://pubchem.ncbi.nlm.nih.gov, Aug. 26, 2021, pp. 1-14, PubChem AID 2685.
Pubchem., {4-[(Cyclohexylamino) sulfonyl](2-thienyl)}-N-benzamide, http://pubchem.ncbi.nlm.nih.gov/compound/, Apr. 6, 2021, Equivalent to US 2015266890, 1217168.
Qidong You et al, Pharmaceutical Chemistry, Chemical Industry Press, Jan. 31, 2014, pp. 32-33, /.
Qiu, et al, "Antihepatitis B therapy: a review of current medications and novel small molecule inhibitors", Fudamental & Clinical Pharmacology, pp. 1-18 (XP055105340) (Nov. 1, 2013).
Qiu, et al., "Design and Synthesis of Orally Bioavailable 4-Methyl Heteroaryldihydropyrimidine Based Hepatitis B Virus (HBV) Capsid Inhibitors", Journal of Medicinal Chemistry, vol. 59: pp. 7651-7666, (2016).
Schafer, et al., "Failure is an Option: Learning from unsuccessful proof-of-concepts trails", Drug Discovery Today, vol. 13 (21/22): pp. 913-916 (Nov. 2008).
Schroder, et al., "Arzneimittelchemie Passage", Arzneimittelchemei Grundlagen Nerven Musklen und Gewebe, vol. XX (XX): pp. 30-33 (Jan. 1, 1976).
Shi, et al., "NMR-spectroscopy-based metanonomic approach to the analysis of Bay41-4109, a novel anti-HBV compound, induced hepatotoxcity in rats", Toxicology Letters, vol. 173: pp. 161-167 (2007).
Stalder, et al, "Selective antagonists of mouse trace amine-associated receptor 1 (mTAAR1): Discovery of EPPTB (RO5212773)", Bioorganic & Medicinal Chemistry Letters, vol. 21: pp. 1227-1231 (Dec. 21, 2010).
Stray, et al., "A Heteroaryldihydropyrimidine Activates and Can Misdirect Hepatitis B Virus Capsid Assembly", PNAS, vol. 102(23): pp. 8138-8143 (Jun. 7, 2005).
Stray, et al., "Bay 41-4109 has multiple effects on Hepatitis B virus capsid assembly", Journal of Molecular Recognition,vol. 19: pp. 542-548 (2006).
Tan, et al., Genetically Altering the Thermodynamics and Kinetics of Hepatitis B Virus Capsid Assembly has Profound Effects on Virus Replication in Cell Culture, Journal of Virology, vol. 87(6): pp. 3208-3216 (Mar. 2013).
Taylor, et al., "A Brain-Permeable Small Molecule Reduces Neuronal Cholesterol by Inhibiting Activity of Sirtuin 2 Deacetylase", ASC Chemical Biology, vol. 6: pp. 540-546 (2011).
The Merk Index "Infliximab", An Encyclopedia of Chemicals, Drugs and Biologicals, 14th Ed., p. 924 (2013).
The Merk Index, "Zidovudine", An Encyclopedia of Chemicals, Drugs and Biologicals, 14th Ed., p. 1885 (2013).
Thompson et al., "Toll-like receptors, RIG-I-like RNA Helicases and the Antiviral Innate Immune Response", Immunology and Cell Biology, vol. 85: pp. 435-445 (2007).
Wang, et al., "In vitro inhibition of HBV replication by a novel compound, GLS4, and its efficacy against adefovir-dipovoxil-resistant HBV mutations", Antiviral Therapy, vol. 17:pp. 793-803 (2012).
Wang, et al., "Serum hepatitis B virus RNS is encapsidated pregenome RNA that may be associated with persistence of viral infection and rebound", Journal of Hepatology, vol. 65: pp. 700-710(2016).

(56) References Cited

OTHER PUBLICATIONS

Wang, et al., "Synthesis and Evaluation of Benzothiazole-Based Analogues as Novel, Potent, and Selective Fatty Acid Amide Hydrolase Inhibitors", J. Med. Chem., vol. 52: pp. 170-180 (2009).

Watanabe, et al, "Ortho lithiation of N,N-dimethylbenzenesulfunamide by n-butyllithium. Condensation with electrophilic compounds", Candian Journal of Chemistry, vol. 47: pp. 1543-1546 (Oct. 30, 1968).

Weber et al., "Inhibition of Human Hepatitis B Virus (HBV) by a Novel Non-Nucleosidic Compound in a Transgenic Mouse Model", Antiviral Research, vol. 54: pp. 69-78 (2002).

West, "Chapter 10 Solid Solutions", Solid State Chemistry and Its Applications, John Wiley & Sons, pp. 33-36 (1984).

Wu, et al., "Preclinical Characterization of GLS4, an Inhibitor of Hepatitis B Virus Core Particle Assembly", Antimicrobial Agents and Chemotherapy, vol. 57(11): pp. 5344-5354 (Nov. 2013).

Yang, et al., "Effects of a Hepatitis B Virus Inhibitor, NZ-4, on Capsid Formation", Antiviral Research, vol. 125: pp. 25-33 (2016).

Yang, et al., "Isothiafludine, a novel non-nucleoside compound inhibits hepatitis B virus replication through blocking pregenomic RNA encapsidation", Acta Pharmacologica Sinica, vol. 35: pp. 410-418 (2014).

Yarmolchuk et al., "Synthesis of beta-fluoro-beta-proline", Tetrahedron Letters, vol. 52: pp. 1300-1302, (2011).

Yogaratnam, et al., "Safety, Tolerability and Pharmacokentics of JNJ 56136379, a Novel HBV Capsid Assembly Modulator in Healthy Subjects", The Abstracts of the Liver Meeting 2016 (AASLD), Abstract 1881: pp. 930A-931A, Boston, MA (Oct. 2016).

Yuen, et al., "ARC-520 Produces Deep and Durable Knockdown of Viral Antigen and DNA in Phase II Study in Patients with Chronic Hepatitis B", The Abstracts of the Liver Meeting 2015, Abstract LB-10, pp. 1385A-1386A, San Francisco, CA (Oct. 2015).

Yuen, et al., "NVR 3-778, a first-in-class HBV core inhibitor, alone and in combination with PEG-Interferon (PEGIFN), In treatment-naive HBEAG-positive patients: early reductions in HBV DNA and HBEAG", The Abstracts of he International Liver Congress (EASL), Abstract LB-06: pp. S210-S211 (Oct. 2016).

Zhang, et al., "A Potent Small Molecule Inhibits Polyglutamine Aggregation in Huntington's Disease Neurons and Suppresses Neurodegeneration in Vivo", PNAS, vol. 102 (3): pp. 892-897 (2005).

Zlotnick, et al., "Core Protein: A pleiotropic Keystone in the HBV Lifecycle", Antiviral Research, vol. 121: pp. 82-93 (2015).

Zoulim, et al., "Current Treatments for Chronic Hepatitis B Virus Infections", Current Opinion in Virology, vol. 18: pp. 109-116 (2016).

AMIDE DERIVATIVES USEFUL IN THE TREATMENT OF HBV INFECTION OR HBV-INDUCED DISEASES

CROSS-REFERENCE TO RELATED APPLICATIONS

This application claims priority to EP Patent Application No. 19172736.1, filed May 6, 2019, which is incorporated herein in its entirety.

FIELD

The application relates to amide derivatives, processes for their preparation, pharmaceutical compositions, and their uses, more particularly their uses in treating chronic hepatitis B virus (HBV) infection or HBV-induced diseases.

BACKGROUND

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to suboptimal treatment options and sustained rates of new infections in most parts of the developing world.

Current treatments do not provide a cure and are limited to only two classes of agents (interferon alpha and nucleoside analogues/inhibitors of the viral polymerase); drug resistance, low efficacy, and tolerability issues limit their impact. The low cure rates of HBV are attributed at least in part to the fact that complete suppression of virus production is difficult to achieve with a single antiviral agent. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

The HBV capsid protein plays essential functions during the viral life cycle. HBV capsid/core proteins form metastable viral particles or protein shells that protect the viral genome during intercellular passage, and also play a central role in viral replication processes, including genome encapsidation, genome replication, and virion morphogenesis and egress.

Capsid structures also respond to environmental cues to allow un-coating after viral entry.

Consistently, the appropriate timing of capsid assembly and dis-assembly, the appropriate capsid stability and the function of core protein have been found to be critical for viral infectivity. WO2015/059212 (Janssen R&D Ireland) discloses amide derivatives for the treatment of hepatitis B.

There is a need in the art for therapeutic agents that can increase the suppression of virus production and that can treat, ameliorate, or prevent HBV infection. Administration of such therapeutic agents to an HBV infected patient, either as monotherapy or in combination with other HBV treatments or ancillary treatments, will lead to significantly reduced virus burden, improved prognosis, diminished progression of the disease and enhanced seroconversion rates. Particularly, it is desired to find compounds that are capable of capsid assembly modulation.

SUMMARY

The present invention is directed to compounds capable of capsid assembly modulation. The compounds of the present invention may provide a beneficial balance of properties with respect to prior art compounds. Thus, provided herein is a compound of formula (I)

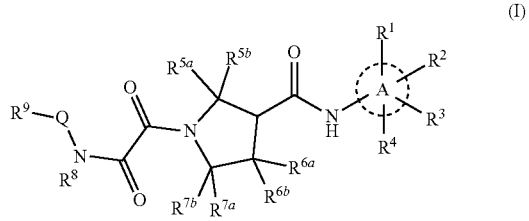

including the stereoisomers or tautomeric forms thereof, wherein:

(A) represents a 6-membered aryl ring optionally containing one or more heteroatom(s), the heteroatom or each of the heteroatoms being nitrogen;

$R^1$, $R^2$ and $R^3$ are each independently selected from the group consisting of H, F, Cl, Br, $CHF_2$, $CH_2F$, $CF_3$, CN, $C_{1-4}$alkyl and $C_{3-6}$cycloalkyl;

$R^4$ is selected from the group consisting of H and F;

$R^{5a}$ and $R^{5b}$ are each independently selected from the group consisting of H, $C_{1-4}$alkyl optionally substituted with one or more F, and $C_{3-6}$cycloalkyl optionally substituted with one or more F;

$R^{6a}$ and $R^{6b}$ are each independently selected from the group consisting of H, $C_{1-4}$alkyl optionally substituted with one or more F, and $C_{3-6}$cycloalkyl optionally substituted with one or more F;

$R^{7a}$ and $R^{7b}$ are each independently selected from the group consisting of H, $C_{1-4}$alkyl optionally substituted with one or more F, and $C_{3-6}$cycloalkyl optionally substituted with one or more F;

Q is selected from the group consisting of
  $C_{1-5}$alkyl, optionally substituted with one or more substituents selected from the group consisting of halogens;
  $C_{2-3}$alkenyl substituted with halogens and more particularly one or more F, 3- to 6-membered monocyclic saturated rings,
  up to 9-membered polycyclic saturated rings,
  wherein the (3- to 6-membered monocyclic or up to 9-membered polycyclic) saturated rings:
    optionally and independently contain one or more heteroatoms, the heteroatoms being independently selected from N, O and S, and/or
    are optionally and independently substituted with one or more substituents selected from the group consisting of F, oxo, OH, C(=O)$NHCH_3$ and $C_{1-4}$alkyl optionally substituted with one or more F;

$R^8$ is H;

$R^9$ is selected from the group consisting of
  phenyl,
  phenyl substituted with one or more substituents each independently selected from the group consisting of halogens, CN, $CF_3$, $CF_2H$, $CH_2F$, $C_{1-4}$alkyl, $C_{3-6}$cycloalkyl, OH and $OC_{1-4}$alkyl, pyridyl,
  pyridyl substituted with one or more substituents each independently selected from the group consisting of halogens, CN, $CF_3$, $CF_2H$, $CH_2F$, $C_{1-4}$alkyl, $C_{3-6}$cycloalkyl, OH and $OC_{1-4}$alkyl, pyrimidyl,
pyrimidyl substituted with one or more substituents each independently selected from the group consisting of halogens, CN, $CF_3$, $CF_2H$, $CH_2F$, $C_{1-4}$alkyl, $C_{3-6}$cycloalkyl, OH and $OC_{1-4}$alkyl,
pyrazinyl,
pyrazinyl substituted with one or more substituents each independently selected from the group consisting of halogens, CN, $CF_3$, $CF_2H$, $CH_2F$, $C_{1-4}$alkyl, $C_{3-6}$cycloalkyl, OH and $OC_{1-4}$alkyl,
pyridazinyl,
pyridazinyl substituted with one or more substituents each independently selected from the group consisting of halogens, CN, $CF_3$, $CF_2H$, $CH_2F$, $C_{1-4}$alkyl, $C_{3-6}$cycloalkyl, OH and $OC_{1-4}$alkyl,
5-membered unsaturated heterocycles containing one to 4 heteroatoms, the heteroatoms being each independently selected from N, O and S, and
5-membered unsaturated heterocycles containing one to 4 heteroatoms, the heteroatoms being each independently selected from N, O and S, substituted with one or more substituents selected from the group consisting of halogens, CN, $CF_3$, $CF_2H$, $CH_2F$, $C_{1-4}$alkyl, $C_{3-6}$cycloalkyl, OH and $OC_{1-4}$alkyl;

or a pharmaceutically acceptable salt or a solvate thereof.

The application provides a pharmaceutical composition comprising at least one compound of formula (I), or a pharmaceutically acceptable salt thereof, together with a pharmaceutically acceptable carrier.

The application provides a pharmaceutical composition comprising at least one disclosed compound, together with a pharmaceutically acceptable carrier. In another aspect, provided herein is a method of treating an HBV infection in an individual in need thereof, comprising administering to the individual a therapeutically effective amount of a compound of formula (I) or a pharmaceutically acceptable salt thereof or of a pharmaceutical composition as described herein.

The application provides a product comprising a first compound and a second compound as a combined preparation for simultaneous, separate or sequential use in the prevention or treatment of an HBV infection or of an HBV-induced disease in mammal in need thereof, wherein said first compound is different from said second compound, wherein said first compound is a compound of formula (I), or a pharmaceutically acceptable salt thereof, or the pharmaceutical composition described in the foregoing paragraph, and wherein said second compound is an HBV inhibitor.

The application provides a method of inhibiting or reducing the formation or presence of HBV DNA-containing particles or HBV RNA-containing particles in an individual in need thereof, comprising administering to the individual a therapeutically effective amount of a compound of formula (I), or a pharmaceutically acceptable salt thereof.

Any of the methods provided herein can further comprise administering to the individual at least one additional therapeutic agent, more particularly at least one other HBV inhibitor.

DESCRIPTION

Provided herein are compounds, e.g., the compounds of formula (I), or pharmaceutically acceptable salts thereof, which are notably useful in the treatment or prevention of HBV infection or of an HBV-associated (or HBV-induced) condition or disease in a subject in need thereof.

Without being bound to any particular mechanism of action, these compounds are believed to modulate or disrupt HBV capsid assembly and other HBV core protein (HBc) functions necessary for HBV replication or the generation of infectious particles and/or may disrupt HBV capsid assembly leading to empty capsids with greatly reduced infectivity or replication capacity. In other words, the compounds provided herein may act as Capsid Assembly Modulators or core protein allosteric modulators (CpAMs).

The compounds provided herein have potent antiviral activity, and are believed to exhibit favorable metabolic properties, tissue distribution, safety and pharmaceutical profiles, and to be suitable for use in humans. Disclosed compounds may modulate (e.g., accelerate, delay, inhibit, disrupt or reduce) normal viral capsid assembly or disassembly, bind capsid or alter metabolism of cellular polyproteins and precursors. The modulation may occur when the capsid protein is mature, or during viral infectivity. Disclosed compounds can be used in methods of modulating the activity or properties of HBV cccDNA, or the generation or release of HBV RNA particles from within an infected cell.

A compound of the application may accelerate the kinetics of HBV capsid assembly, thereby preventing or competing with the encapsidation of the Pol-pgRNA complex and thus blocking the reverse transcription of the pgRNA.

A compound of the application can be assessed e.g., by evaluating the capacity of the compound to induce or to not induce speckling of the Hepatitis B virus core protein (HBc).

HBc is a small protein of about 21 kDa, which forms the icosahedral capsid. HBc has been described e.g., in Diab et al. 2018 (Antiviral Research 149 (2018) 211-220).

Capsid assembly modulators may induce the formation of morphologically intact capsids or the formation of pleiomorphic non-capsid structures. Pleiomorphic non-capsid structures can be visualized in stable HBV-replicating cell lines by immunofluorescence staining against the HBV core protein and appear as "core speckling" in the nucleus and cytoplasm.

The term "HBc speckling" thus refers to the capacity of inducing the formation of such pleiomorphic noncapsid structures.

In an aspect, the application relates more particularly to a compound (as herein described), which does not induce speckling of HBc.

In another aspect, the application relates more particularly to a compound (as herein described), which induces speckling of HBc.

The capacity to induce or to not induce HBc speckling can be assessed by any means which the person of ordinary skill in the art finds appropriate, e.g., by:
  contacting a compound of the application with HBV-infected cells (e.g., cells from a (stable) HBV-infected cell line or HBV infected cells which have been previously collected from an HBV patient);
  optionally fixing and permeabilizing the cells, or optionally lysing the cells; and
  determining whether contacting of these cells with the compound of the application induces or does not induce HBc speckling in these cells.

Determining whether contacting of these cells with the compound of the application induces or does not induce HBc speckling can e.g., involve immunofluorescence staining against HBc, more particularly immunofluorescence staining against HBc with an anti-HBc antibody.

Examples of method to determine whether a compound of the application has or not the capacity to induce HBc speckling comprise the method described in the examples below, and the immunofluorescence assay described in Corcuera et al. 2018 (Antiviral Research (2018), doi/10.1016/j.antiviral.2018.07.011, *"Novel non-heteroarylpyrimidine (HAP) capsid assembly modifiers have a different mode of action from HAPs in vitro"*; cf. § 2.8 of Corcuera et al. 2018). FIG. 5 of Corcuera et al. 2018 illustrates HBV core morphology when a test compound induces HBc speckling (cf. the HAP-treated cells of FIG. 5) and when a test compound does not induce HBc speckling (cf. in FIG. 5, those cells which are treated with a CAM other than HAP).

Complementarily, confirmation that a compound is inducing the formation of pleiomorphic non-capsid structures or not can be obtained by implementing a cell-free biochemical assay using recombinant HBV core dimers (i.e., not using HBV-infected cells but using recombinant HBV core dimers) and using analytical size exclusion chromatography and electron microscopy analysis: cf. e.g., § 2.4-2.5 and FIGS. 2-3 of Corcuera et al. 2018; cf. e.g., Materials and Methods, as well as FIG. 2 of Berke et al. 2017 (Antimicrobial Agents and Chemotherapy August 2017 volume 61 Issue 8 e00560-17 *"Capsid Assembly Modulators have a dual mechanism of action in primary human hepatocytes infected with Hepatitis B virus"*); cf. e.g., the experimental section and FIG. 4 of Huber et al 2018 (ACS Infect Dis. 2018 Dec. 24. doi: 10.1021/acsinfecdis.8b00235; "Novel Hepatitis B Virus Capsid-Targeting Antiviral that Aggregates Core Particles and Inhibits Nuclear Entry of Viral Cores").

In embodiments, the compounds described herein are suitable for monotherapy and are effective against natural or native HBV strains and against HBV strains resistant to currently known drugs.

In another embodiment, the compounds described herein are suitable for use in combination therapy.

Listed below are definitions of various terms used to describe the subject matter of the application.

These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

As used herein, the term "capsid assembly modulator" refers to a compound that disrupts or accelerates or inhibits or hinders or delays or reduces or modifies normal capsid assembly (e.g., during maturation) or normal capsid disassembly (e.g., during infectivity) or perturbs capsid stability, thereby inducing aberrant capsid morphology and function. In one embodiment, a capsid assembly modulator accelerates capsid assembly or disassembly, thereby inducing aberrant capsid morphology. In another embodiment, a capsid assembly modulator interacts (e.g. binds at an active site, binds at an allosteric site, modifies or hinders folding and the like) with the major capsid assembly protein (CA), thereby disrupting capsid assembly or disassembly. In yet another embodiment, a capsid assembly modulator causes a perturbation in structure or function of CA (e.g., ability of CA to assemble, disassemble, bind to a substrate, fold into a suitable conformation, or the like), which attenuates viral infectivity or is lethal to the virus.

As used herein, the term "treatment" or "treating" is defined as the application or administration of a therapeutic agent, i.e., a disclosed compound (alone or in combination with another pharmaceutical agent), to a patient, or application or administration of a therapeutic agent to an isolated tissue or cell line from a patient (e.g., for diagnosis or ex vivo applications), who has an HBV infection, a symptom of HBV infection or the potential to develop an HBV infection, with the purpose to cure, heal, alleviate, relieve, alter, remedy, ameliorate, improve or affect the HBV infection, the symptoms of HBV infection, or the potential to develop an HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the application include the conventional nontoxic salts of the parent compound formed, for example, from non-toxic inorganic or organic acids. The pharmaceutically acceptable salts of the application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound of the application with a pharmaceutically acceptable carrier. The pharmaceutical composition facilitates administration of the compound to a patient or subject.

Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound of the application within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound of the application, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound of the application and are physiologically acceptable to the patient. Supplementary active compounds may also be incorporated into the compositions. The "pharmaceutically acceptable carrier" may further include a pharmaceutically acceptable salt of the compound of the application. Other additional ingredients that may be included in the pharmaceutical compositions of the application are known in the art and described, for example in Remington's Pharmaceutical Sciences (Genaro, Ed., Mack Publishing Co., 1985, Easton, Pa.), which is incorporated herein by reference.

As used herein, the term "alkyl," by itself or as part of another substituent means, unless otherwise stated, a straight or branched chain hydrocarbon having the number of carbon atoms designated (i.e., $C_1$-$C_3$alkyl or $C_{1-3}$ alkyl means an alkyl having one to three carbon atoms, $C_1$-$C_4$ alkyl or $C_{1-4}$alkyl means an alkyl having one to four carbon) and includes straight and branched chains. Examples include methyl, ethyl, propyl, isopropyl, butyl, isobutyl, tert-butyl. Embodiments of alkyl generally include, but are not limited to, $C_1$-$C_{10}$ alkyl, such as $C_1$-$C_6$ alkyl, such as $C_1$-$C_4$ alkyl.

As used herein, the term "alkenyl," by itself or as part of another substituent means, unless otherwise stated, a linear or branched chain of hydrocarbons comprising at least one carbon to carbon double bond, having the number of carbon atoms designated (i.e., $C_2$-$C_4$ alkenyl or $C_{2-4}$alkenyl means an alkenyl having two to four carbon atoms. $C_4$-$C_8$ alkenyl or $C_{4-8}$alkenyl means an alkenyl having four to eight carbon atoms.

As used herein, the term "halo" or "halogen" alone or as part of another substituent means, unless otherwise stated, a fluorine (F), chlorine (Cl), bromine (Br), or iodine (I) atom, preferably, fluorine, chlorine, or bromine, more preferably, fluorine or chlorine.

As used herein, the term "saturated ring" refers to saturated rings optionally contain one or more heteroatoms, the heteroatoms being independently selected from N, O and S.

In the event that no such heteroatoms are present, the saturated ring is a cycloalkyl. The term "cycloalkyl" refers to a mono cyclic non-aromatic saturated radical, wherein each of the atoms forming the ring (i.e., skeletal atoms) is a carbon atom. $C_{3-6}$ cycloalkyl include groups having 3 to 6 ring atoms. Such 3- to 6-membered saturated rings include, but are not limited to, cyclopropyl, cyclobutyl, cyclopentyl and cyclohexyl.

In the event that the saturated ring contains one or more heteroatoms, these are independently selected from N, O and S. It will be understood by the skilled person that the one or more heteroatoms independently selected from N, O and S, will not be selected such as to provide a chemically non-existent structure. Generally, it will be understood that this refers to chemistry that would not be considered aberrant by the skilled person. E.g., the skilled person will be aware that, generally, in a single, 6-membered saturated ring, up to three nitrogen, oxygen, or sulfur atoms can be present. The skilled person will also be aware that, generally, in a single, five- or six-membered saturated ring, several combinations of two heteroatoms can be present, such as nitrogen/nitrogen, nitrogen/oxygen, sulfur/nitrogen, oxygen/oxygen, and sulfur/sulfur. Generally, no adjacent bonds are present selected from the group consisting of O—O, S—N, S—S, and O—S.

Examples of saturated rings include, but are not limited to heterocyclyl groups comprising one, two or three heteroatoms, even more in particular, one or two, and most particular, one heteroatom.

Said ring heteroatoms are each selected from O, S, and N. In embodiments, each heterocyclyl group has from 3 to 6 atoms in its ring system, with the proviso that the ring of said group does not contain two adjacent O or S atoms. The heterocyclyl group can be attached to the remainder of the molecule, unless otherwise stated, at any heteroatom or carbon atom that affords a stable structure.

An example of a 3-membered heterocyclyl group includes, and is not limited to, aziridine. Examples of 4-membered heterocyclyl groups include, and are not limited to, azetidine and a beta lactam. Examples of 5-membered heterocyclyl groups include, and are not limited to, pyrrolidine, oxazolidine and thiazolidinedione. Examples of 6-membered heterocycloalkyl groups include, and are not limited to, piperidine, morpholine, and piperazine.

Other non-limiting examples of heterocyclyl groups include monocyclic groups such as aziridine, oxirane, thiirane, azetidine, oxetane, thietane, pyrrolidine, pyrroline, pyrazolidine, imidazoline, dioxolane, sulfolane, tetrahydrofuran, thiophane, piperidine, piperazine, morpholine, thiomorpholine.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two, or three rings), wherein such rings may be attached together in a pendent manner, such as a biphenyl, or may be fused, such as naphthalene. Examples of aryl groups include phenyl, anthracyl, and naphthyl. Preferred examples are phenyl (e.g., $C_6$-aryl) and biphenyl (e.g., $C_{12}$-aryl). In some embodiments, aryl groups have from six to sixteen carbon atoms. In some embodiments, aryl groups have from six to twelve carbon atoms (e.g., $C_6$-$C_{12}$-aryl). In some embodiments, aryl groups have six carbon atoms (e.g., $C_6$-aryl).

As used herein, the term "heteroaryl" or "heteroaromatic" refers to a heterocycle having aromatic character. By the reference to the aromatic character, the skilled person is aware of the customary limitations to the number of ring atoms. Generally, heteroaryl substituents may be defined by the number of carbon atoms, e.g., $C_{1-12}$heteroaryl, such as $C_{3-9}$ indicates the number of carbon atoms contained in the heteroaryl group without including the number of heteroatoms. For example, a $C_1$-$C_9$-heteroaryl will include an additional one to four heteroatoms. Alternatively, heteroaryl substituents may be defined by the total number of atoms (carbon(s) and heteroatom(s)) in the ring, e.g. 5-membered, 6-membered. A polycyclic heteroaryl may include one or more rings that are partially saturated. Non-limiting examples of heteroaryls include pyridyl, pyrazinyl, pyrimidinyl (including, e.g., 2- and 4-pyrimidinyl), pyridazinyl, thienyl, furyl, pyrrolyl (including, e.g., 2-pyrrolyl), imidazolyl, thiazolyl, oxazolyl, pyrazolyl (including, e.g., 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Non-limiting examples of polycyclic, such as bicyclic, heterocycles and heteroaryls include indolyl (including, e.g., 3-, 4-, 5-, 6- and 7-indolyl), indolinyl, quinolyl, tetrahydroquinolyl, isoquinolyl (including, e.g., 1- and 5-isoquinolyl), 1,2,3,4-tetrahydroisoquinolyl, cinnolinyl, quinoxalinyl (including, e.g., 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g., 3-, 4-, 5-, 6- and 7-benzofuryl), 2,3-dihydrobenzofuryl, 1,2-benzisoxazolyl, benzothienyl (including, e.g., 3-, 4-, 5-, 6-, and 7-benzothienyl), benzoxazolyl, benzothiazolyl (including, e.g., 2-benzothiazolyl and 5-benzothiazolyl), purinyl, benzimidazolyl (including, e.g., 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group.

As used herein, the terminology "selected from . . . " (e.g., "$R^4$ is selected from A, B and C") is understood to be equivalent to the terminology "selected from the group consisting of . . . " (e.g., "$R^4$ is selected from the group consisting of A, B and C").

The application provides a compound of formula (I):

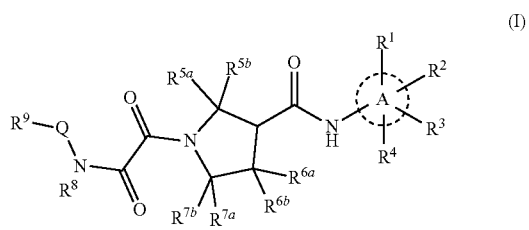

(I)

including the stereoisomers or tautomeric forms thereof, or a pharmaceutically acceptable salt thereof, wherein:

Ⓐ represents a 6-membered aryl ring optionally containing one or more heteroatom(s), wherein the heteroatom or each of the heteroatoms is or are more particularly nitrogen (i.e., wherein Ⓐ represents a 6-membered aryl ring optionally containing one or more nitrogen atom(s));

$R^1$, $R^2$ and $R^3$ are each independently selected from the group consisting of H, F, Cl, Br, $CHF_2$, $CH_2F$, $CF_3$, CN, $C_{1-4}$alkyl and $C_{3-6}$cycloalkyl;

$R^4$ is selected from the group consisting of H and F;

$R^{5a}$ and $R^{5b}$ are selected from the group consisting of H, $C_{1-4}$alkyl optionally substituted with one or more F, and $C_{3-6}$cycloalkyl optionally substituted with one or more F;

$R^{6a}$ and $R^{6b}$ are selected from the group consisting of H, $C_{1-4}$alkyl optionally substituted with one or more F, and $C_{3-6}$cycloalkyl optionally substituted with one or more F;

$R^{7a}$ and $R^{7b}$ are selected from the group consisting of H, $C_{1-4}$alkyl optionally substituted with one or more F, and $C_{3-6}$cycloalkyl optionally substituted with one or more F;

Q is selected from the group consisting of $C_{1-5}$alkyl, optionally substituted with one or more substituents selected from the group consisting of halogens;

$C_{2-3}$alkenyl substituted with halogens and more particularly one or more F, 3- to 6-membered monocyclic saturated rings, up to 9-membered polycyclic saturated rings, wherein the (3- to 6-membered monocyclic or up to 9-membered polycyclic) saturated rings:

optionally (and independently) contain one or more heteroatoms, the heteroatoms being independently selected from N, O and S, and/or are optionally (and independently) substituted with one or more substituents selected from the group consisting of F, oxo, OH, C(=O)NHCH₃ and $C_{1-4}$alkyl optionally substituted with one or more F;

$R^8$ is H;

$R^9$ is selected from the group consisting of phenyl, phenyl substituted with one or more substituents selected from the group consisting of halogens, CN, $CF_3$, $CF_2H$, $CH_2F$, $C_{1-4}$alkyl, $C_{3-6}$cycloalkyl, OH and $OC_{1-4}$alkyl, pyridyl, pyridyl substituted with one or more substituents selected from the group consisting of halogens, CN, $CF_3$, $CF_2H$, $CH_2F$, $C_{1-4}$alkyl, $C_{3-6}$cycloalkyl, OH and $OC_{1-4}$alkyl, pyrimidyl,
pyrimidyl substituted with one or more substituents selected from the group consisting of halogens, CN, $CF_3$, $CF_2H$, $CH_2F$, $C_{1-4}$alkyl, $C_{3-6}$cycloalkyl, OH and $OC_{1-4}$alkyl,
pyrazinyl,
pyrazinyl substituted with one or more substituents selected from the group consisting of halogens, CN, $CF_3$, $CF_2H$, $CH_2F$, $C_{1-4}$alkyl, $C_{3-6}$cycloalkyl, OH and $OC_{1-4}$alkyl,
pyridazinyl,
pyridazinyl substituted with one or more substituents selected from the group consisting of halogens, CN, $CF_3$, $CF_2H$, $CH_2F$, $C_{1-4}$alkyl, $C_{3-6}$cycloalkyl, OH and $OC_{1-4}$alkyl,
5-membered unsaturated heterocycles containing one to 4 heteroatoms, the heteroatoms being independently selected from N, O and S, and
5-membered unsaturated heterocycles containing one to 4 heteroatoms, the heteroatoms being independently selected from N, O and S, substituted with one or more substituents selected from the group consisting of halogens, CN, $CF_3$, $CF_2H$, $CH_2F$, $C_{1-4}$alkyl, $C_{3-6}$cycloalkyl, OH and $OC_{1-4}$alkyl.

In embodiments of the compound of formula (I), Q is $C_{1-5}$alkyl substituted with one or more substituents selected from the group consisting of halogens; or is a 3- to 6-membered monocyclic saturated ring optionally containing one or more heteroatoms, the heteroatoms being independently selected from N, O and S, and optionally substituted with one or more substituents selected from the group consisting of F, oxo, OH, $C(=O)NHCH_3$, $C_{1-4}$alkyl, and $C_{1-4}$alkyl substituted with one or more F.

In embodiments of the compound of formula (I), Q is a 3- to 6-membered monocyclic saturated ring optionally containing one or more heteroatoms, the heteroatoms being independently selected from N, O and S, and optionally substituted with one or more substituents selected from the group consisting of F, oxo, OH, $C(=O)NHCH_3$, $C_{1-4}$alkyl, and $C_{1-4}$alkyl substituted with one or more F.

In embodiments of the compound of formula (I), Q is a 3- to 6-membered monocyclic saturated ring containing one or more heteroatoms, the heteroatoms being independently selected from N, O and S, and substituted with one or more substituents selected from the group consisting of F, oxo, OH, $C(=O)NHCH_3$, $C_{1-4}$alkyl, and $C_{1-4}$alkyl substituted with one or more F.

In embodiments of the compound of formula (I), Q is a $C_{1-4}$alkyl substituted with one or more halogens, in particular fluoro; or is a 3- to 6-membered monocyclic saturated ring containing one substituted with one or more substituents selected from the group consisting of F and $C_{1-4}$alkyl substituted with one or more F.

In embodiments of the compound of formula (I), Q is a 3- to 6-membered monocyclic saturated ring containing one substituted with one or more substituents selected from the group consisting of F and $C_{1-4}$alkyl substituted with one or more F.

In embodiments of the compound of formula (I), $R^9$ is a 5-membered unsaturated heterocycle containing one to 4 heteroatoms, the heteroatoms being selected from N, O and S, and optionally substituted with one or more substituents selected from the group consisting of halogens, CN, $CF_3$, $CF_2H$, $CHF_2$, $C_{1-4}$alkyl, $C_{3-6}$cycloalkyl, OH and $OC_{1-4}$alkyl. Here too, the number and combinations of heteroatoms will be understood to not include chemistry that is not aberrant, as discussed above.

In embodiments of the compound of formula (I), $R^9$ is a triazolyl and optionally substituted with one or more substituents selected from the group consisting of halogens and $C_{1-4}$alkyl; more in particular, $R^9$ is a 1H-1,2,3-triazolyl-4-yl or 4-methyl-1,2,3-triazol-4-yl.

In embodiments of the compound of formula (I), Ⓐ is

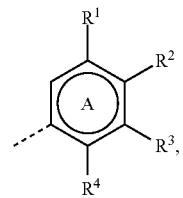

in particular representing phenyl or pyridyl.

In embodiments of the compound of formula (I), R, $R^2$ and $R^3$ are each independently selected from the group consisting of H, F, Cl, Br, $CHF_2$, $CF_3$, CN, and $C_{1-4}$alkyl; and $R^4$ is H or F.

In embodiments of the compound of formula (I), $R^1$ is H, $R^2$ is H or F, $R^3$ is Cl, CN or F and $R^4$ is F.

In embodiments of the compound of formula (I), each of $R^1$ and $R^2$ is H, $R^3$ is Cl or CN, and $R^4$ is F.

In embodiments of the compound of formula (I), R is H, each of $R^2$, $R^3$ and $R^4$ is F.

In embodiments of the compound of formula (I), Ⓐ represents phenyl or pyridyl.

In embodiments of the compound of formula (I), Ⓐ represents phenyl.

In embodiments of the compound of formula (I), Ⓐ is selected from the group consisting of:

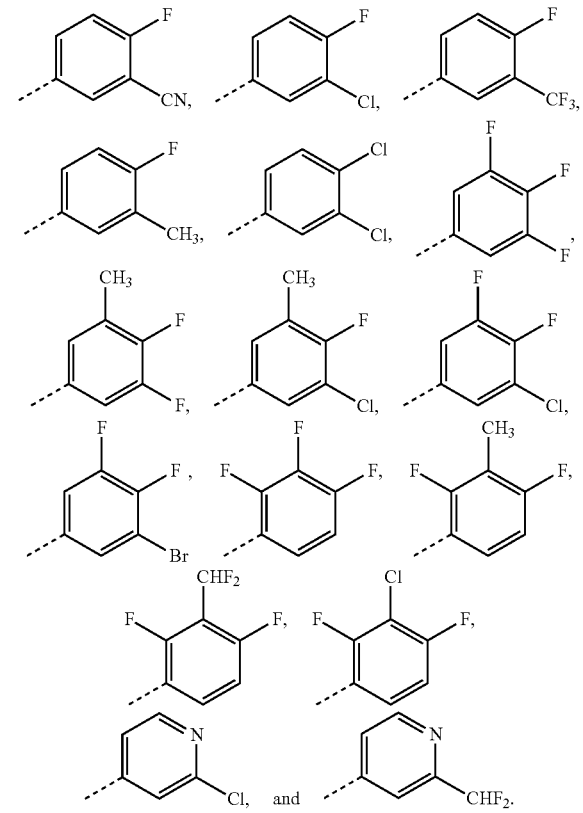

In embodiments of the compound of formula (I), Q is a $C_{1-4}$alkyl substituted with one or more halogens, in particular fluoro; or cyclobutyl optionally substituted with one or more substituents selected from the group consisting of F, oxo, OH, C(=O)NHCH$_3$ and $C_{1-4}$alkyl optionally substituted with one or more F. Q may more particularly be CH$_2$CF$_3$ or cyclobutyl substituted with one or more fluorine, more particularly difluorocyclobutyl, more particularly 3,3-difluorocyclobutyl.

In embodiments of the compound of formula (I), Q is cyclobutyl optionally substituted with one or more substituents selected from the group consisting of F, oxo, OH, C(=O)NHCH$_3$ and $C_{1-4}$alkyl optionally substituted with one or more F. Q may more particularly be cyclobutyl substituted with one or more fluorine, more particularly difluorocyclobutyl, more particularly 3,3-difluorocyclobutyl.

In embodiments of the compound of formula (I), Q is CH$_2$CF$_3$ or 3,3-difluorocyclobutyl.

In embodiments of the compound of formula (I), ⒶⒶ is phenyl and Q is cyclobutyl optionally substituted with one or more substituents selected from the group consisting of F, oxo, OH, C(=O)NHCH$_3$ and $C_{1-4}$alkyl optionally substituted with one or more F. Q may more particularly be cyclobutyl substituted with one or more fluorine, more particularly difluorocyclobutyl, more particularly 3,3-difluorocyclobutyl.

In embodiments of the compound of formula (I), Q is 3- to 6-membered monocyclic saturated rings, wherein the (3- to 6-membered monocyclic) saturated rings:

optionally (and independently) contain one or more heteroatoms, the heteroatoms being independently selected from N, O and S, and/or are optionally (and independently) substituted with one or more substituents selected from the group consisting of F, oxo, OH, C(=O)NHCH$_3$ and $C_{1-4}$alkyl optionally substituted with one or more F.

ⒶⒶ may e.g, be phenyl.

In embodiments of the compound of formula (I),
$R^{5a}$ and $R^{5b}$ are each independently selected from the group consisting of H and methyl;
$R^{6a}$ and $R^{6b}$ are each independently selected from the group consisting of H and methyl; and
$R^{7a}$ and $R^{7b}$ are each independently selected from the group consisting of H and methyl.

In embodiments of the compound of formula (I),
$R^{5a}$ is methyl and $R^{5b}$ is H;
$R^{6a}$ and $R^{6b}$ are H; and
$R^{7a}$ and $R^{7b}$ are each independently selected from the group consisting of H and methyl.

In embodiments of the compound of formula (I),
$R^{5a}$ and $R^{5b}$ are H;
$R^{6a}$ and $R^{6b}$ are H; and
$R^{7a}$ is methyl and $R^{7b}$ is H.

All combinations of the embodiments discussed hereinbefore or hereinafter are expressly included.

Compounds in accordance with the application include, but are not limited to compounds having the following formulae:

TABLE 1

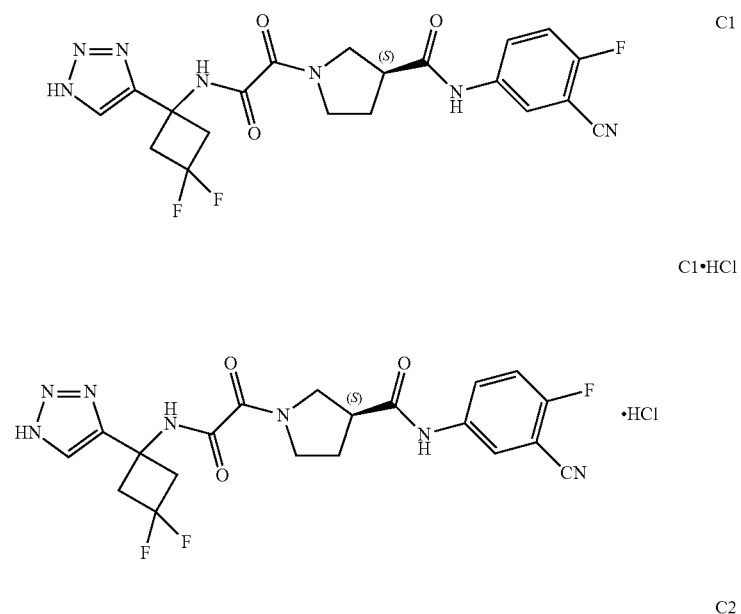

TABLE 1-continued

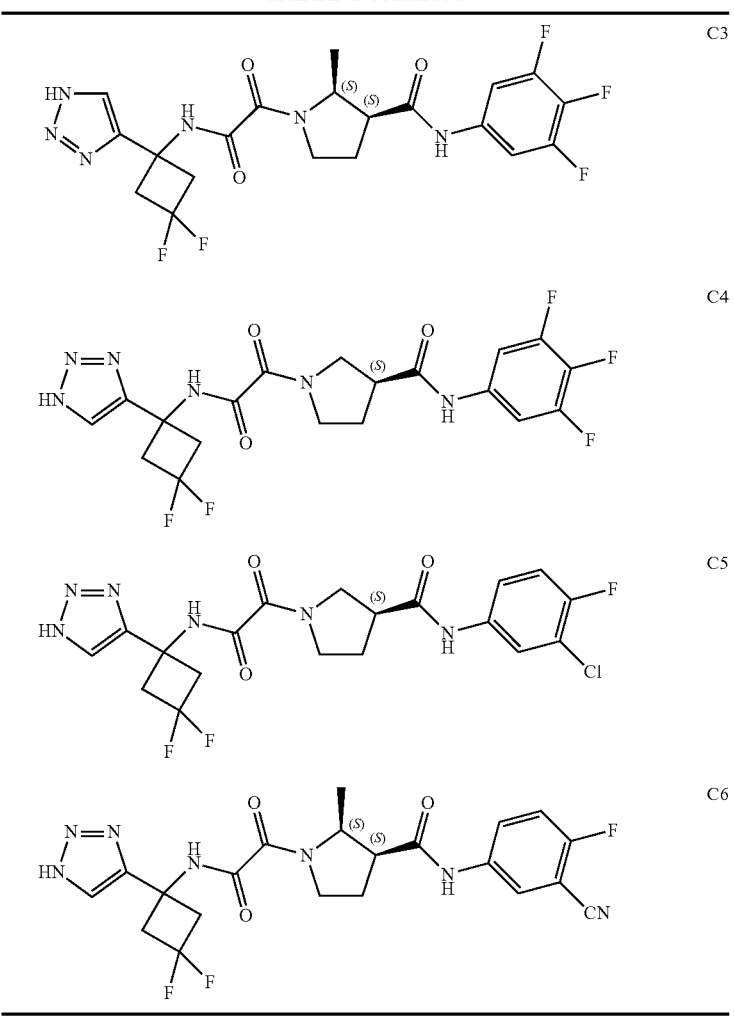

More particularly, compounds in accordance with the application include, but are not limited to compounds having the formula C1, C1.HCl, C2, C3, $C_{1-4}$, C5 or C6 (cf. Table 1 above).

More particularly, compounds in accordance with the application include, but are not limited to compounds having the formula chosen from among formulas C1, C1.HCl, C2, $C_{1-4}$ and C5 (cf. Table 1 above).

More particularly, compounds in accordance with the application include, but are not limited to compounds having the formula chosen from among formulas C3 and C6 (cf. Table 1 above).

More particularly, compounds in accordance with the application include, but are not limited to compounds having the formula chosen from among formulas C3 and $C_{1-4}$ (cf. Table 1 above).

More particularly, compounds in accordance with the application include, but are not limited to compounds having the formula chosen from among formulas C1, C1.HCl, C2, C5 and C6 (cf. Table 1 above).

The disclosed compounds may possess one or more stereocenters, and each stereocenter may exist independently in either R or S configuration. The stereochemical configuration may be assigned at indicated centers as (*R), (*S), (R*) or (S*) when the absolute stereochemistry is undetermined although the compound itself has been isolated as a single stereoisomer and is enantiomerically/diastereomerically pure. Whenever the notation (*R), (*S), (R*) or (S*) is indicated herein in two adjacent carbon centres as further specified by the solid/hashed wedged bonds, wherein the solid/hashed wedged bonds have been assigned at random to indicate the cis or the trans diastereoisomer, it denotes that the compound is a single cis or trans diastereoisomer, as it may be indicated, e.g. C3' corresponds to a trans diastereoisomer of undetermined absolute stereochemistry. Compounds described herein are present in optically active or racemic forms. It is to be understood that the compounds described herein encompass racemic, optically-active, regioisomeric and stereoisomeric forms, or combinations thereof that possess the therapeutically useful properties described herein. The absolute configuration is specified according to the Cahn-Ingold-Prelog system. When the absolute R or S stereochemistry of a compound cannot be determined, it can be identified by the retention time after chromatography under particular chromatographic conditions as determined by chromatographic column, eluent etc.

A stereoisomeric form of a compound refers to all possible compounds made up of the same atoms bonded by the same sequence of bonds but having different three-dimensional structures which are not interchangeable.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. A mixture of one or more isomers can be utilized as the disclosed compound described herein. Compounds described herein may contain one or more chiral centers.

These compounds can be prepared by any means, including stereoselective synthesis, enantioselective synthesis or separation of a mixture of enantiomers or diastereomers. Resolution of compounds and isomers thereof can be achieved by any means including, by way of non-limiting example, chemical processes, enzymatic processes, fractional crystallization, distillation, and chromatography.

The disclosed compounds may exist as tautomers. A "tautomer" refers to a proton-shift from one atom of the molecule to another atom of the same molecule. All tautomers are included within the scope of the compounds presented herein.

Therefore, hereinbefore and hereinafter, the term "compound of formula (I)" is meant to include the stereoisomers thereof and the tautomeric forms thereof.

Compounds described herein also include isotopically-labeled compounds wherein one or more atoms are replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. Isotopically-labeled compounds can be useful in drug or substrate tissue distribution studies. Substitution with heavier isotopes such as deuterium may afford greater metabolic stability (which may lead to for example, increased in vivo half-life or reduced dosage requirements).

Substitution with positron emitting isotopes, such as $^{11}$C, $^{18}$F, $^{15}$ and $^{13}$N, can be useful in Positron Emission Topography (PET) studies for examining substrate receptor occupancy. Isotopically-labeled compounds can be prepared by any suitable method or by processes using an appropriate isotopically-labeled reagent in place of the non-labeled reagent otherwise employed.

The compounds described herein may be labeled by other means, including, but not limited to, the use of chromophores or fluorescent moieties, bioluminescent labels, or chemiluminescent labels. The compounds described herein, and other related compounds having different substituents can be synthesized using techniques and materials described herein and techniques known to the person of average skill in the art. General methods for the preparation of compound as described herein can be modified by the use of appropriate reagents and conditions, for the introduction of the various moieties found in the formula as provided herein.

Compounds described herein may be synthesized using any suitable procedures starting from compounds that are available from commercial sources or are prepared using procedures described herein.

A compound of the application may be useful for reducing viral load associated with an HBV infection in an individual in need thereof, e.g., by administering to an individual in need thereof a therapeutically effective amount of a disclosed compound.

A compound of the application may be useful for reducing reoccurrence of an HBV infection in an individual in need thereof, e.g., by administering to an individual in need thereof a therapeutically effective amount of a disclosed compound.

A compound of the application may be useful for inhibiting or reducing the formation or presence of HBV DNA-containing particles or HBV RNA-containing particles in an individual in need thereof, e.g., by administering to the individual a therapeutically effective amount of a disclosed compound.

A compound of the application can be useful for reducing an adverse physiological impact of an HBV infection in an individual in need thereof, e.g., by administering to the individual a therapeutically effective amount of a disclosed compound.

A compound of the application may be useful for reducing, slowing, or inhibiting an HBV infection in an individual in need thereof, e.g., by administering to the individual a therapeutically effective amount of a disclosed compound.

A compound of the application may be useful for inducing reversal of hepatic injury from an HBV infection in an individual in need thereof, e.g., by administering to the individual a therapeutically effective amount of a disclosed compound.

A compound of the application may be useful for reducing the physiological impact of long-term antiviral therapy for HBV infection in an individual in need thereof, e.g., by administering to the individual a therapeutically effective amount of a disclosed compound.

A compound of the application may be useful for prophylactically treating an HBV infection in an individual in need thereof, wherein the individual is afflicted with a latent HBV infection, e.g., by administering to the individual a therapeutically effective amount of a disclosed compound.

A compound of the application may be useful for increasing or normalizing or restoring normal health, or eliciting full recovery of normal health, or restoring life expectancy, or resolving the viral infection in the individual in need thereof.

The application relates to a pharmaceutical composition, which comprises at least one compound or pharmaceutically acceptable salt as herein described, and which further comprises at least one pharmaceutically acceptable carrier.

The application relates to such a compound or pharmaceutically acceptable salt, or to such a pharmaceutical composition, for use as a medicament.

The application relates to such a compound or pharmaceutically acceptable salt, or to such a pharmaceutical composition, for use in the prevention or treatment of an HBV infection or of an HBV-induced disease in mammal in need thereof.

The application relates to such a compound or pharmaceutically acceptable salt, or to such a pharmaceutical composition, for use in the prevention, the prevention of aggravation, the amelioration or the treatment of chronic Hepatitis B.

The application relates to such a compound or pharmaceutically acceptable salt, or to such a pharmaceutical composition, for use in the prevention, the prevention of aggravation, the amelioration or the treatment of a HBV-induced disease or condition.

HBV-induced disease or condition includes progressive liver fibrosis, inflammation and necrosis leading to cirrhosis, end-stage liver disease, and hepatocellular carcinoma. Additionally, HBV acts as a helper virus to hepatitis delta virus (HDV), and it is estimated that more than 15 million people may be HBV/HDV co-infected worldwide, with an increased risk of rapid progression to cirrhosis and increased hepatic decompensation, than patients suffering from HBV alone (Hughes, S. A. et al. Lancet 2011, 378, 73-85). HDV, infects therefore subjects suffering from HBV infection. In a particular embodiment, the compounds of the invention may be used in the treatment and/or prophylaxis of HBV/HDV co-infection, or diseases associated with HBV/HDV co infection. Therefore, in a particular embodiment, the HBV infection is in particular HBV/HDV co-infection, and the mammal, in particular the human, may be HBV/HDV co-infected, or be at risk of HBV/HDV co infection.

The application relates to such a compound or pharmaceutically acceptable salt, or to such a pharmaceutical composition, for any of the above-mentioned uses, more particularly for use in the prevention, the prevention of aggravation, the amelioration, or the treatment of one or more of the following items:
- the prevention of chronic hepatitis infection, more particularly chronic hepatitis B infection (ie, preventing that the hepatitis (B) infection becomes chronic);
- the amelioration or treatment of a hepatitis-associated or hepatitis-induced (chronic) disease or condition, more particularly of a hepatitis B-associated or hepatitis B-induced (chronic) disease or condition;
- the prevention of the aggravation of a hepatitis-associated or hepatitis-induced (chronic) disease or condition, more particularly of a hepatitis B-associated or hepatitis B-induced (chronic) disease or condition;
- the amelioration (regression, or absence of progression) of the stage of liver fibrosis, or of the extent of liver damage, induced by a (chronic) hepatitis infection, more particularly by a (chronic) hepatitis B infection;
- the amelioration (reduction) of the fibrosis progression rate of a (chronic) hepatitis infection, more particularly the prevention of cirrhosis in a subject having a (chronic) hepatitis infection, more particularly by a (chronic) hepatitis B infection (e.g., preventing that the subject reaches the cirrhotic stage of fibrosis).

The compounds of the application may exist in unsolvated and solvated forms. The term "solvate" is used herein to describe a molecular complex comprising the compound of the application and one or more pharmaceutically acceptable solvent molecules, for example, ethanol.

The term "polymorph" refers to the ability of the compound of the application to exist in more than one form or crystal structure.

The compounds of the application may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the application or in combination with one or more other drugs. Generally, they will be administered as a formulation in association with one or more pharmaceutically acceptable excipients. The term "excipient" is used herein to describe any ingredient other than the compound(s) of the application. The choice of excipient depends largely on factors such as the particular mode of administration, the effect of the excipient on solubility and stability, and the nature of the dosage form.

The application also relates to a product comprising a first compound and a second compound as a combined preparation for simultaneous, separate or sequential use in the prevention or treatment of an HBV infection or of an HBV-induced disease in mammal in need thereof, wherein said first compound is different from said second compound, wherein said first compound is the compound or pharmaceutically acceptable salt as herein described, or the pharmaceutical composition of the application, and wherein said second compound is another HBV inhibitor.

For example, a second compound is another HBV inhibitor which is selected from the group consisting HBV combination drugs, HBV DNA polymerase inhibitors, immunomodulators, toll-like (TLR) receptor modulators, interferon alpha receptor ligands, hyaluronidase inhibitors, hepatitis b surface antigen (HbsAg) inhibitors, cytotoxic T-lymphocyte-associated protein 4 (ipi4) inhibitors, cyclohilin inhibitors, HBV viral entry inhibitors, antisense oligonucleotide targeting viral mRNA, short interfering RNAs (siRNA) and ddRNAi endonuclease modulators, ribonucleotide reductase inhibitors, HBV E antigen inhibitors, covalently closed circular DNA (cccDNA) inhibitors, famsoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (P13K) inhibitors, indole amine 2,3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, and other HBV drugs.

The compounds of the application or any subgroup thereof may be formulated into various pharmaceutical forms for administration purposes. As appropriate compositions there may be cited all compositions usually employed for systemically administering drugs. To prepare the pharmaceutical compositions of the application, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the application may also be administered via inhalation or insufflation by means of methods and formulations employed in the art for administration via this way. Thus, in general the compounds of the application may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general, it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the application. The effective amount ranges mentioned above are therefore only guidelines and are not intended to limit the scope or use of the application to any extent.

In the preparation of the compounds several intermediate compounds can be used. In this respect an aspect of this disclosure relates to compounds having the following formula (II):

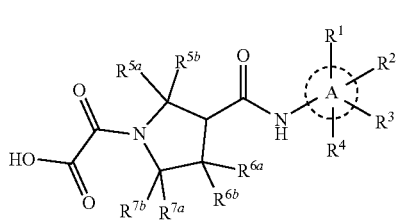

(II)

wherein Ⓐ, $R^1$, $R^2$, $R^3$, $R^4$, $R^{5a}$, $R^{5b}$, $R^{6a}$, $R^{6b}$, $R^{7a}$ and $R^{7b}$ have the abovementioned meaning.

In preparing the compounds the intermediates of formula (II) can be reacted, e.g., with an intermediate of formula (III):

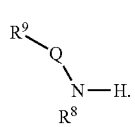

(III)

wherein $R^8$, $R^9$ and Q have the abovementioned meaning.

Intermediates in accordance with the present disclosure include but are not limited to intermediate compounds having the formulae shown in the synthesis examples given below.

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited.

The term "essentially consisting of" is a partially open term, which does not exclude additional, unrecited element(s), step(s), or ingredient(s), as long as these additional element(s), step(s) or ingredient(s) do not materially affect the basic and novel properties of the subject matter of the application.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of").

In an attempt to help the reader of the present application, the description has been separated in various paragraphs or sections. These separations should not be considered as disconnecting the substance of a paragraph or section from the substance of another paragraph or section. To the contrary, the present description encompasses all the combinations of the various sections, paragraphs and sentences that can be contemplated.

Each of the relevant disclosures of all references cited herein is specifically incorporated by reference. The following examples are offered by way of illustration, and not by way of limitation.

EXAMPLES

Exemplary compounds useful in methods of the application will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product.

Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to formula (I). Reactions may be performed between the melting point and the reflux temperature of the solvent, and preferably between 0° C. and the reflux temperature of the solvent. Reactions may be heated employing conventional heating or microwave heating.

Reactions may also be conducted in sealed pressure vessels above the normal reflux temperature of the solvent.

1. General Information

Chemical Names

Chemical names were generated using the chemistry software: ACD/ChemSketch.

General Procedure for LCMS Methods

The High Performance Liquid Chromatography (HPLC) measurement was performed using a LC pump, a diode-array (DAD) or a UV detector and a column as specified in the respective methods.

If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (Rt) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica, "Q-Tof" Quadrupole Time-of-flight mass spectrometers, "CLND", ChemiLuminescent Nitrogen Detector, "ELSD" Evaporative Light Scanning Detector, LCMS Methods
(Flow expressed in mL/min; column temperature (T) in ° C.; Run time in minutes).

General Procedure for SFC Methods

The SFC measurement was performed using an Analytical Supercritical fluid chromatography (SFC) system composed by a binary pump for delivering carbon dioxide (CO2) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Analytical SFC-MS Methods (Flow expressed in mL/min; column temperature (T) in ° C.; Run time in minutes, Backpressure (BPR) in bars.

SFC Methods
(Flow expressed in mL/min; column temperature (T) in ° C.; Run time in minutes).

| Method code | Column | Mobile phase | Gradient | $\frac{Flow}{ColT}$ | Run time |
|---|---|---|---|---|---|
| SFC_A | Daicel Chiralpak ® IC3 column (3.0 μm, 150 × 4.6 mm) | A:CO$_2$ B: EtOH + 0.2% iPrNH$_2$ | 10%-50% B in 6 min, hold 3.5 min | $\frac{2.5}{40}$ | $\frac{9.5}{130}$ |

| Method code | Instrument | Column | Mobile phase | Gradient | $\frac{Flow}{Col\ T}$ | Run time |
|---|---|---|---|---|---|---|
| A | Waters: Acquity ® UPLC ®-DAD and SQD | Waters: BEH C18 (1.7 μm, 2.1 * 50 mm) | A: 10 mM CH$_3$COONH$_4$ in 95% H$_2$O + 5% CH$_3$CN B: CH$_3$CN | From 95% A to 5% A in 1.3 min, held for 0.7 min. | $\frac{0.8}{55}$ | 2 |
| B | Waters: Acquity ® UPLC ®-DAD and SQD | Waters: BEH (1.8 μm, 2.1 * 100 mm) | A: 10 mM CH$_3$COONH$_4$ in 95% H$_2$O + 5% CH$_3$CN B: CH$_3$CN | From 100% A to 5% A in 2.10 min, to 0% A in 0.90 min, to 5% A in 0.5 min | $\frac{0.6}{55}$ | 3.5 |
| C | Thermoscientific Ultimate 3000 DAD and Brucker HCT ultra | Agilent: Poroshell EC-C18 (4 μm, 4.6 × 100 mm) | A: HCO$_2$H 0.1% in water/ B: HCOOH 0.05% in CH$_3$CN | 98% A for 2 min, to 0% A in 10 min, held for 3.4 min, back to 98% A in 1.3 min, held for 1.7 min | $\frac{1}{30}$ | 18.4 |
| D | Waters: Acquity ® UPLC ®-DAD, SQD and ELSD | Waters: HSS T3 (1.8 μm, 2.1 * 100 mm) | A: 10 mM CH$_3$COONH$_4$ in 95% H$_2$O + 5% CH$_3$CN B: CH$_3$CN | From 100% A to 5% A in 2.10 min, to 0% A in 90.0 min, to 5% A in 0.5 min | $\frac{0.7}{55}$ | 3.5 |
| E | Waters: Acquity ® UPLC ®-DAD and SQD | Waters: BEH (1.8 μm, 2.1 * 100 mm) | A: 10 mM CH$_3$COONH$_4$ in 95% H$_2$O + 5% CH$_3$CN B: MeOH | From 100% A to 5% A in 2.10 min, to 0% A in 0.90 min, to 5% A in 0.5 min | $\frac{0.7}{55}$ | 3.5 |
| F | Waters: Acquity ® UPLC ®-DAD and SQD | Waters: BEH (1.8 μm, 2.1 * 100 mm) | A: 10 mM CH$_3$COONH$_4$ in 95% H$_2$O + 5% CH$_3$CN B: CH$_3$CN | From 100% A to 5% A in 2.10 min, to 0% A in 0.9 min, to 5% A in 0.4 min | $\frac{0.6}{55}$ | 3.5 |

-continued

| Method code | Column | Mobile phase | Gradient | Flow/ColT | Run time |
|---|---|---|---|---|---|
| SFC_B | Daicel Chiralpak ® IC3 column (3.0 μm, 150 × 4.6 mm) | A:$CO_2$ B: EtOH + 0.2% iPrNH$_2$ | 10%-50% B in 6 min, hold 3.5 min | 2.5/40 | 9.5/130 |
| SFC_C | Daicel Chiralpak ® AD3 column (3.0 μm, 150 × 4.6 mm) | A:$CO_2$ B: MeOH + 0.2% iPrNH$_2$ | 10%-50% B in 6 min, hold 3.5 min | 2.5/40 | 9.5/130 |
| SFC_D | Daicel Chiralpak ® IC3 column (3.0 μm, 150 × 4.6 mm) | A:$CO_2$ B: iPrOH + 0.2% iPrNH$_2$ | 10%-50% B in 6 min, hold 3.5 min | 2.5/40 | 9.5/130 |
| SFC_E | Daicel Chiralpak ® IG3 column (3.0 μm, 150 × 4.6 mm) | A:$CO_2$ B: MeOH + 0.2% iPrNH$_2$ | 10%-50% B in 6 min, hold 3.5 min | 2.5/40 | 9.5/130 |
| SFC_F | Daicel Chiralpak ® IG3 column (3.0 μm, 150 × 4.6 mm) | A:$CO_2$ B: EtOH + 0.2% iPrNH$_2$ | 10%-50% B in 6 min, hold 3.5 min | 2.5/40 | 9.5/130 |
| SFC_G | Daicel Chiralpak ® IG3 column (3.0 μm, 150 × 4.6 mm) | A:$CO_2$ B: EtOH + 0.2% iPrNH$_2$ | 10%-50% B in 6 min, hold 3.5 min | 2.5/40 | 9.5/130 |
| SFC_H | Daicel Chiralpak ® IG3 column (3.0 μm, 150 × 4.6 mm) | A:$CO_2$ B: EtOH + 0.2% iPrNH$_2$ | 15% B hold 6 min, to 50% in 1 min hold 2.5 min | 2.5/40 | 9.5/130 |

NMR Analysis $^1$H NMR spectra were recorded on 1) a Bruker DPX400 MHz spectrometer or 2) a Bruker Avance 400 MHz spectrometer or 3) a Bruker Avance 111400 MHz spectrometer or 4) a Bruker Avance 600 MHz spectrometer or 5) a Bruker Avance NEO400 MHz spectrometer.

NMR spectra were recorded at ambient temperature unless other wise stated. Data are reported as follow: chemical shift in parts per million (ppm) relative to TMS (δ=0 ppm) on the scale, integration, multiplicity (s=singlet, d=doublet, =triplet, q=quartet, quin=quintuplet, sext=sextuplet, sept=septuplet, m=multiplet, b=broad, or a combination of these), coupling constant(s) J in Hertz (Hz).

2. Abbreviations

TABLE 3

| | |
|---|---|
| AcOH | Acetic acid |
| BOC | tert-butyloxycarbonyl protecting group |
| DBU | 1,8-Diazabicyclo[5.4.0]undec-7-ene |
| DCM | Dichloromethane |
| DIPE | Di-isopropylether |
| DIPEA | N,N-Diisopropylethylamine |
| DMF | N,N-Dimethylformamide |
| DMSO-d$_6$ | Hexadeuterodimethyl sulfoxide |
| Et$_3$N | Triethylamine |
| EtOAc | Ethyl acetate |
| EtOH | Ethanol |
| h | Hour |
| HATU | 1-[Bis(dimethylamino)methylene]-1H-1,2,3-triazolo[4,5-b]pyridinium 3-oxid hexafluorophosphate |
| HPLC | High Performance Liquid Chromatography |
| i-PrOH | Propan-2-ol |
| LCMS | Liquid Chromatography Mass Spectrometry |
| MeOH | Methanol |
| min | Minute |
| NBS | N-Bromosuccinimide |
| NMR | Nuclear Magnetic Resonance |
| o/n | Overnight |
| PPACA | Propylphosphonic anhydride |
| rt | Room temperature |
| Rt | Retention time |
| THF | Tetrahydrofuran |

3. Procedures 3.1. Synthesis of Intermediates 3.1.1. Synthesis of Intermediate 4

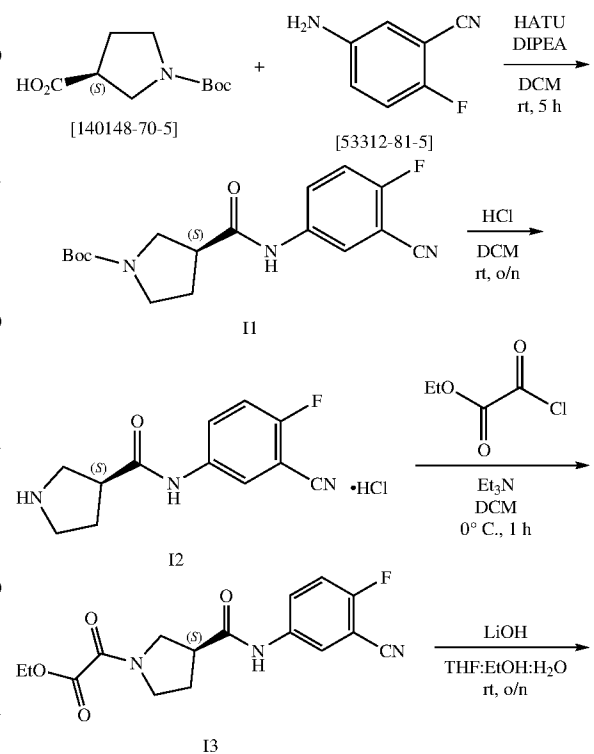

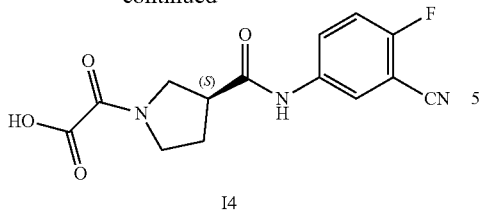

Intermediate I1 tert-Butyl (3S)-[(3-cyano-4-fluorophenyl)carbamoyl]pyrrolidine-1-carboxylate

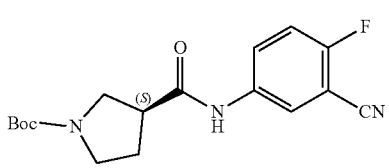

A mixture of 5-amino-2-fluorobenzonitrile (13.3 g, 97.6 mmol), (S)-1-boc-pyrrolidine-3-caboxylic acid (20.0 g, 92.9 mmol), HATU (42.4 g, 112 mmol) and DIPEA (48.0 mL, 279 mmol) in DCM (500 mL) was stirred at room temperature for 5 h. The reaction mixture was diluted with water (100 mL) and HCl (12M, aq., 25 mL) was added. The organic layer was evaporated to dryness and the residue was purified by flash column chromatography (silica, mobile phase: heptane/EtOAc) to afford intermediate I1 (30.97 g) which was used as such the next step.

Intermediate I2

(3S)—N-(3-cyano-4-fluorophenyl)pyrrolidine-3-carboxamide hydrochloride

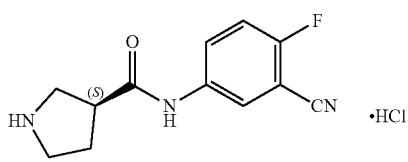

Intermediate I1 (30.9 g, 92.9 mmol) was dissolved in DCM (100 mL). HCl (6M in i-PrOH, 155 mL, 929 mmol) was added and the reaction mixture was stirred overnight at room temperature.

The precipitate was filtered off and triturated with DIPE. The solid was collected by filtration and dried at 55-60° C. to afford a first fraction of intermediate I2 (12.2 g, 48%). The filtrate was concentrated in vacuo, and DCM (25 mL) and DIPE (150 mL) were added. The precipitate was filtered off and triturated in DIPE. The solid was collected by filtration and dried at 55-60° C. to afford a second fraction of intermediate I2 (5.6 g, 22%). The filtrate was concentrated in vacuo to afford a third fraction of intermediate I2 (9.38 g, 20%, 55% purity).

Intermediate I3

Ethyl {(3S)-[(3-cyano-4-fluorophenyl)carbamoyl]pyrrolidin-1-yl}(oxo)acetate

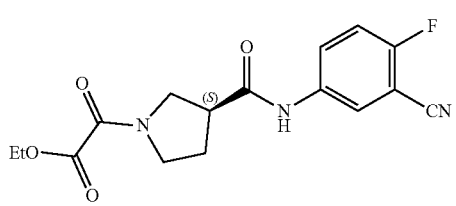

Ethyl chlorooxoacetate (2.56 mL, 22.8 mmol) was added to a suspension of intermediate I2 (5.6 g, 20.8 mmol) and Et₃N (11.5 mL, 83.0 mmol) in DCM (50 mL) at 0° C. The reaction mixture was stirred for 1 h. The reaction mixture was diluted with EtOAc (200 mL) and washed with HCl (N aq.), NaHCO₃ (aq., sat.) and brine, dried (MgSO₄), filtered and evaporated to dryness to afford intermediate I3 as an oil.

Intermediate I4

{(3S)-[(3-Cyano-4-fluorophenyl)carbamoyl]pyrrolidin-1-yl}(oxo)acetic acid

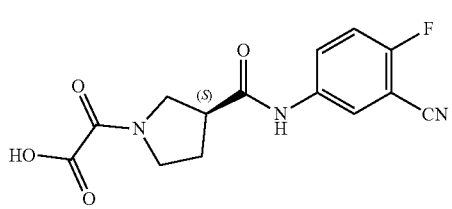

Crude intermediate I3 and LiOH (746 mg, 31.1 mmol) were dissolved in a mixture of THF (100 mL), water (5 mL) and EtOH (5 mL). The reaction mixture was stirred at room temperature overnight. Additional amount of LiOH (200 mg, 8.35 mmol) was added and the reaction mixture was stirred for another 30 min. The reaction mixture was diluted with water (200 mL) and HCl (1M in H₂O, 41.5 mL, 41.5 mmol) was added. The layers were separated and the aqueous phase was extracted with 2-MeTHF (200 mL). The combined organic extracts were dried (Na₂SO₄), filtered and evaporated to dryness to afford intermediate I4 (5.94 g, 94% over 2 steps).

3.1.2 Synthesis of Intermediate I6

{(3S)-3-[(4-Fluoro-3-methylphenyl)carbamoyl]pyrrolidin-1-yl}(oxo)acetic acid

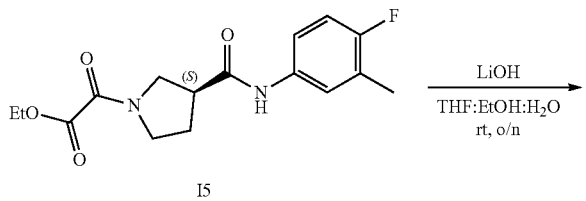

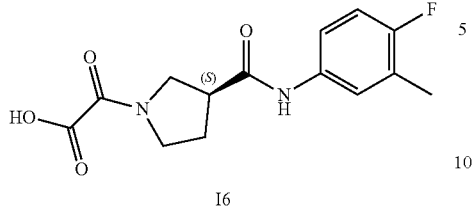

I6

Ethyl {(3S)-3-[(4-fluoro-3-methylphenyl)carbamoyl]pyrrolidine-1-yl}(oxo)acetate 5 (250 mg, 0.78 mmol) and LiOH (27.9 mg, 1.16 mmol) were dissolved in a mixture of THF (5 mL), water (1 mL) and EtOH (1 mL). The reaction mixture was stirred at room temperature for 30 min. The reaction mixture was diluted with water (10 mL), and HCl (1M in H$_2$O, 1.16 mL, 1.16 mmol) was added. The layers were separated and the aqueous phase was extracted with 2-MeTHF (3×10 mL). The combined organic layers were dried (Na$_2$SO$_4$), filtered and evaporated to dryness to afford a crude mixture of I6 which was used as such in the next step.

3.1.3. Synthesis of Intermediate I11

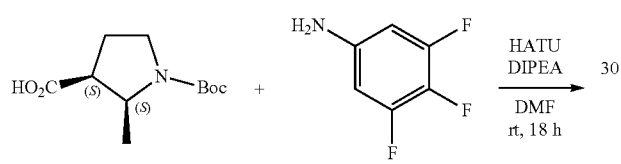

[664364-34-5]   [163733-96-8]

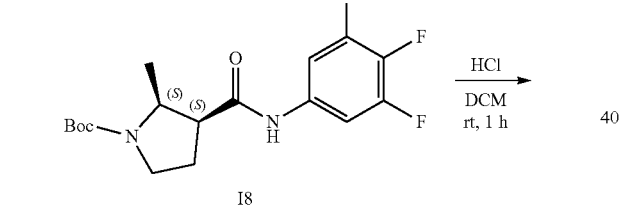

I8

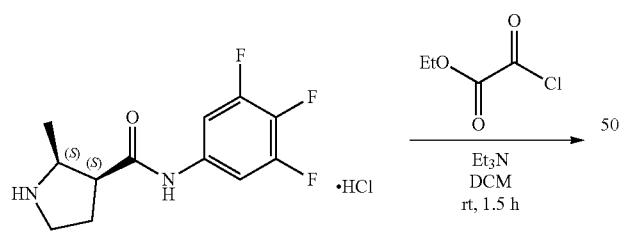

I9

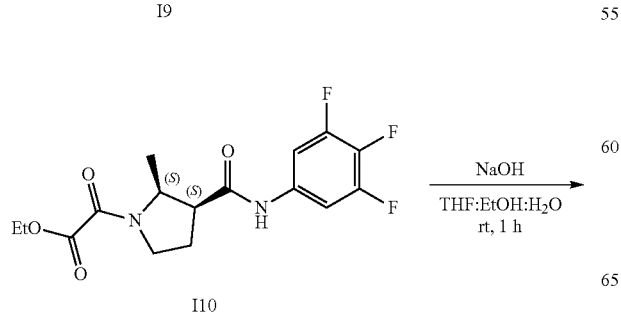

I10

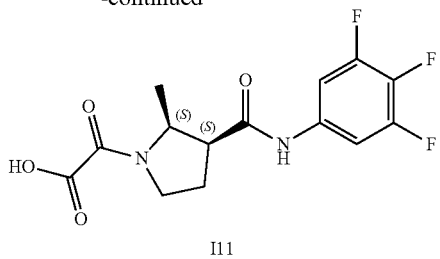

I11

Intermediate I8 tert-Butyl (2S,3S)-2-methyl-3-[(3,4,5-trifluorophenyl)carbamoyl]pyrrolidine-1-carboxylate

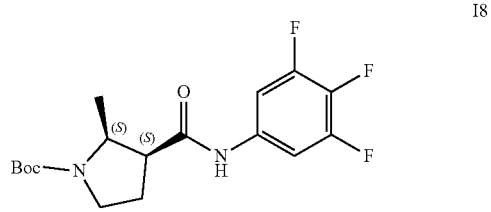

I8

The reaction was performed under anhydrous conditions and under Ar atmosphere.

To a solution of 2S,3S-1-[(tert-butoxy)carbonyl]-2-methylpyrrolidine-3-carboxylic acid (250 mg, 1.09 mmol) and 3,4,5-trifluoroaniline (321 mg, 2.18 mmol) in DMF (10 mL) were added HATU (829 mg, 2.18 mmol) and DIPEA (570 μL, 3.27 mmol). The reaction mixture was stirred at room temperature for 18 h and diluted with water (30 mL) and EtOAc (30 mL). The layers were separated, and the aqueous phase was extracted with EtOAc (2×30 mL). The combined organic layers were washed successively with brine (3×40 mL), HCl (1M, aq., 2×30 mL), and NaHCO$_3$ (sat., aq., 30 mL), dried (Na$_2$SO$_4$), filtered and concentrated under reduced pressure. The crude mixture was purified by flash column chromatography (silica, mobile phase: cyclohexane/EtOAc, gradient from 9:1 to 5:5) to give intermediate I8 (314 mg, 78%) as a beige foam.

Intermediate I9

(2S,3S)-2-Methyl-N-(3,4,5-trifluorophenyl)pyrrolidine-3-carboxamide hydrochloride

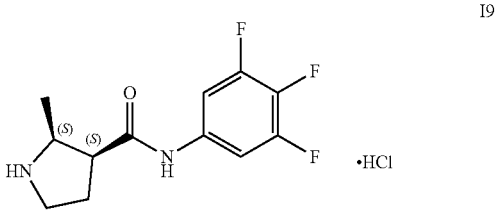

I9

The reaction was performed under anhydrous conditions and under Ar atmosphere.

To a solution of intermediate I8 (316 mg, 0.91 mmol) in DCM (3.5 mL) was added HCl (4N in 1,4-dioxane, 3.4 mL, 13.6 mmol). The reaction mixture was stirred at room temperature for 1 h, concentrated under reduced pressure and co-evaporated with DCM (2×5 mL) to afford intermediate I9 which was used as such in the next step.

Intermediate I10

Ethyl {(2S,3S)-2-methyl-3-[(3,4,5-trifluorophenyl)carbamoyl]pyrrolidin-1-yl}(oxo)acetate

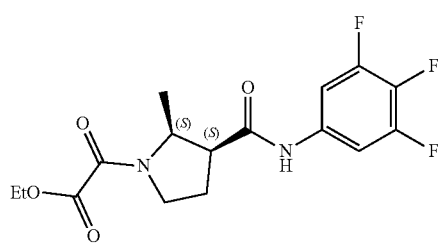

I10

The reaction was performed under anhydrous conditions and under Ar atmosphere.

To a solution of intermediate I9 (249 mg, 0.85 mmol) in DCM (5 mL) at 0° C. were successively added Et₃N (472 µL, 3.38 mmol) and ethyl chlorooxoacetate (142 µL, 1.27 mmol). The reaction mixture was warmed up to room temperature and stirred for 1.5 h. The reaction mixture was concentrated under reduced pressure and the residue was purified by flash column chromatography (silica, mobile phase: cyclohexane/EtOAc, gradient from 80:20 to 0:100). The residue was co-evaporated with Et₂O (5 mL) to afford intermediate I10 (275 mg, 91%) as a beige foam.

Intermediate I11

{(2S,3S)-3-[(3,4-Difluorophenyl)carbamoyl]-2-methylpyrrolidin-1-yl}(oxo)acetic acid

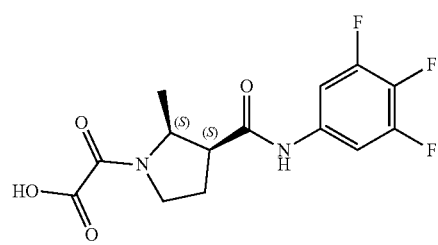

I11

Intermediate I10 (275 mg, 0.77 mmol) was dissolved in a mixture of MeOH (2 mL) and THF (2 mL). NaOH (1M in H₂O, 2.30 mL, 2.30 mmol) was added and the reaction mixture was stirred at room temperature for 1 h. The reaction mixture was concentrated to dryness and water (5 mL) was added. HCl (1N, aq.) was added until pH ~1 and the aqueous layer was extracted with EtOAc (2×5 mL). The combined organic layers were dried (Na₂SO₄), filtered and concentrated under reduced pressure to afford intermediate I11 which was used as such in the next step without any purification.

3.1.4. Synthesis of Intermediate I15

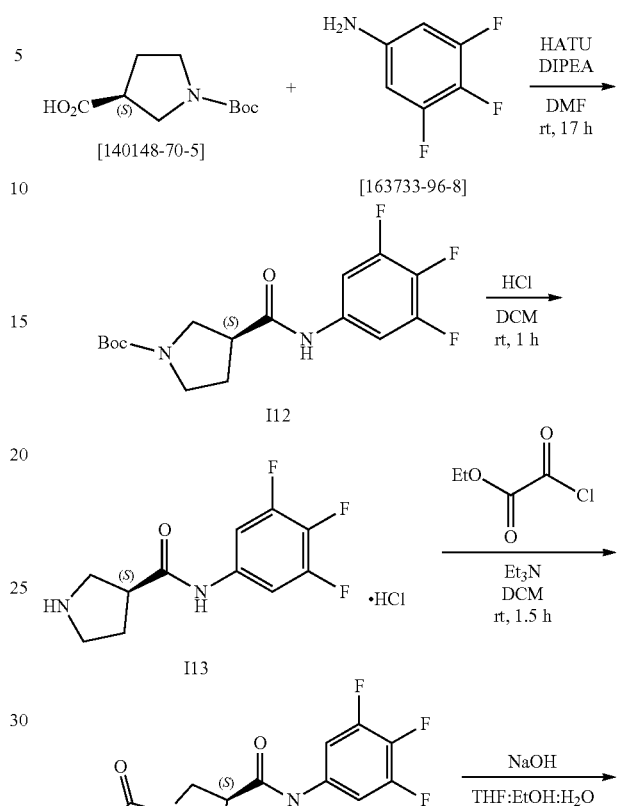

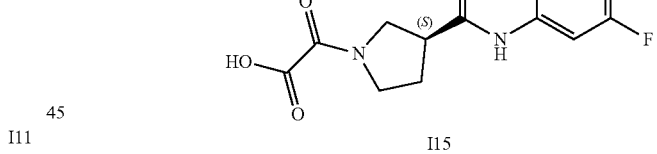

I15

Intermediate I12 tert-Butyl (3S)-3-[(3,4,5-trifluorophenyl)carbamoyl]pyrrolidine-1-carboxylate

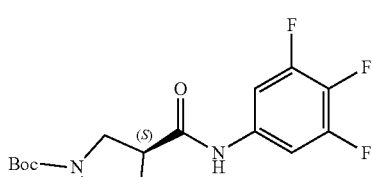

I12

Intermediate I12 was prepared similarly as described for the synthesis of intermediate I8.

The crude mixture was purified by flash column chromatography (silica, mobile phase: cyclohexane/EtOAc, gradient from 80:20 to 50:50) to give intermediate I12 (695 mg, 87%) as a beige solid.

Intermediate I13

(3-N-(3,4,5-Trifluorophenyl)pyrrolidine-3-carboxamide hydrochloride

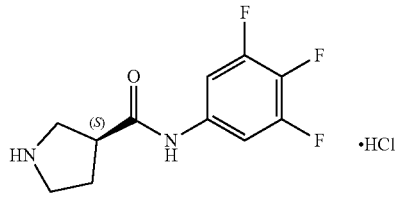

I13

Intermediate I13 was prepared similarly as described for the synthesis of intermediate I9.

Intermediate I14

Ethyl oxo{(3S)-3-[(3,4,5-trifluorophenyl)carbamoyl]pyrrolidin-1-yl}acetate

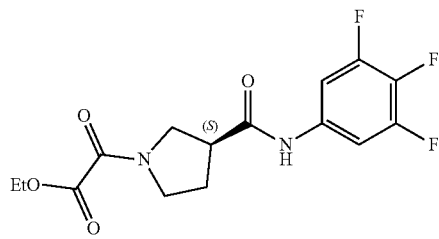

I14

Intermediate I14 was prepared similarly as described for the synthesis of intermediate I10.

The crude mixture was purified by flash column chromatography (silica, mobile phase: cyclohexane/EtOAc, gradient from 70:30 to 0:100). The residue was co-evaporated with Et₂O (5 mL) to afford intermediate I14 (585 mg, 86%) as a yellow solid.

Intermediate I15

Oxo{(3S)-3-[(3,4,5-trifluoro enyl)carbamoyl]pyrrolidin-1-yl}acetic acid

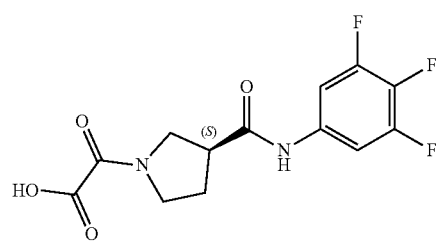

I15

Intermediate I15 was prepared similarly as described for the synthesis of intermediate I11 and used in the next step without any purification.

3.1.5. Synthesis of Intermediate I19

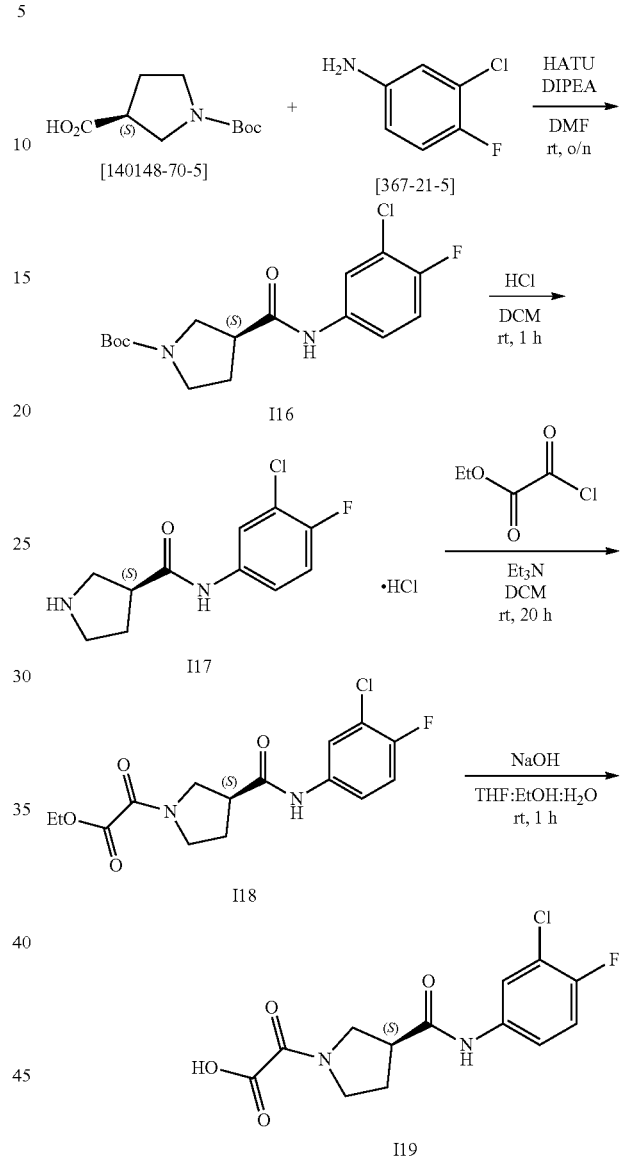

Intermediate I16 tert-Butyl (3S)-3-[(3-chloro-4-fluorophenyl)carbamoyl]pyrrolidine-1-carboxylate

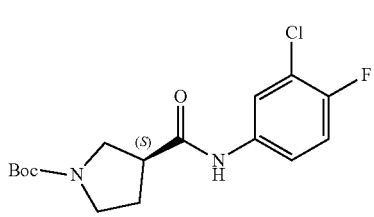

I16

Intermediate I16 was prepared similarly as described for the synthesis of intermediate I8.

The crude mixture was purified by flash column chromatography (silica, mobile phase: cyclohexane/EtOAc, gradient from 100:0 to 60:40). The residue was co-evaporated with DCM to afford intermediate I16 (1.2 g, quant.) as a beige foam.

Intermediate I17

(3S)—N-(3-Chloro-4-fluorophenyl)pyrrolidine-3-carboxamide hydrochloride

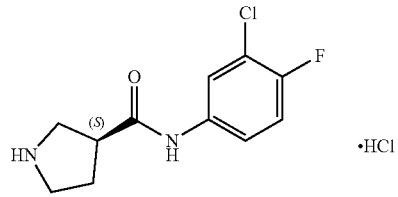

Intermediate I17 was prepared similarly as described for the synthesis of intermediate I9.

Intermediate I18

Ethyl {(3S)-3-[(3-chloro-4-fluorophenyl)carbamoyl]pyrrolidin-1-yl}(oxo)acetate

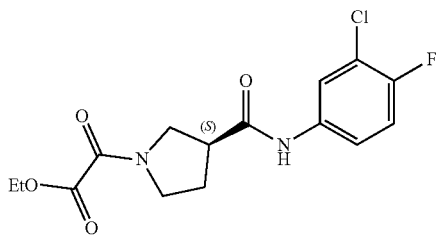

Intermediate I18 was prepared similarly as described for the synthesis of intermediate I10.

The crude mixture was purified by flash column chromatography (silica, mobile phase: cyclohexane/EtOAc, gradient from 50:50 to 0:100). The residue was co-evaporated with DCM to afford intermediate I18 (570 mg, 79%, 79% purity).

Intermediate I19

{(3S)-3-[(3-Chloro-4-fluorophenyl)carbamoyl]pyrrolidin-1-yl}(oxo)acetic acid

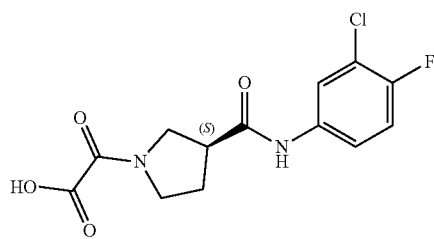

Intermediate I19 was prepared similarly as described for the synthesis of intermediate I11 and used in the next step without any purification.

3.1.6 Synthesis of Intermediate I23

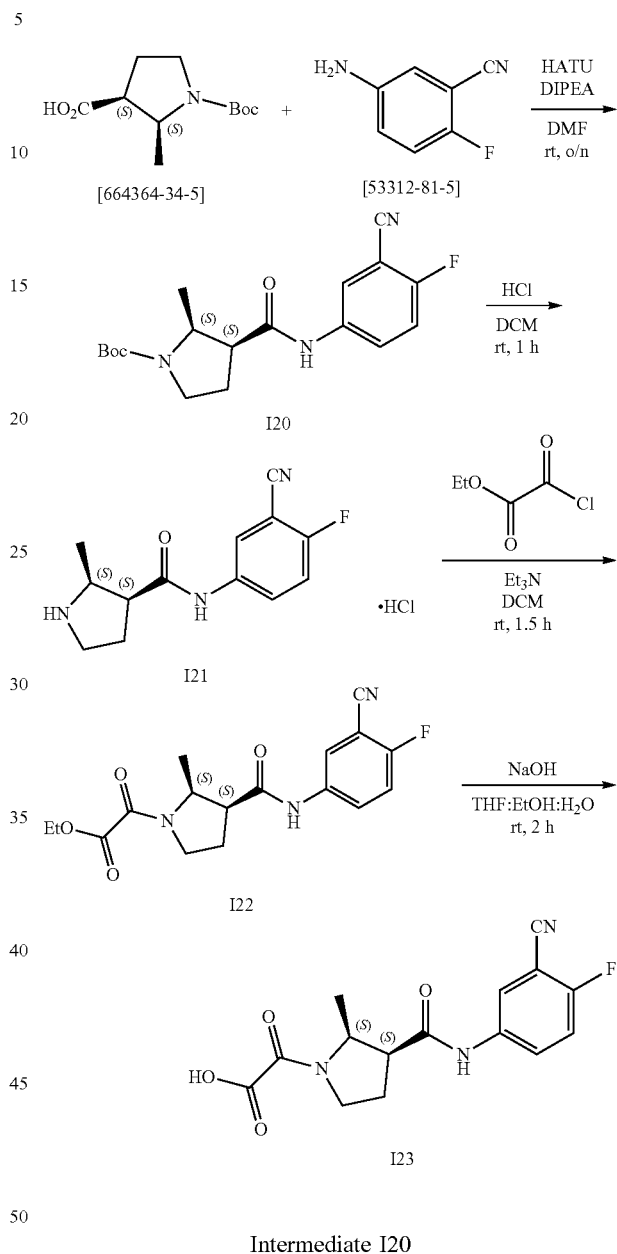

Intermediate I20 tert-Butyl (2S,3S)-3-[(3-cyano-4-fluorophenyl)carbamoyl]-2-methylpyrrolidine-1-carboxylate

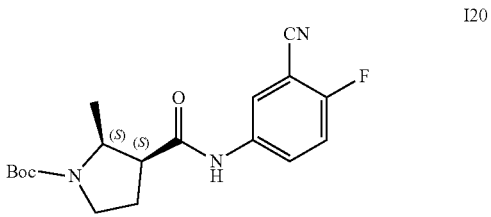

Intermediate I20 was prepared similarly as described for the synthesis of intermediate I8.

The crude mixture was purified by flash column chromatography (silica, mobile phase: cyclohexane/EtOAc, gradient from 90:10 to 50:50) to afford intermediate I20 (337 mg, 83%, 94% purity) as a beige foam.

Intermediate I21

(2S,3-N-3-Cyano-4-fluorophenyl)-2-methylpyrrolidine-3-carboxamide hydrochloride

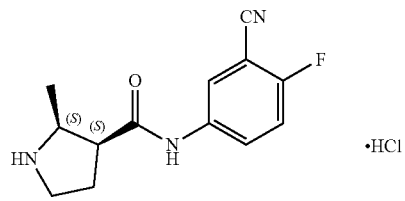

I21

Intermediate I21 was prepared similarly as described for the synthesis of intermediate I9.

Intermediate I22

Ethyl {(2S,3S)-3-[(3-cyano-4-fluorophenyl)carbamoyl]-2-methylpyrrolidin-1-yl}(oxo)acetate

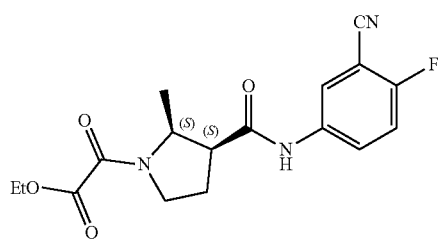

I22

Intermediate I22 was prepared similarly as described for the synthesis of intermediate I10.

The crude mixture was purified by flash column chromatography (silica, mobile phase: cyclohexane/EtOAc, gradient from 70:30 to 0:100). The residue was co-evaporated with Et₂O (5 mL) to afford intermediate I22 (288 mg, 91%).

Intermediate I23

{(2S,3S)-3-[(3-Cyano-4-fluorophenyl)carbamoyl]-2-methylpyrrolidin-1-yl}(oxo)acetic acid

I23

Intermediate I23 was prepared similarly as described for the synthesis of intermediate I11 and was used in the next step without any purification.

3.1.7. Synthesis of Intermediates I25-I28

Unless otherwise indicated, the intermediates below were synthesized in four reaction steps following the procedure reported for intermediate I11

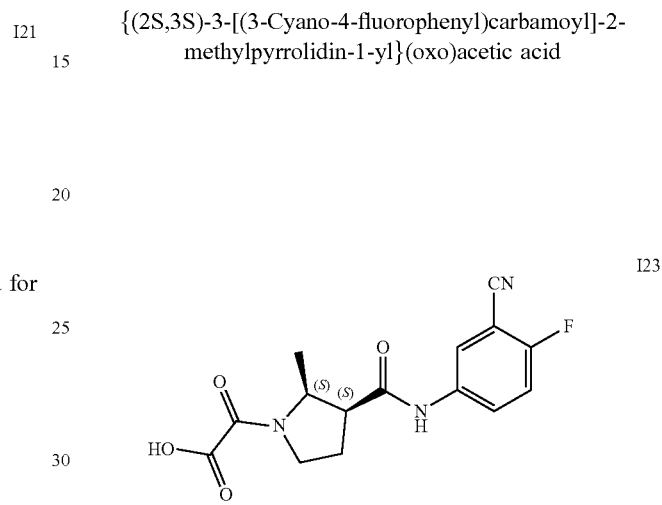

| Structure | Reagents step 1 | |
|---|---|---|
| I26 | [1393524-21-4] | [163733-96-8] |
| I27 | [140148-70-5] | [95-76-1] |

| Structure | Reagents step 1 |
|---|---|
| 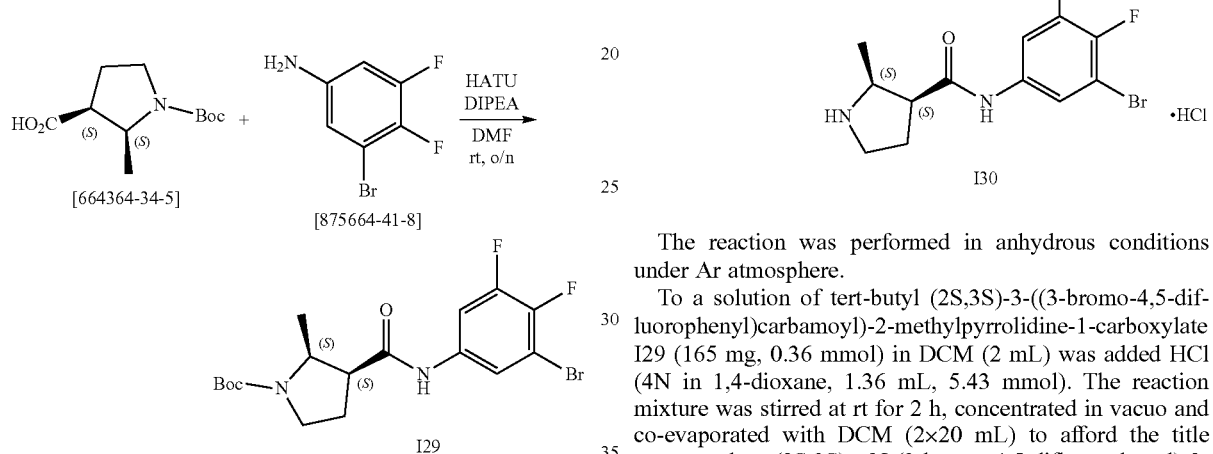 I28 | [140148-70-5]   [149144-05-8] |

3.1.8. Synthesis of Intermediate I30
Step 1

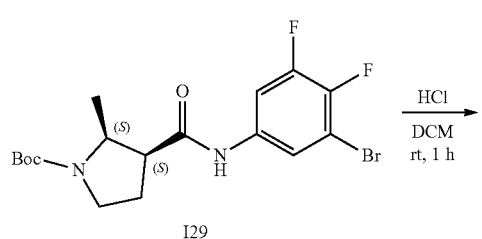

The reaction was performed in anhydrous conditions under Ar atmosphere

To a solution of (2S, 3S)-1-[(tert-butoxy)carbonyl]-2-methylpirrolidine-3-carboxylic acid (130 mg, 0.46 mmol) in DMF (3 mL) at rt were added 3-bromo-4,5-difluoroaniline (191 mg, 0.92 mmol), HATU (348 mg, 0.92 mmol) and DIPEA (0.24 mL, 1.37 mmol).

The reaction mixture was stirred at room temperature overnight and diluted with EtOAc (100 mL). The organic layer was separated and washed successively with NaHCO₃ (sat., aq., 2×50 mL), HCl (1M, aq., 2×50 mL) and brine (2×50 mL), dried (Na₂SO₄), filtered and concentrated to dryness. The crude was purified by flash chromatography (silica, mobile phase: cyclohexane/EtOAc, gradient from 90:10 to 50:50) to afford the tert-butyl (2S,3S)-3-((3-bromo-4,5-difluorophenyl)carbamoyl)-2-methylpyrrolidine-1-carboxylate I29 (165 mg, 78%) as a beige powder.

Step 2

The reaction was performed in anhydrous conditions under Ar atmosphere.

To a solution of tert-butyl (2S,3S)-3-((3-bromo-4,5-difluorophenyl)carbamoyl)-2-methylpyrrolidine-1-carboxylate I29 (165 mg, 0.36 mmol) in DCM (2 mL) was added HCl (4N in 1,4-dioxane, 1.36 mL, 5.43 mmol). The reaction mixture was stirred at rt for 2 h, concentrated in vacuo and co-evaporated with DCM (2×20 mL) to afford the title compound (2S,3S)—N-(3-bromo-4,5-difluorophenyl)-2-methylpyrrolidine-3-carboxamide hydrochloride I30 (146 mg, 100%, 88% purity) as a beige oil.

3.1.9. Synthesis of Intermediate I34
Step 1

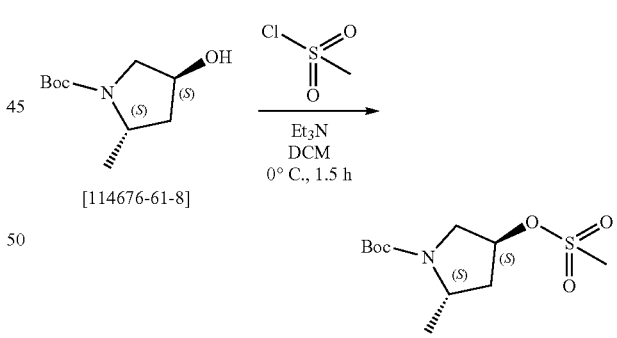

The reaction was performed in anhydrous conditions under Argon atmosphere.

To a solution of tert-butyl (2S,4S)-4-hydroxy-2-methylpyrrolidine-1-carboxylate (2 g, 9.94 mmol) in DCM (32 mL) cooled at 0° C. were added Et₃N (2.67 mL, 19.2 mmol) and methanesulfonyl chloride (1.11 mL, 14.4 mmol) and the reaction mixture was stirred at 0° C. for 1.5 h. Water (55 mL) was added and the aqueous layer was extracted with DCM (2×75 mL).

The combined organic layers were washed with HCl (1N, aq., 50 mL), NaHCO₃ (sat., aq., 50 mL), dried (Na₂SO₄), filtered and concentrated in vacuo. The residue was purified by flash chromatography (silica gel, mobile phase: cyclohexane/EtOAc, gradient from 80/20 to 40/60) to afford tert-butyl (2S,4S)-2-methyl-4-((methylsulfonyl)oxy)pyrrolidine-1-carboxylate I31 (1.97 g, 67%) as a colorless oil.

Step 2

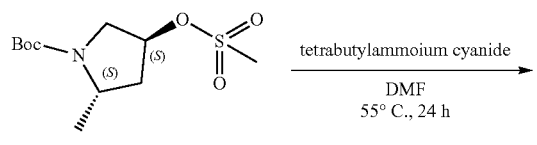

The reaction was performed in anhydrous conditions under Argon atmosphere.

To a solution of tert-butyl (2S,4S)-2-methyl-4-((methylsulfonyl)oxy)pyrrolidine-1-carboxylate I31 (1.33 g, 4.48 mmol) in DMF (13 mL) was added tetrabutylammonium cyanide (2.22 g, 8.28 mmol) and the reaction mixture was heated at 55° C. for 24 h.

Water (25 mL) was added and the aqueous layer was extracted with EtOAc (2×30 mL). The combined organic layers were washed with brine, dried (Na$_2$SO$_4$) filtered and concentrated in vacuo. The residue was purified by flash chromatography (silica, mobile phase: cyclohexane/EtOAc, gradient from 80/20 to 40/60) to afford tert-butyl (2S,4S)-4-cyano-2-methylpyrrolidine-1-carboxylate I32 (587 mg, 62%) as a colorless oil.

Step 3

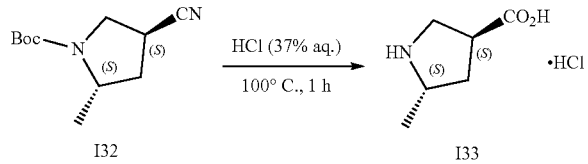

tert-Butyl (2S,4S)-4-cyano-2-methylpyrrolidine-1-carboxylate 32 (587 mg, 2.78 mmol) was dissolved in HCl (37% aq., 3 mL) and the reaction mixture was stirred at 100° C. for 1 h. The reaction mixture was concentrated and dried under vacuum during 6 h to afford (3S,5S)-1-(tert-butoxycarbonyl)-5-methylpyrrolidine-3-carboxylic acid hydrochloride I33 (580 g, 100%, 80% purity) as a beige solid which was used in the next step without further purification.

Step 4

The reaction was performed under Argon atmosphere.

To a solution of (3S,5S)-1-(tert-butoxycarbonyl)-5-methylpyrrolidine-3-carboxylic acid hydrochloride I33 (512 mg, 2.47 mmol) in a mixture of acetone (5.5 mL) and water (5.5 mL) cooled at 0° C. were added di-tert-butyl dicarbonate (742 mg, 0.34 mmol) and DIPEA (2.16 mL, 12.4 mmol) and the reaction mixture was stirred at rt for 4 h.

The reaction mixture was dissolved in water (15 mL) and EtOAc (15 mL). The aqueous layer was separated and acidified with HCl (3N, aq.) to pH ~1. The aqueous layer was extracted with EtOAc (2×30 mL). The combined organic layers were dried (Na$_2$SO$_4$), filtered, concentrated and co-evaporated with DCM (3×15 mL) to afford the title compound (3S,5S)-1-(tert-butoxycarbonyl)-5-methylpyrrolidine-3-carboxylic acid I34 (560 mg, 78%, 79% purity) as a colorless oil.

3.1.10. Synthesis of Intermediates I35-I40

Unless otherwise indicated, the intermediates below were synthesized in two reaction steps following the procedure reported for intermediate I30

| Structure | | Reagents step 1 | |
|---|---|---|---|
| ![I35 structure] •HCl | I35 | ![Boc acid] [664364-34-5] | ![aniline] [95-76-1] |
| ![I36 structure] •HCl | I36 | ![Boc acid] [664364-34-5] | ![aniline] [149144-05-8] |

-continued

| Structure | Reagents step 1 | |
|---|---|---|
| I37 ![structure with HCl, F, Cl] | Boc-N (S) pyrrolidine-COOH with methyl [664364-34-5] | H2N-phenyl-F, Cl [367-21-5] |
| I38 ![structure with HCl, F, CN] | Boc-N (S) pyrrolidine-COOH [134] | H2N-phenyl-F, CN [53312-81-5] |
| I39 ![structure with HCl, 3F] | Boc-N (S) pyrrolidine-COOH [134] | H2N-phenyl-3F [163733-96-8] |
| I40 ![structure with HCl, 3F, R-methyl] | Cbz-N (S) pyrrolidine-COOH (R)-methyl [1428243-71-3] | H2N-phenyl-3F [163733-96-8] |

*Step 1: Propylphosphonic anhydride (PPACA) was used instead of HATU
**Step 2: another method was used: The reaction was performed in anhydrous conditions under H₂ atmosphere (atmospheric pressure). Benzyl (3R,4S)-3-methyl-4-((3,4,5-trifluorophenyl)carbamoyl)pyrrolidine-1-carboxylate (219 mg, 0.39 mmol) in MeOH (15 ml) was purged with argon, then Pd/C (10%, 21 mg, 0.02 mmol) was added and the mixture was purged with H₂. The reaction was stirred at room temperature for 16 h under H₂. Then, the catalyst was filtered off on HyfloSuperCel, the filter cake was rinsed with EtOAc (30 ml) and the filtrate was concentrated under reduced pressure then co-evaporated with HCl (4N in 1,4-dioxane, 7 mL) affording (3S,4R)-4-methyl-N-(3,4,5-trifluorophenyl)pyrrolidine-3-carboxamide hydrochloride 40 as a colorless oil which was used in the next step without further purification.

3.1.11. Synthesis of Intermediate I43
Step 1

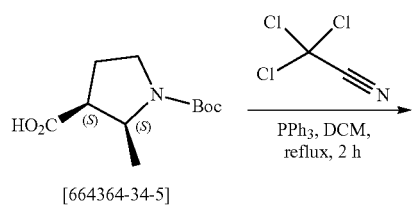

-continued

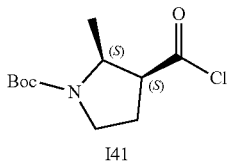

I41

The reaction was performed in anhydrous conditions under Ar atmosphere.

To a solution of (2S, 3S)-1-[(tert-butoxy)carbonyl]-2-methylpirrolidine-3-carboxylic acid (130 mg, 0.46 mmol) in DCM (3 mL) at rt were added trichloroacetonitrile (0.09 mL, 0.92 mmol) and triphenylphosphine (240 mg, 0.912 mmol); weak exothermic reaction. The reaction mixture was stirred at reflux for 2 hours to afford tert-butyl (2S, 3S)-3-(chlorocarbonyl)-2-methylpyrrolidine-1-carboxylate 41 (113 mg, quant.) which was used as such in the next reaction step.

Step 2

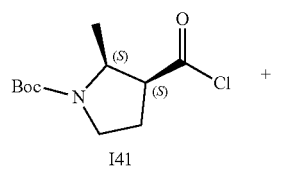

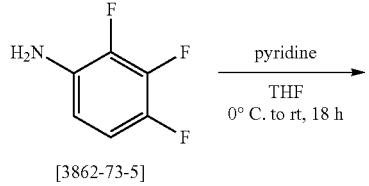

The reaction was performed in anhydrous conditions under Ar atmosphere

To a solution of 2,3,4-trifluoroaniline (0.04 mL, 0.43 mmol) in THF (2 mL) cooled down to 0° C., was added pyridine (0.10 mL, 1.28 mmol). To this solution was added dropwise at 0° C. intermediate tert-butyl (2S, 3S)-3-(chlorocarbonyl)-2-methylpyrrolidine-1-carboxylate I41 (113 mg, 0.46 mmol), previously cooled at 0° C.; exothermic reaction with gas evolution. The resulting mixture was left to stir at rt for 18 h. The reaction mixture was concentrated in vacuo. The crude was purified by flash chromatography (silica, mobile phase: cyclohexane/EtOAc, gradient from 100 to 70:30) to afford tert-butyl (2S,3S)-2-methyl-3-((2,3,4-trifluorophenyl)carbamoyl)pyrrolidine-1-carboxylate I42 (165 mg, 99%) as an orange oil.

Step 3

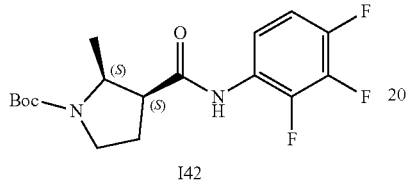

The reaction was performed in anhydrous conditions under Ar

To a solution of tert-butyl (2S,3S)-2-methyl-3-((2,3,4-trifluorophenyl)carbamoyl)pyrrolidine-1-carboxylate (165 mg, 0.42 mmol) in DCM (6 mL) was added HC (4N in 1,4-dioxane, 1.59 mL, 6.35 mmol). The reaction mixture was stirred at rt for 1 h, concentrated in vacuo and co-evaporated with DCM (3×15 mL) to afford the title compound (2S,3S)-2-methyl-N-(2,3,4-trifluorophenyl)pyrrolidine-3-carboxamide hydrochloride 43 (132 mg, 98%) as a beige powder.

3.1.12. Synthesis of Intermediate I51

Step 1

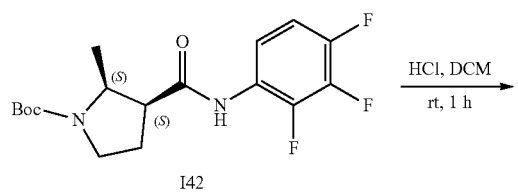

The reaction was performed in anhydrous conditions under Ar atmosphere.

To a solution of benzyl acetoacetate (30 mL, 174 mmol) and DBU (26.0 mL, 174 mmol) in toluene (350 mL) was added at rt a solution of allyl bromide (15 mL, 174 mmol) in toluene (170 mL) and the reaction mixture was stirred at rt for 18 h. The reaction mixture was filtered and rinsed with toluene (150 mL). The filtrate was washed with water (250 mL), brine (250 mL), dried (Na$_2$SO$_4$), filtered and concentrated in vacuo. The residue was purified by chromatography (silica, mobile phase: cyclohexane/EtOAc, gradient from 95/5 to 90/10) to afford (rac)-benzyl 2-acetylpent-4-enoate I44 (23.2 g, 57%) as a colorless liquid.

Step 2

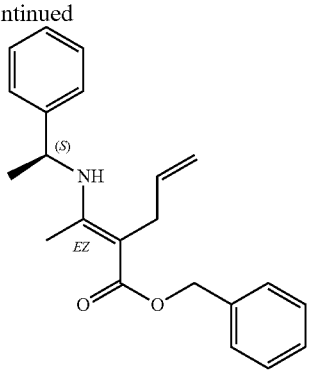

I45

The reaction was performed in anhydrous conditions under Ar atmosphere

To a solution of (rac)-benzyl 2-acetylpent-4-enoate I44 (22.8 g, 98.2 mmol) and AcOH (5.62 mL, 98.2 mmol) in toluene (350 mL) at rt was added (S)-(−)-1-phenylethylamine (25.3 mL, 1% mmol) and the reaction mixture was heated to 135° C. for 24 h using a Dean-Stark. The reaction mixture was concentrated in vacuo. The residue was taken up in Et₂O (100 mL) and sonicated. The precipitate was removed by filtration then the filtrate was concentrated, taken up in Et₂O (40 mL) and sonicated. The resulting solid was removed by filtration. The filtrate was concentrated and dried under vacuum to give benzyl (S)-2-(1-((1-phenylethyl) amino)ethylidene)pent-4-enoate 145 (41.8 g, 99%, 79% purity) as a yellow oil which was used in the next step without further purification.

Step 3

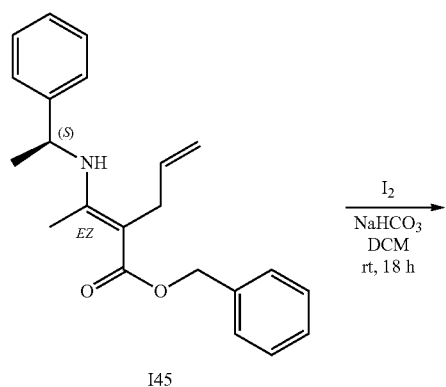

I45

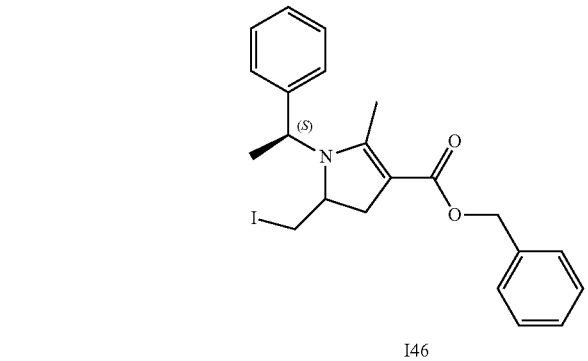

I46

The reaction was performed in anhydrous conditions under Ar atmosphere

To a solution of benzyl (S)-2-(1-((1-phenylethyl)amino) ethylidene)pent-4-enoate I45 (41.7 g, 97.8 mmol) in DCM (800 mL) at rt were added NaHCO₃ (9.86 g, 117 mmol) then I2 (29.8 g, 117 mmol) and the reaction mixture was stirred at rt for 18 h.

The reaction mixture was washed with Na₂S₂O₃ (M, aq., 2×500 mL), brine (500 mL), dried (Na₂SO₄), filtered and concentrated in vacuo. The residue was purified by chromatography (silica, mobile phase: cyclohexane/EtOAc, gradient from 95/5 to 85/15) to give benzyl 5-(iodomethyl)-2-methyl-1-((S)-1-phenylethyl)-4,5-dihydro-1H-pyrrole-3-carboxylate I46 (30.3 g, 67%) as a pale yellow oil.

Step 4

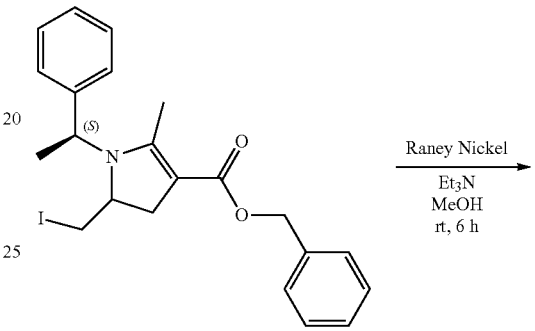

I46

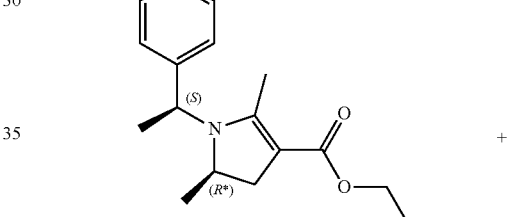

I47*R

+

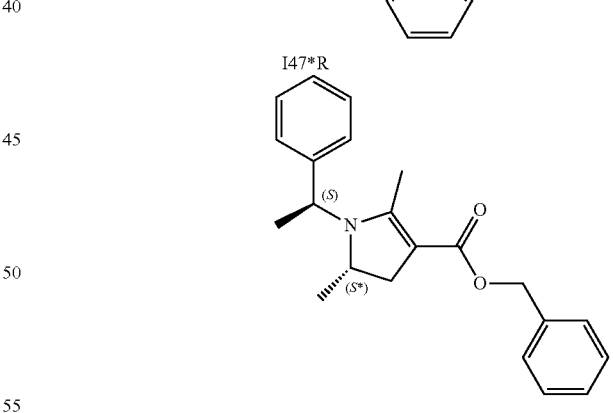

I47*S

The reaction was performed under hydrogen atmosphere

To a solution of benzyl 5-(iodomethyl)-2-methyl-1-((S)-1-phenylethyl)-4,5-dihydro-1H-pyrrole-3-carboxylate 46 (10 g, 21.7 mmol) in MeOH (150 mL) at rt was added Et₃N (6.04 mL, 43.4 mmol). The reaction mixture was purged and backfilled with argon twice then a slurry of Raney Nickel (about 1 g, suspension in water) was added.

The reaction mixture was purged and backfilled with argon twice then purged and backfilled with hydrogen and stirred at rt for 6 h. The catalyst was filtered through a pad of Celite® and rinsed with MeOH (50 mL) and the filtrate was concentrated in vacuo. The residue was suspended in EtOAc (200 mL) and the resulting solid (Et₃N.HCl) was removed by filtration. The filtrate was concentrated in vacuo. The crude mixture was purified by chromatography (silica, dry load, mobile phase: cyclohexane/EtOAc, gradient from 100/0 to 85/15). The residue was dried under vacuum (9×10−2 mbar, rt) during 24 h to give benzyl 2,5-dimethyl-1-((S)-1-phenylethyl)-4,5-dihydro-1H-pyrrole-3-carboxylate I47R*/I47S* (6 g, 83%) as a mixture of diastereoisomers, which was separated into the corresponding enantiomers by SFC (Stationary phase: Chiralpak Daicel IC 20×250 mm, Mobile phase: CO₂, EtOH+0.4 iPrNH₂) yielding benzyl (R*)-2,5-dimethyl-1-((S)-1-phenylethyl)-4,5-dihydro-1H-pyrrole-3-carboxylate I47R* and benzyl (S*)-2,5-dimethyl-1-((S)-1-phenylethyl)-4,5-dihydro-1H-pyrrole-3-carboxylate I47S*.

Step 5

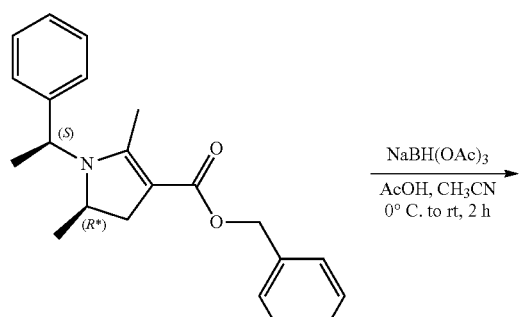

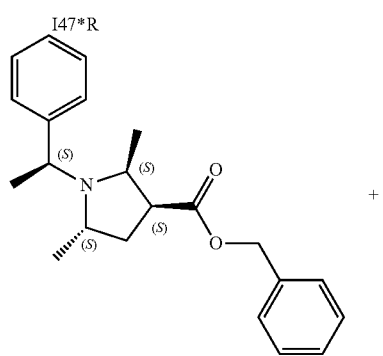

The reaction was performed in anhydrous conditions under argon atmosphere AcOH (1.49 mL, 25.9 mmol) was added to a solution of benzyl (R*)-2,5-dimethyl-1-((S)-1-phenylethyl)-4,5-dihydro-1H-pyrrole-3-carboxylate I47R* (2.90 g, 8.65 mmol) in CH₃CN (40 mL) at room temperature. The reaction mixture was cooled to 0° C. and sodium triacetoxyborohydride (4.58 g, 21.6 mmol) was added portion wise, over 10 min. The reaction mixture was stirred at 0° C. for 3 hours, then at room temperature for 2 hours. The crude (containing a mixture of two diastereoisomers) was purified by flash chromatography (silica, mobile phase: cyclohexane/EtOAc, gradient from 10/0 to 0/100) yielding three fractions: a first fraction of the desired benzyl (2S,3S,5S)-2,5-dimethyl-1-((S)-1-phenylethyl)pyrrolidine-3-carboxylate (705 mg, 22%); a second fraction of the same compound which was again purified by flash chromatography (silica, mobile phase: cyclohexane/EtOAc, gradient 10/0 to 90/10) to afford benzyl (2S,3S,5S)-2,5-dimethyl-1-((S)-1-phenylethyl)pyrrolidine-3-carboxylate I48 (578 mg, 20%); a third impure fraction of benzyl (2R,3R,5S)-2,5-dimethyl-1-((S)-1-phenylethyl)pyrrolidine-3-carboxylate I49 (1.2 g).

Note: Structure resolution was realized by 2D NMR analyses.

Step 6

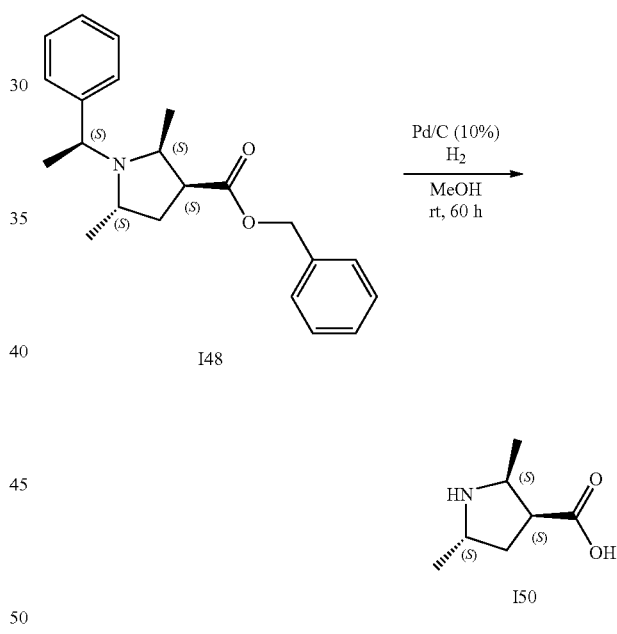

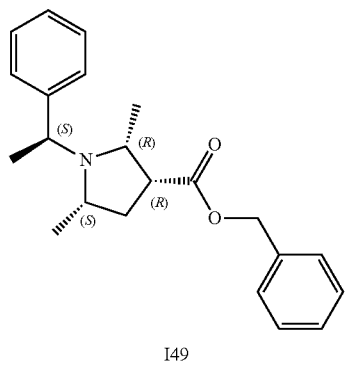

The reaction was performed in anhydrous conditions under hydrogen atmosphere

A solution of benzyl (2S,3S,5S)-2,5-dimethyl-1-((S)-1-phenylethyl)pyrrolidine-3-carboxylate I48 (705 mg, 1.89 mmol) in MeOH (2 mL) was purged and backfilled with nitrogen, then Pd/C (10%, 70 mg, 0.07 mmol) was added at room temperature. The reaction mixture was purged and backfilled with nitrogen, then purged and backfilled with hydrogen and stirred at room temperature for 60 h under hydrogen atmosphere. The catalyst was filtered through a pad of Celite® and rinsed with MeOH (70 mL). The filtrate was concentrated to afford (2S,3S,5S)-2,5-dimethylpyrrolidine-3-carboxylic acid I50 (428 mg, 100%, 63% purity) as a yellow solid, which was used in the next step without further purification.

Step 7

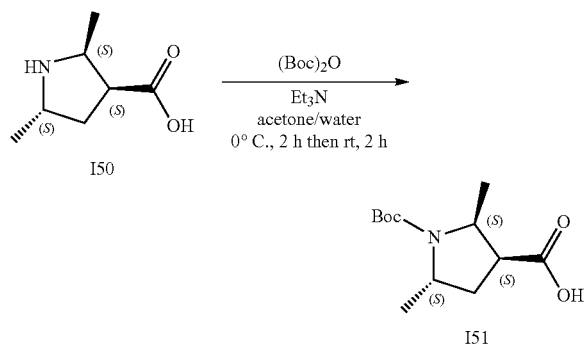

The reaction was performed under argon atmosphere

To a solution of (2S,3S,5S)-2,5-dimethylpyrrolidine-3-carboxylic acid I50 (314 mg, 2.19 mmol) in acetone (2 mL) and water (2 mL) at 0° C., were successfully added Et₃N (0.92 mL, 6.58 mmol) and di-tert-butyl dicarbonate (574 mg, 2.63 mmol). The resulting reaction mixture was stirred at 0° C. for 2 h. The mixture was warmed to room temperature and stirred for 2 h. Water (20 mL) and EtOAc (20 mL) were added and the layers was separated. The aqueous layer was acidified with HCl (3N, aq.) until pH=1, then extracted with EtOAc (3×50 mL). The combined organic layers were dried (Na₂SO₄), filtered and concentrated to afford (2S,3S,5S)-1-(tert-butoxycarbonyl)-2,5-dimethylpyrrolidine-3-carboxylic acid I51 (565 mg, 98%) as a beige oil, which was used in the next step without further purification 3.1.13. Synthesis of Intermediates I52-I60

Unless otherwise indicated, the intermediates below were synthesized in three reaction steps following the procedure reported for intermediate I43

| Structure | Reagent step 1 | Reagent step 2 |
|---|---|---|
| I57 | [664364-34-5] | [2357-47-3] |
| I58 | I51 | [163733-96-8] |
| I59 | [140148-70-5] | [14432-12-3] |
| I60 | [140148-70-5] | [1446509-58-5] |

*Step 2: DIPEA and DCM were used instead of pyridine and THF 3.1.14. Synthesis of Intermediate I64
Step 1

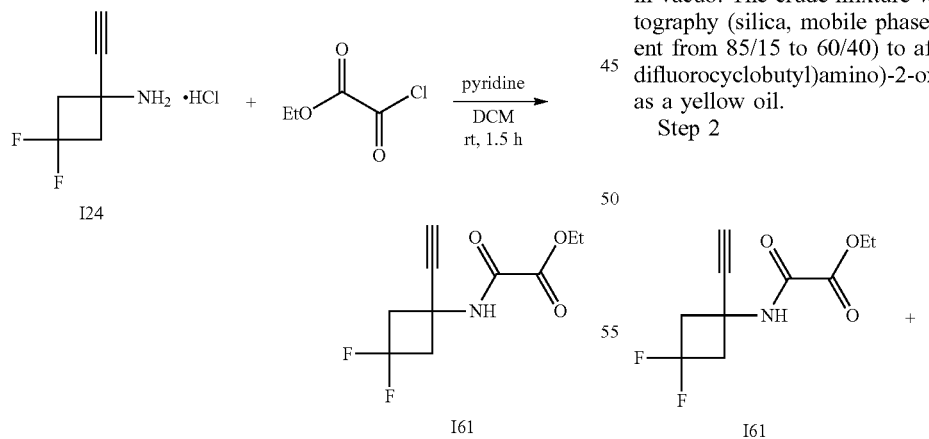

The reaction was performed in anhydrous conditions under Argon

To a solution of intermediate I24 (1.98 g, 10.81 mmol) in DCM (40 mL) cooled to 0° C. were added pyridine (2.18 mL, 27.03 mmol) then ethyloxalyl chloride (1.45 mL, 12.97 mmol) and the reaction mixture was stirred at rt for 1.5 h. The reaction mixture was quenched with NaHCO₃ (sat., aq., 40 mL). The aqueous layer was extracted with DCM (2×40 mL). The combined organic layers were washed with HCl (1N, aq., 40 mL), dried (Na₂SO₄), filtered and concentrated in vacuo. The crude mixture was purified by flash chromatography (silica, mobile phase: cyclohexane/EtOAc, gradient from 85/15 to 60/40) to afford ethyl 2-((1-ethynyl-3,3-difluorocyclobutyl)amino)-2-oxoacetate I61 (1.65 g, 65%) as a yellow oil.

Step 2

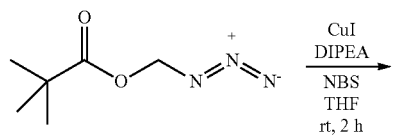

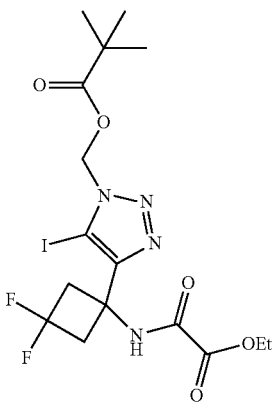

I62

The reaction was performed in anhydrous conditions under Argon

To a solution of ethyl 2-((1-ethynyl-3,3-difluorocyclobutyl)amino)-2-oxoacetate (365 mg, 1.56 mmol) in THF (18 mL) were added azidomethyl pivalate (0.26 mL, 1.71 mmol), copper iodide (1.19 g, 6.23 mmol), DIPEA (1.09 mL, 6.23 mmol) and NBS (1.11 g, 6.23 mmol) and the reaction mixture was stirred at rt for 2 h. The reaction mixture was diluted in water (30 mL). The aqueous layer was extracted with EtOAc (4×40 mL). The combined organic layers were dried (Na$_2$SO$_4$), filtered and concentrated in vacuo. The crude mixture was purified by flash chromatography (silica, mobile phase: DCM/MeOH, gradient from 100/0 to 95/5) to afford (4-(1-(2-ethoxy-2-oxoacetamido)-3,3-difluorocyclobutyl)-5-iodo-1H-1,2,3-triazol-1-yl)methyl pivalate I62 (700 mg, 87%) as a brown solid.

Step 3

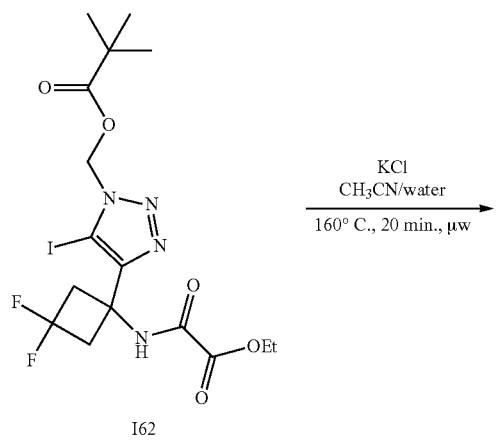

I62

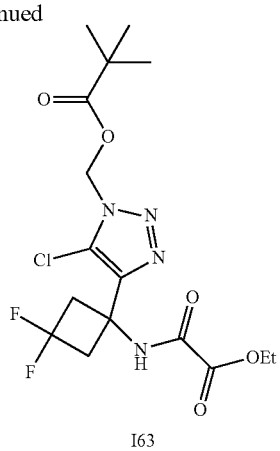

I63

The reaction was performed under Argon atmosphere

To a solution of (4-(1-(2-ethoxy-2-oxoacetamido)-3,3-difluorocyclobutyl)-5-iodo-1H-1,2,3-triazol-1-yl)methyl pivalate I62 (418 mg, 0.811 mmol) in a mixture of CH$_3$CN (4 mL) and water (4 mL) was added potassium chloride (302 mg, 4.06 mmol). The reaction mixture was stirred for 30 minutes at 160° C. under microwave irradiation (biotage initiator EXP60 system). The reaction mixture was diluted with water (50 mL). The aqueous layer was extracted with EtOAc (3×50 mL). The combined organic layers were dried (Na$_2$SO$_4$), filtered and concentrated in vacuo. The crude mixture was purified by flash chromatography (silica, mobile phase: DCM/MeOH, gradient from 100/0 to 97/3) to afford (5-chloro-4-(1-(2-ethoxy-2-oxoacetamido)-3,3-difluorocyclobutyl)-1H-1,2,3-triazol-1-yl)methyl pivalate 63 (147 mg, 43%) as a yellow oil.

Step 4

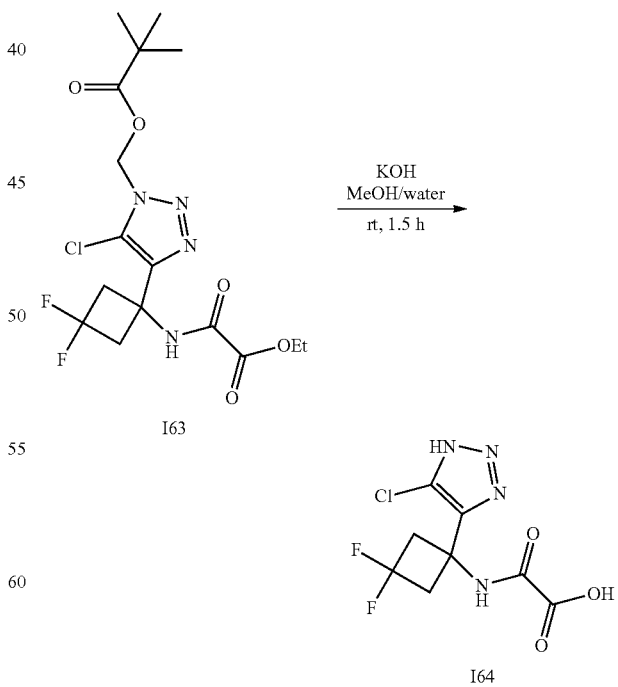

To a solution of (5-chloro-4-(1-(2-ethoxy-2-oxoacetamido)-3,3-difluorocyclobutyl)-1H-1,2,3-triazol-1-yl)

methyl pivalate 63 (290 mg, 0.65 mmol) in a mixture of water (2 mL) and MeOH (4 mL) was added potassium hydroxide (181 mg, 3.23 mmol) and the reaction mixture was stirred at rt for 1.5 h. Then methanol was removed and water was added (15 mL). The aqueous layer was washed with EtOAc (15 mL) and acidified with HCl (1N, aq.) until pH~1. The aqueous layer was extracted with EtOAc (3×30 mL). The combined organic layers were dried (Na₂SO₄), filtered and concentrated in vacuo. The residue was co-evaporated with cyclohexane (3×5 mL) to yield 2-((1-(5-chloro-1H-1,2,3-triazol-4-yl)-3,3-difluorocyclobutyl)amino)-2-oxoacetic acid I64 (175 mg, 81%, 84% purity) which was used in the next reaction step without further purification.

Synthesis of Intermediate I69

Step 1

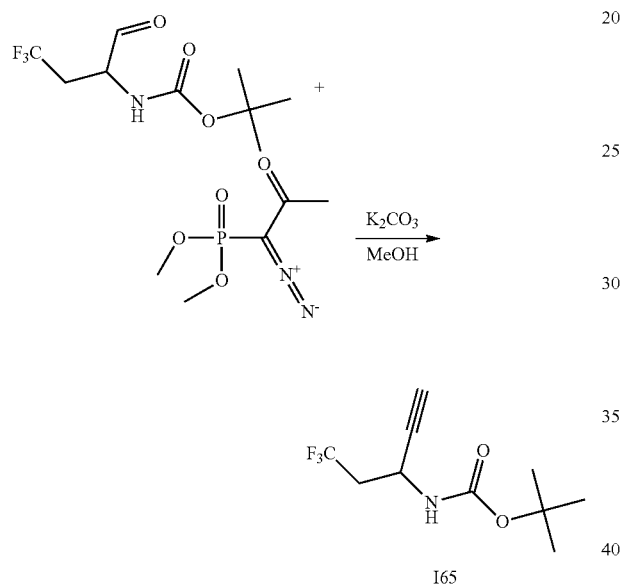

Dimethyl (1-diazo-2-oxopropyl)phosphonate (0.62 mL, 4.15 mmol) was added to a suspension of tert-butyl (4,4,4-trifluoro-1-oxobutan-2-yl)carbamate (1 g, 4.15 mmol) and K₂CO₃ (145 mg, 8.29 mmol) in MeOH at 0° C. After 30 minutes the reaction mixture was warmed to room temperature and stirring was continued overnight. The reaction mixture was evaporated to dryness. The residue was partitioned between diethyl ether (5 mL) and water (5 mL). The organic layer was dried over Na₂SO₄, filtered and evaporated to dryness. The residue was used as such in the next step.

Step 2

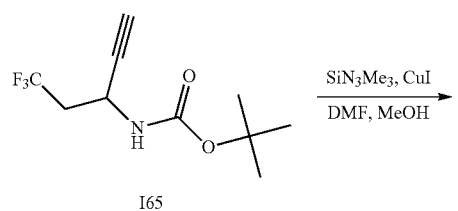

-continued

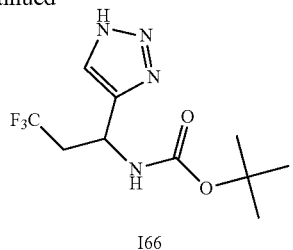

Tert-butyl (5,5,5-trifluoropent-1-yn-3-yl)carbamate I65 (0.75 g, 3.16 mmol), azidotrimethylsilane (1.23 mL, 8.85 mmol) and copper iodide (30.11 mg, 0.16 mmol) were dispensed in DMF (5 mL) and MeOH (0.5 mL) and heated 5 hours at 100° C. The volatiles were removed under reduced pressure and the residue was purified on silica using a heptane to EtOAc gradient yielding to tert-butyl (3,3,3-trifluoro-1-(2H-1,2,3-triazol-4-yl)propyl)carbamate I66 (490 mg, 55% yield) as a white powder.

Step 3

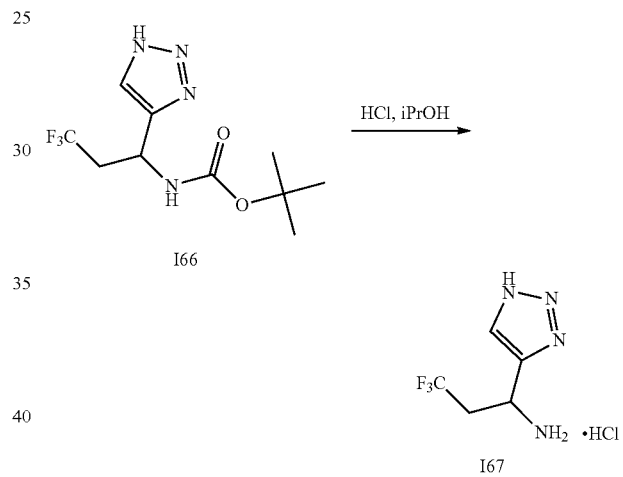

Tert-butyl (3,3,3-trifluoro-1-(2H-1,2,3-triazol-4-yl)propyl)carbamate I66 (3.47 g, 12.38 mmol) was dissolved in HCl (6M in iPrOH, 33 mL, 198.11 mmol) and stirred at rt for 2 h. The volatiles were removed under reduced pressure and the residue was co-evaporated with DIPE (3×50 mL). The residue was triturated with DIPE (60 mL) for 15 minutes. The suspension was filtered and the residue was dried in vacuo at 50° C. overnight yielding 3,3,3-trifluoro-1-(1H-1,2,3-triazol-4-yl)propan-1-amine hydrochloride I67 (2.44 g, 91% yield) as a pale green powder.

Step 4

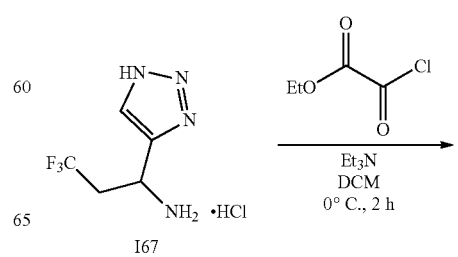

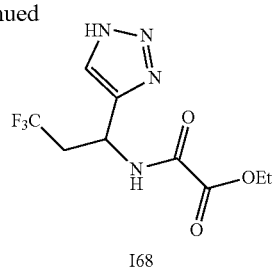

Synthesis of Intermediate I71
Step 1

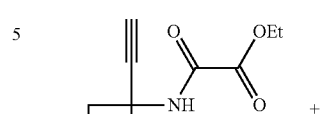

The reaction was performed in anhydrous conditions under argon atmosphere

To a solution of 3,3,3-trifluoro-1-(1H-1,2,3-triazol-4-yl)propan-1-amine hydrochloride I67 (400 mg, 1.85 mmol) in DCM (13 mL) at 0° C. were added Et₃N (772 µL, 5.54 mmol) and ethyl oxalyl chloride (217 µL, 1.94 mmol). The reaction was stirred for 2 h at 0° C. The reaction mixture was quenched with water (100 mL) and extracted with EtOAc (2×100 mL). Combined organic layers were washed with HCl (1N, aq., 100 mL), NaHCO₃ (sat., aq., 100 mL), brine (100 mL), dried (Na₂SO₄), filtered and concentrated to afford ethyl 2-oxo-2-((3,3,3-trifluoro-1-(1H-1,2,3-triazol-4-yl)propyl)amino)acetate I68 (555 mg, 90%, 84% purity) as a white solid which was used as such in the next step.

Step 5

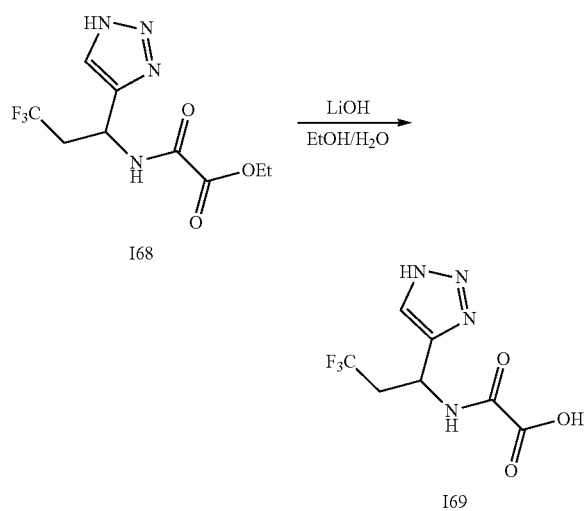

The reaction was performed under argon atmosphere

To a solution of ethyl 2-oxo-2-((3,3,3-trifluoro-1-(1H-1,2,3-triazol-4-yl)propyl)amino)acetate I68 (520 mg, 1.86 mmol) in a mixture of EtOH (5 mL) and H₂O (5 mL) at 0° C. was added lithium hydroxide (89.0 mg, 3.71 mmol). The reaction was stirred overnight allowing the ice bath to reach to room temperature. Additional lithium hydroxide (44.3 mg, 1.86 mmol) was added and the reaction was stirred for 4 h at room temperature. The reaction mixture was diluted with water (30 mL), acidified with HCl (3N, aq.) until pH ~1 and extracted with EtOAc (3×100 mL). Combined organic layers were washed with brine, dried (Na₂SO₄), filtered and concentrated to afford 2-oxo-2-((3,3,3-trifluoro-1-(1H-1,2,3-triazol-4-yl)propyl)amino)acetic acid I69 (511 mg, 95%, 87% purity) as a white solid which was used as such in the next step.

The reaction was performed in anhydrous conditions under argon atmosphere

To a solution of intermediate ethyl 2-((1-ethynyl-3,3-difluorocyclobutyl)amino)-2-oxoacetate I61 (1.64 g, 4.75 mmol) in a mixture of DMF (4 mL) and EtOH (0.4 mL) were added azidotrimethylsilane (0.94 mL, 7.14 mmol) and copper iodine (45 mg, 0.24 mmol) at room temperature. The reaction mixture was sealed into a microwave reaction vial and heated at 100° C. for 11 hours. The mixture was cooled down to room temperature then diluted with EtOAc (300 mL). The organic layer was washed with brine (2×80 mL), dried (Na₂SO₄), filtered and concentrated in vacuo. The crude mixture was purified by flash chromatography (silica, mobile phase: DCM/MeOH, gradient from 100:0 to 98:2) to afford ethyl 2-((3,3-difluoro-1-(1H-1,2,3-triazol-4-yl)cyclobutyl)amino)-2-oxoacetate I70 (984 mg, 76%) as a white powder.

Step 2

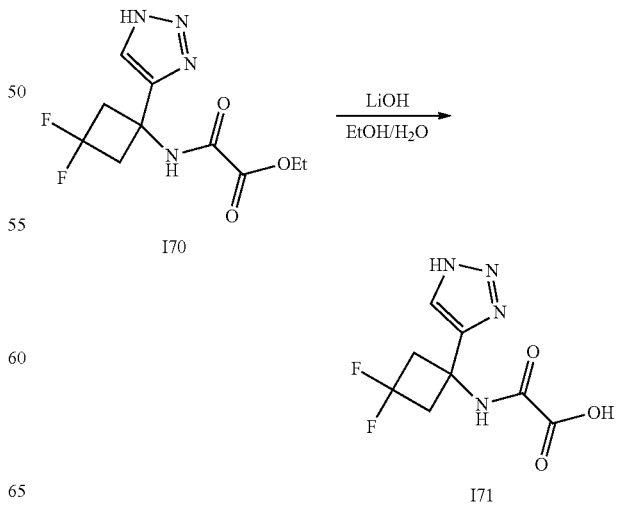

Intermediate 2-((3,3-difluoro-1-(1H-1,2,3-triazol-4-yl)cyclobutyl)amino)-2-oxoacetic acid I71 was synthesized according to the procedure reported for intermediate I69 from ethyl 2-((3,3-difluoro-1-(1H-1,2,3-triazol-4-yl)cyclobutyl)amino)-2-oxoacetate.

3.1.15. Synthesis of Intermediate I78

Step 1

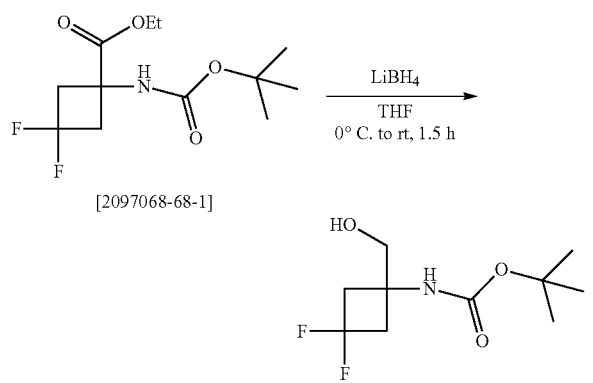

The reaction was performed in anhydrous conditions under Argon atmosphere

To a solution of methyl 1-([(tert-butoxy)carbonyl]amino)-3,3-difluorocyclobutane-1-carboxylate (20.0 g, 75.4 mmol) in THF (200 mL) cooled to 0° C. was added LiBH₄ (4M in THF, 75.4 mL, 301.6 mmol) dropwise. The mixture was stirred at 0° C. for 20 min, then at rt for 1.5 h. The mixture was cooled to ~15° C. and citric acid (M, aq., 150 mL) was added very slowly. Water (150 mL) was added and the aqueous layer was extracted with DCM (3×200 mL). The combined organic layers were dried (Na₂SO₄), filtered and concentrated to afford tert-butyl (3,3-difluoro-1-(hydroxymethyl)cyclobutyl)carbamate I72 (19.57 g, quant.) as a white solid which was used as such in the next reaction step.

Step 2

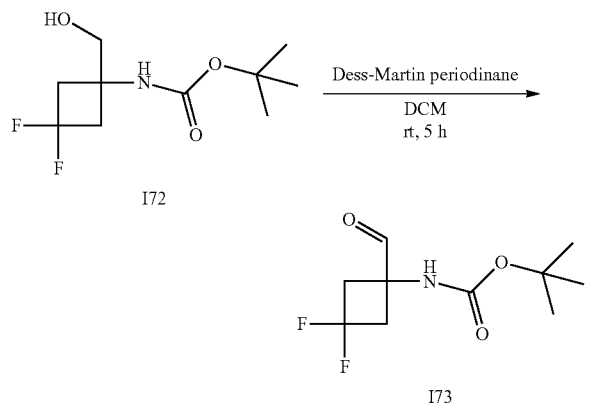

The reaction was performed in anhydrous conditions, under Argon atmosphere

To a solution of tert-butyl (3,3-difluoro-1-(hydroxymethyl)cyclobutyl)carbamate I72 (19.6 g, 75.4 mmol) in DCM (150 mL) was added Dess-Martin periodinane (48.0 g, 113 mmol) and the reaction mixture was stirred at rt for 5 h. Na₂S₂O₃ (M, aq., 400 mL), then NaHCO₃ (sat., aq., 200 mL) were added. The aqueous layer was extracted with DCM (3×300 mL). The combined organic layers were washed with NaHCO₃ (sat., aq., 200 mL), brine, dried (Na₂SO₄), filtered and concentrated in vacuo. The residue was purified by flash chromatography (silica, mobile phase: cyclohexane/EtOAc, gradient from 100/0 to 75/25) to give tert-butyl (3,3-difluoro-1-formylcyclobutyl)carbamate I73 (7.55 g, 41%).

Step 3

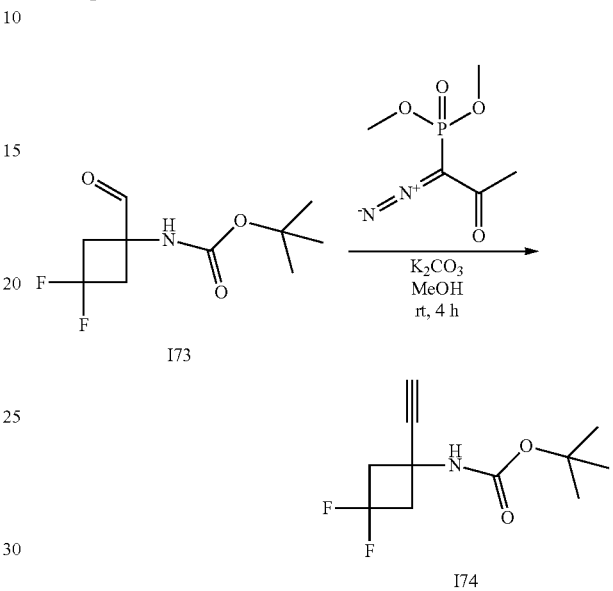

The reaction was performed in anhydrous conditions under Argon atmosphere

To a solution of tert-butyl (3,3-difluoro-1-formylcyclobutyl)carbamate I73 (3.85 g, 16.0 mmol) and K₂CO₃ (5.02 g, 36.33 mmol) in MeOH (100 mL), cooled to 0° C., was added dimethyl (1-diazo-2-oxopropyl)phosphonate (2.73 mL, 18.17 mmol). After 30 min, the reaction mixture was warmed to rt and stirred for 4 h. The reaction mixture was filtered and the filtrate was concentrated. Water (100 mL) was added and the aqueous layer was extracted with DCM (2×100 mL). The combined organic layers were washed with brine, dried (Na₂SO₄), filtered and concentrated to afford tert-butyl (1-ethynyl-3,3-difluorocyclobutyl)carbamate I74 (3.52 g, 91%) as an orange solid which was used as such in the next reaction step.

Step 4

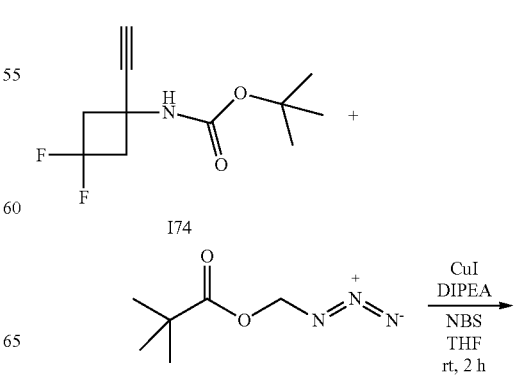

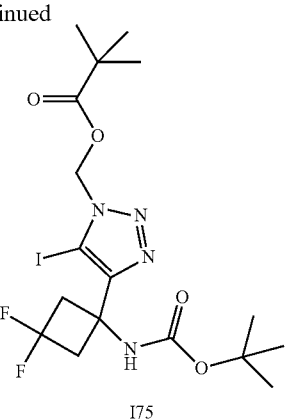

Intermediate (4-(1-((tert-butoxycarbonyl)amino)-3,3-difluorocyclobutyl)-5-iodo-1H-1,2,3-triazol-1-yl)methyl pivalate I75 was synthesized according to the procedure reported for intermediate I62 from tert-butyl (1-ethynyl-3,3-difluorocyclobutyl)carbamate I74.

Step 5

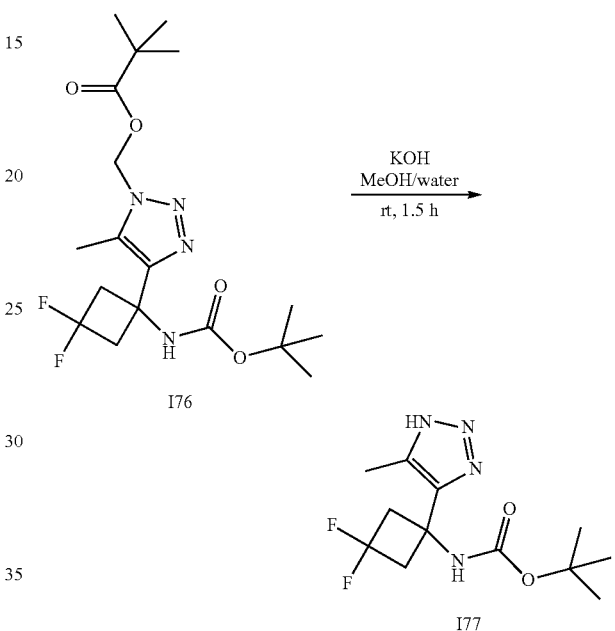

The reaction was performed in anhydrous conditions under Argon atmosphere.

To a solution of (4-(1-((tert-butoxycarbonyl)amino)-3,3-difluorocyclobutyl)-5-iodo-1H-1,2,3-triazol-1-yl)methyl pivalate I75 (346 mg, 0.60 mmol) in 1,4-dioxane (3 mL) were added K₃PO₄ (254 mg, 1.20 mmol) and trimethylboroxine (0.418 mL, 2.99 mmol). Argon was bubbled in the reaction mixture during 10 min and PdCl₂(dppf)₂ (22 mg, 0.03 mmol) was added and the reaction mixture was stirred at 100° C. for 6 h. Additional trimethylboroxine (0.418 mL, 2.99 mmol), K₃PO₄ (254 mg, 1.20 mmol) were added. Argon was bubbled in the reaction mixture during 5 min and additional PdCl₂(dppf)₂ (22 mg, 0.03 mmol) was added and the reaction mixture was stirred at 100° C. for 18 h. The reaction mixture was filtered through a pad of Celite®. The filtrate was concentrated in vacuo and the residue was purified with a flash chromatography (silica, mobile phase: DCM/MeOH, gradient from 100/0 to 96/4) to afford (4-(1-((tert-butoxycarbonyl)amino)-3,3-difluorocyclobutyl)-5-methyl-1H-1,2,3-triazol-1-yl)methyl pivalate I76 (276 mg, 80%, 70% purity) as an orange oil.

Step 6

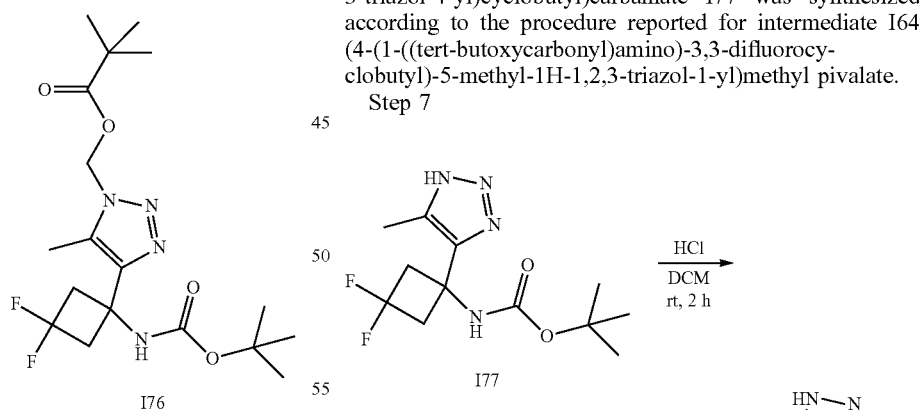

Intermediate tert-butyl (3,3-difluoro-1-(5-methyl-1H-1,2,3-triazol-4-yl)cyclobutyl)carbamate I77 was synthesized according to the procedure reported for intermediate I64 (4-(1-((tert-butoxycarbonyl)amino)-3,3-difluorocyclobutyl)-5-methyl-1H-1,2,3-triazol-1-yl)methyl pivalate.

Step 7

The reaction was performed under Argon atmosphere

A solution of tert-butyl (3,3-difluoro-1-(5-methyl-1H-1,2,3-triazol-4-yl)cyclobutyl)carbamate I77 (126 mg, 0.41 mmol) in a mixture of HCl (4N in 1,4-dioxane, 1.98 ML, 7.93 mmol) and DCM (2 mL) was stirred at rt for 2 h. The reaction mixture was concentrated and the solid obtained was co-evaporated with DIPE (2×5 mL) to afford 3,3-difluoro-1-(5-methyl-1H-1,2,3-triazol-4-yl)cyclobutan-1-amine hydrochloride I78 as a yellow solid which was used as such in the next reaction step.

3.1.16. Synthesis of Intermediate I83

Step 1

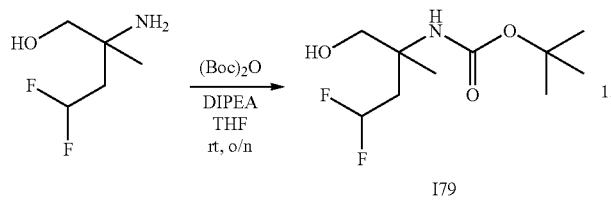

The reaction was performed in anhydrous conditions under argon atmosphere

To a solution of 2-amino-4,4-difluoro-2-methylbutan-1-ol hydrochloride (1.26 g, 7.17 mmol) in THF (40 mL) were added di-tert-butyl dicarbonate (2.35 g, 10.76 mmol) and DIPEA (3.13 mL, 17.94 mmol). The reaction mixture was stirred at room temperature overnight. Water (100 mL) and EtOAc (100 mL) were added and the organic layer was separated. The aqueous layer was extracted with EtOAc (3×100 mL). The combined organic layers were dried (Na$_2$SO$_4$), filtered and concentrated to dryness.

The crude was purified by flash chromatography (silica, mobile phase: cyclohexane/EtOAc, gradient from 95:05 to 70:30) to afford tert-butyl (4,4-difluoro-1-hydroxy-2-methylbutan-2-yl)carbamate I79 (1.46 g, 77%) as a white powder.

Step 2

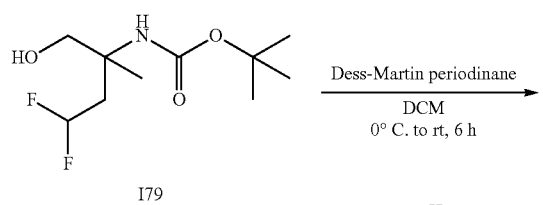

To a solution of tert-butyl (4,4-difluoro-1-hydroxy-2-methylbutan-2-yl)carbamate I79 (1.46 g, 5.49 mmol) in DCM (50 mL) at 0° C., was added Dess Martin Periodinane (3.26 g, 7.69 mmol).

The mixture was warmed to room temperature and stirred for 6 h. The reaction mixture was quenched with Na$_2$S$_2$O$_3$ (N aq.). The aqueous layer was extracted with DCM (3×50 mL). Combined organic layers were washed with NaHCO$_3$ (sat., aq., 2×100 mL), dried over (Na$_2$SO$_4$) and concentrated to dryness. The crude was purified by flash chromatography (silica, mobile phase: cyclohexane/EtOAc, gradient from 95:5 to 60:40) to afford tert-butyl (4,4-difluoro-2-methyl-1-oxobutan-2-yl)carbamate I80 (1.2 g, 87%) as a white powder.

Step 3

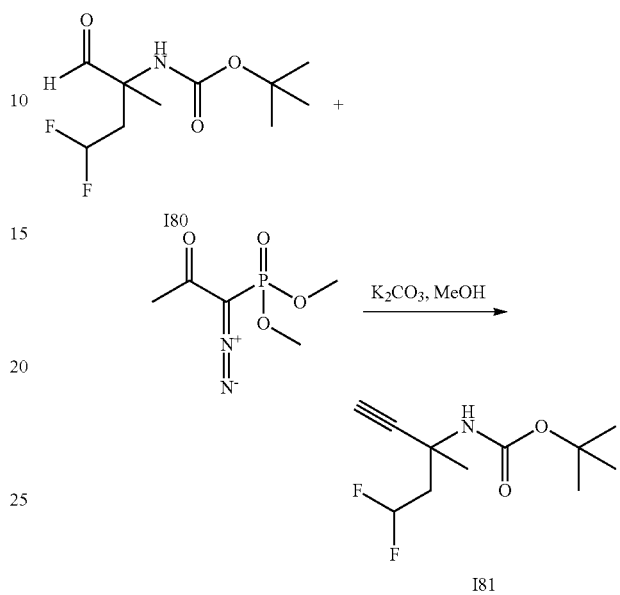

The reaction was performed in anhydrous conditions under argon atmosphere

To a solution of tert-butyl (4,4-difluoro-2-methyl-1-oxobutan-2-yl)carbamate I80 (1.20 g, 4.78 mmol) in MeOH (20 mL) at 0° C., were added K$_2$CO$_3$ (1.32 g, 9.55 mmol) and dimethyl (acetyldiazomethyl)phosphonate (0.75 mL, 5.01 mmol). The mixture was warmed to room temperature and stirred for 18 h. The reaction mixture was concentrated to dryness. The residue was diluted with water and extracted with Et$_2$O (3×50 mL). The combined organic layers were dried (Na$_2$SO$_4$), filtered and concentrated. The residue was taken into DCM (50 mL), dried (Na$_2$SO$_4$), filtered and concentrated to dryness to yield tert-butyl (5,5-difluoro-3-methylpent-1-yn-3-yl)carbamate I81 (1.02 g, 92%) as a white powder which was used in next step without further purification.

Step 4

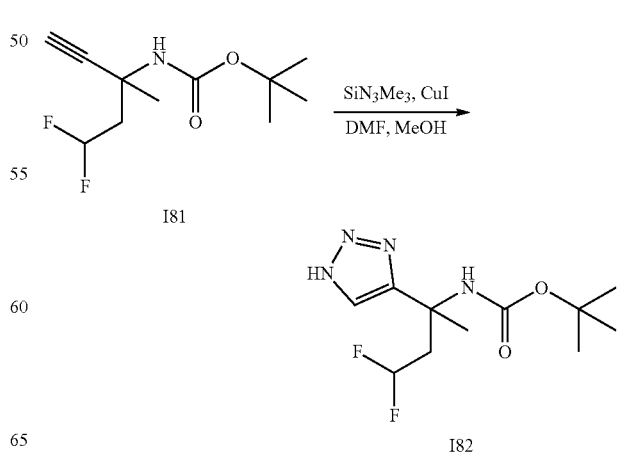

The reaction was performed in anhydrous conditions under argon atmosphere

To a solution of tert-butyl (5,5-difluoro-3-methylpent-1-yn-3-yl)carbamate I81 (1.02 g, 4.37 mmol) in a mixture of DMF (8 mL) and MeOH (0.8 mL) at room temperature were added azidotrimethylsilane (1.61 mL, 12.24 mmol) and copper iodide (42 mg, 0.22 mmol). The reaction mixture was stirred at 100° C. for 7 h. The reaction mixture was diluted with EtOAc (100 mL) and the organic layer was washed with brine (2×100 mL), dried (Na$_2$SO$_4$), filtered and concentrated to dryness. The crude was purified by flash chromatography (silica, mobile phase: DCM/MeOH, gradient from 100:0 to 95:05). The residue was again purified by flash chromatography (silica, mobile phase: cyclohexane/EtOAc, gradient from 90:10 to 50:50) to afford tert-butyl (4,4-difluoro-2-(1H-1,2,3-triazol-4-yl)butan-2-yl)carbamate I82 (630 mg, 52%) as a yellow oil.

Step 5

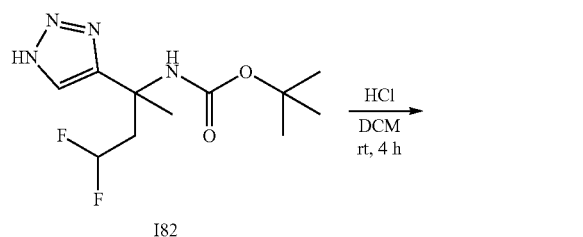

The reaction was performed in anhydrous conditions under argon.

To a solution of tert-butyl (4,4-difluoro-2-(1H-1,2,3-triazol-4-yl)butan-2-yl)carbamate I82 (630 mg, 2.28 mmol) in DCM (12 mL) was added HC (4N in 1,4-dioxane, 8.55 mL, 34.20 mmol).

The reaction mixture was stirred at room temperature for 4 h. The reaction mixture was concentrated to dryness and co-evaporated with DCM (2×20 mL) to afford 4,4-difluoro-2-(1H-1,2,3-triazol-4-yl)butan-2-amine hydrochloride I83 (540 mg, quant.) as a white powder which was used in next step without further purification.

Synthesis of Intermediate I88
Step 1

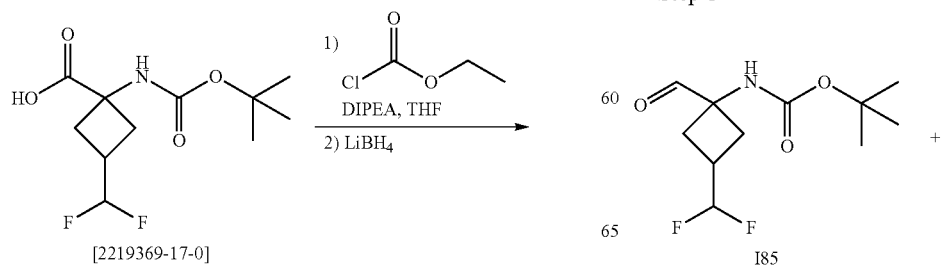

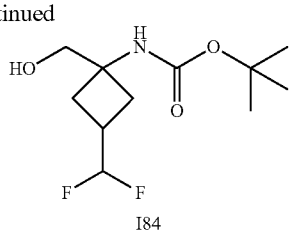

The reaction was performed in anhydrous conditions under argon atmosphere.

To a solution of 1-{[(tert-butoxy)carbonyl]amino}-3-(difluoromethyl)cyclobutane-1-carboxylic acid (1 g, 3.77 mmol) in THF (10 mL) at 0° C. were added DIPEA (788 μL, 4.52 mmol) and dropwise ethyl chloroformate (397 μL, 4.15 mmol). The reaction was stirred at 0° C. for 2 h. The formed precipitate was filtered and washed with THF (5 mL). The filtrate was cooled to 0° C. followed by the addition dropwise of a solution of lithium borohydride (4N in THF, 1.88 mL, 7.54 mmol). The reaction was stirred at rt for 4 h. The reaction mixture was diluted with water (100 mL) and extracted with EtOAc (3×100 mL). Combined organic layers were washed with brine, dried over (Na$_2$SO$_4$), filtered and concentrated. The crude was purified by flash chromatography (silica, mobile phase: cyclohexane/EtOAc, gradient from 100/0 to 5/5) to afford tert-butyl (3-(difluoromethyl)-1-(hydroxymethyl)cyclobutyl)carbamate I84 (804 mg, 70%, 83% purity) as a white solid.

Step 2

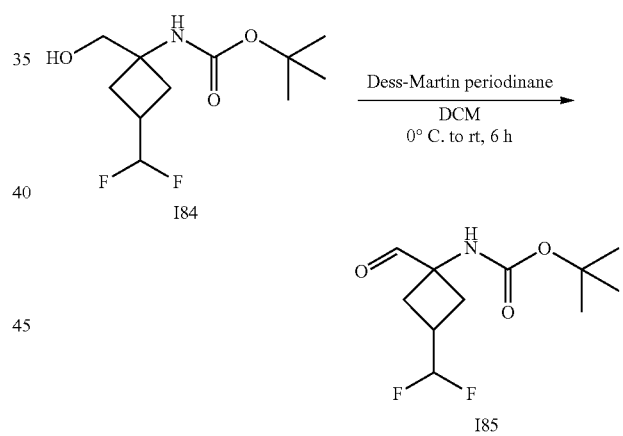

Intermediate tert-butyl (3-(difluoromethyl)-1-formylcyclobutyl)carbamate I85 was prepared similarly as described for the synthesis of intermediate I80 from tert-butyl (3-(difluoromethyl)-1-(hydroxymethyl)cyclobutyl)carbamate I84.

Step 3

-continued

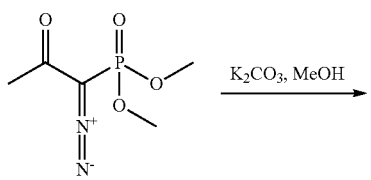

K₂CO₃, MeOH

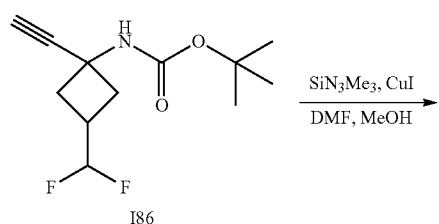

Intermediate tert-butyl (3-(difluoromethyl)-1-ethynylcyclobutyl)carbamate I86 was prepared similarly as described for the synthesis of intermediate I81 from tert-butyl (3-(difluoromethyl)-1-formylcyclobutyl)carbamate I85.

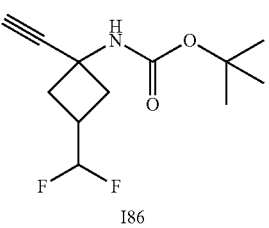

SiN₃Me₃, CuI
―――――――――→
DMF, MeOH

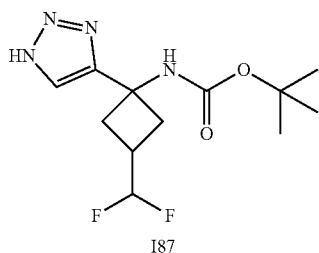

Intermediate tert-butyl (3-(difluoromethyl)-1-(1H-1,2,3-triazol-4-yl)cyclobutyl)carbamate I87 was prepared similarly as described for the synthesis of intermediate I82 from tert-butyl (3-(difluoromethyl)-1-ethynylcyclobutyl)carbamate I86.

Step 5

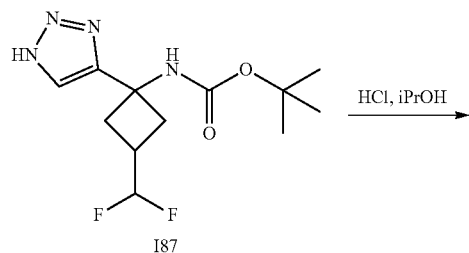

HCl, iPrOH
―――――――→

-continued

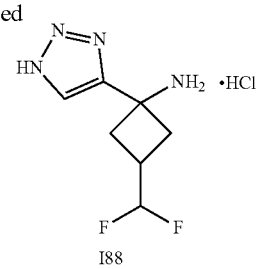

Intermediate 3-(difluoromethyl)-1-(1H-1,2,3-triazol-4-yl)cyclobutan-1-amine hydrochloride I88 was prepared similarly as described for the synthesis of intermediate I83 from tert-butyl (3-(difluoromethyl)-1-(1H-1,2,3-triazol-4-yl)cyclobutyl)carbamate I87.

3.1.16. Synthesis of Intermediate I89

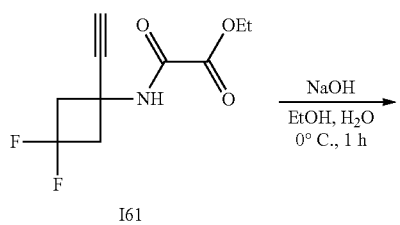

NaOH
――――――→
EtOH, H₂O
0° C., 1 h

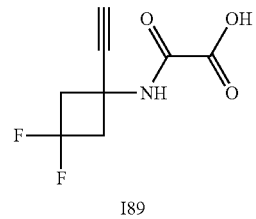

To a solution of ethyl 2-((1-ethynyl-3,3-difluorocyclobutyl)amino)-2-oxoacetate I61 (675 mg, 2.92 mmol) in a mixture of EtOH (7 mL) and H₂O (2 mL) at 0° C. was added dropwise NaOH (1M in EtOH, 4.38 mL, 4.38 mmol). The reaction mixture was stirred at 0° C. for 1 h. The reaction mixture was diluted with water (50 mL), acidified until pH=1 with HCl (1M, aq., 7 mL) then extracted with DCM (3×40 mL) then with EtOAc/EtOH (9/1; 3×20 mL). The combined organic layers were dried (Na₂SO₄), filtered and concentrated to give 2-((1-ethynyl-3,3-difluorocyclobutyl)amino)-2-oxoacetic acid I89 (492 mg, 83%) as a beige solid.

3.2. Synthesis of Compounds 3.2.1. Synthesis of Compound C1

(3S)—N-(3-Cyano-4-fluorophenyl)-1-[{[3,3-difluoro-1-(1H-1,2,3-triazol-4-yl)cyclobutyl]amino}(oxo)acetyl]pyrrolidine-3-carboxamide

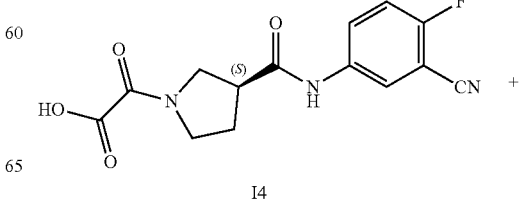

+

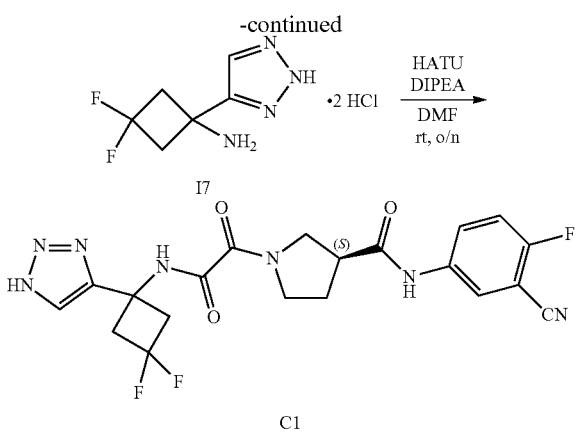

A mixture of intermediate I4 (570 mg, 1.87 mmol), 3,3-difluoro-1-(2H-1,2,3-triazol-4-yl)cyclobutan-1-amine 17 dihydrochloride (577 mg, 2.33 mmol), HATU (852 mg, 2.24 mmol) and DIPEA (1.61 mL, 9.34 mmol) in DMF (10 mL) was stirred at room temperature overnight. The volatiles were removed under reduced pressure. The residue was purified by flash column chromatography (silica, mobile phase: heptane/EtOAc). A second purification was performed via preparative HPLC (stationary phase: RP XBridge Prep C18 OBD-10 μm, 50×150 mm, mobile phase: NH$_4$HCO$_3$ (0.25% in water)/MeOH) to afford compound C1 (254 mg, 49%) as a white foam.

LCMS (method A): Rt=0.77 min, m/z calcd. for C$_{20}$H$_{18}$F$_3$N$_7$O$_3$ 461, m/z found 462 [M+H]$^+$; $^1$H NMR (400 MHz, DMSO-d$_6$) δ ppm 14.68-15.03 (m, 1H), 10.46 (d, J=9.7 Hz, 1H), 9.68 (s, 1H), 8.12 (td, J=5.7, 2.9 Hz, 1H), 7.80-7.88 (m, 1H), 7.68-7.78 (m, 1H), 7.50 (td, J=9.1, 2.2 Hz, 1H), 3.39-3.98 (m, 4H), 3.14-3.28 (m, 5H), 1.99-2.26 (m, 2H).

3.2.2. Synthesis of Compound C1 as HCl salt (3S)—N-(3-Cyano-4-fluorophenyl)-1-[{[3,3-difluoro-1-(1H-1,2,3-triazol-4-yl)cyclobutyl]amino}(oxo)acetyl]pyrrolidine-3-carboxamide hydrochloride

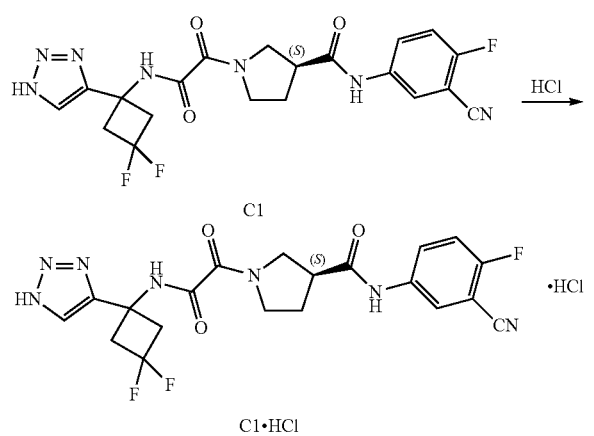

Compound C1 was dissolved in DCM and HCl (4M in 1,4-dioxane, 1 mL, 4.00 mmol) was added.

The volatiles were removed under reduced pressure. The residue was triturated in DIPE, and filtered off to afford compound C1.HCl.

LCMS (method B): Rt=1.51 min, m/z calcd. for C$_{20}$H$_{18}$F$_3$N$_7$O$_3$ 461, m/z found 462 [M+H]$^+$; $^1$H NMR (400 MHz, DMSO-d$_6$) δ ppm 10.56 (d, J=14.1 Hz, 1H), 9.69 (s, 1H), 8.13 (td, J=5.9, 2.6 Hz, 1H), 7.82-7.90 (m, 1H), 7.74 (d, J=8.6 Hz, 1H), 7.50 (td, J=9.1, 1.8 Hz, 1H), 3.39-3.99 (m, 4H), 3.11-3.34 (m, 5H), 1.96-2.29 (m, 2H).

3.2.3. Synthesis of Compound C2

(3S)-1-[{[3,3-Difluoro-1-(1H-1,2,3-triazol-4-yl)cyclobutyl]amino}(oxo)acetyl]-N-(4-fluoro-3-methylphenyl)pyrrolidine-3-carboxamide

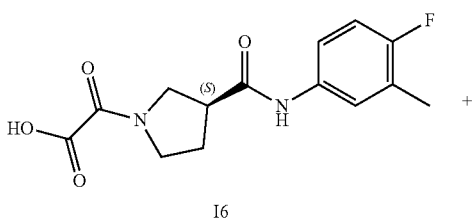

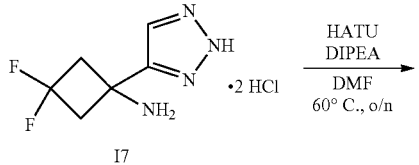

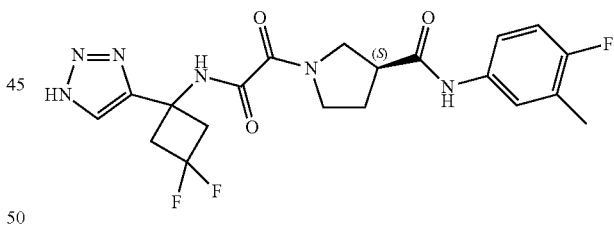

Compound C2 was prepared as similarly described for the synthesis of compound C1. The reaction mixture was loaded on a silica cartridge and the mixture was purified by flash column chromatography (silica, mobile phase: heptane/EtOAc). A second purification was performed by flash column chromatography (silica, mobile phase: heptane/(EtOAc:EtOH, 3:1)) to afford compound C2 (182 mg, 52%) as a white powder.

LCMS (method A): Rt=0.82 min, m/z calcd. for C$_{20}$H$_{21}$F$_3$N$_6$O$_3$ 450, m/z found 451 [M+H]$^+$; $^1$H NMR (400 MHz, DMSO-d$_6$) δ ppm 13.90-15.72 (m, 1H), 10.05 (br d, J=10.3 Hz, 1H), 9.69 (s, 1H), 7.75 (br d, J=7.7 Hz, 1H), 7.47-7.58 (m, 1H), 7.34-7.45 (m, 1H), 7.06 (br t, J=9.0 Hz,

3.2.4. Synthesis of Compound C3

(2S,3S)-1-[{[3,3-Difluoro-1-(1H-1,2,3-triazol-4-yl)cyclobutyl]amino}(oxo)acetyl]-2-methyl-N-(3,4,5-trifluorophenyl)pyrrolidine-3-carboxamide

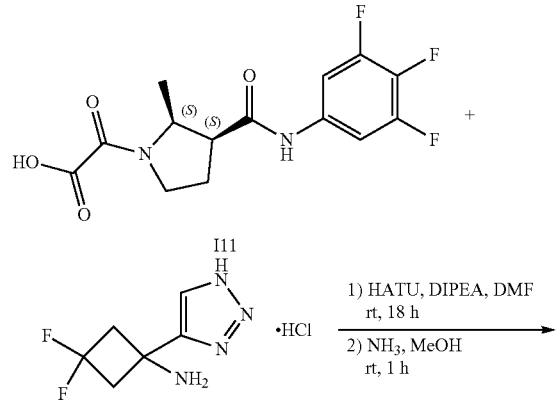

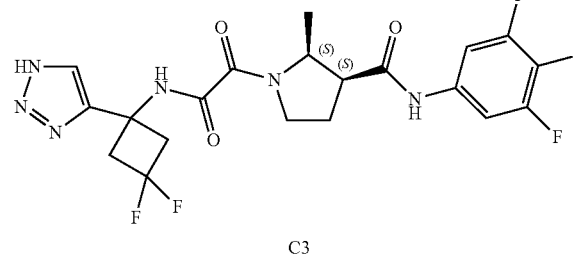

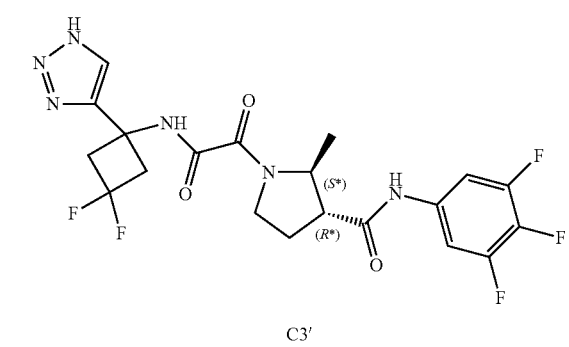

The reaction was performed under anhydrous conditions and under Ar atmosphere.

To a mixture of intermediate I11 (260 mg, 0.79 mmol) and intermediate I7 hydrochloride (182 mg, 0.87 mmol) in DMF (4 mL), were added HATU (599 mg, 1.58 mmol) and DIPEA (0.55 mL, 3.15 mmol). The reaction mixture was stirred at room temperature for 18 h. The reaction mixture was diluted with water (10 mL) and the aqueous layer was extracted with EtOAc (2×15 mL). The combined organic layers were washed with brine, dried ($Na_2SO_4$), filtered and concentrated under reduced pressure. The crude mixture was purified by flash column chromatography (silica, mobile phase: DCM/MeOH, gradient from 100:0 to 95:5). The residue was dissolved in $NH_3$ (7M in MeOH, 5 mL) and the solution was stirred at room temperature for 1 h, concentrated to dryness, co-evaporated with EtOAc (2×5 mL) and dried under vacuum at 50° C. overnight. The product was finally purified via Prep SFC (stationary phase: Chiralpak Daicel IC 20×250 mm, mobile phase: $CO_2$, EtOH+0.4% i-$PrNH_2$) to afford compound C3 (210 mg, 55%) and the by-product C3' (8 mg, 2%).

C3:

LCMS (method D): Rt=1.80 min, m/z calcd. for $C_{20}H_{19}F_5N_6O_3$ 486, m/z found 487 [M+H]$^+$; $^1$H $^1$H NMR (400 MHz, DMSO-d6, 27° C.) δ ppm 0.90-1.08 (m, 3H) 1.88-2.07 (m, 1H) 2.20-2.38 (m, 1H) 3.03-3.93 (m, 7H) 4.45-4.94 (m, 1H) 7.38-7.59 (m, 2H) 7.63-7.91 (m, 1H) 9.63-9.80 (m, 1H) 10.25-10.50 (m, 1H) 14.48-15.37 (m, 1H) (mixture of rotamers).

C3':

$^1$H NMR (400 MHz, DMSO-d6, 27° C.) δ ppm 1.15-1.34 (m, 3H) 1.93-2.13 (m, 1H) 2.15-2.30 (m, 1H) 2.75-2.90 (m, 1H) 3.09-3.85 (m, 6H) 4.18-4.66 (m, 1H) 7.37-7.59 (m, 2H) 7.61-7.82 (m, 1H) 9.61-9.74 (m, 1H) 10.35-10.51 (m, 1H) 13.45-16.27 (m, 1H) (mixture of rotamers).

3.2.5. Synthesis of Compound C$_{1-4}$

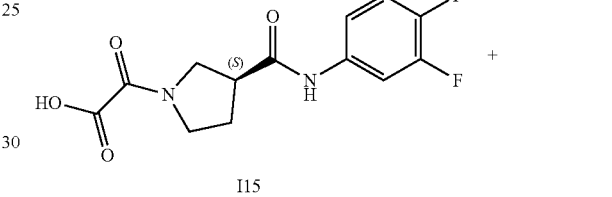

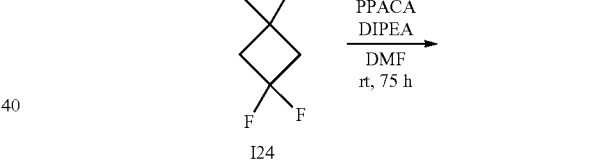

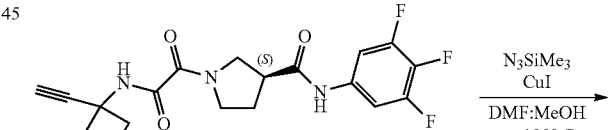

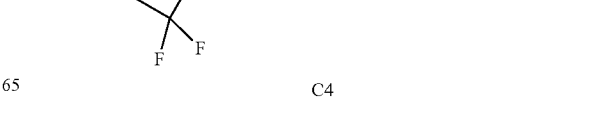

Intermediate I25

(3S)-1-{[(1-Ethynyl-3,3-difluorocyclobutyl)amino](oxo)acetyl}-N-(3,4,5-trifluorophenyl)pyrrolidine-3-carboxamide

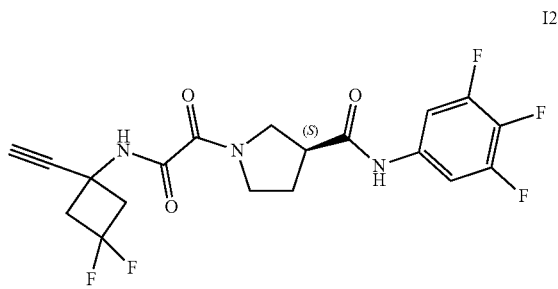

I25

The reaction was performed under anhydrous conditions and under Ar atmosphere.

To a solution of intermediate I15 (0.23 g, 0.73 mmol) in DMF (2.5 mL) were added intermediate I24 (146 g, 0.87 mmol), PPACA (0.38 mL, 2.18 mmol, 50% purity) and DIPEA (0.65 mL, 1.09 mmol). The reaction mixture was stirred at room temperature for 75 h and diluted with EtOAc (80 mL). The organic layer was successively washed with NaHCO$_3$ (sat., aq., 2×80 mL), HCl (1N, aq., 2×80 mL) and brine (2×80 mL), dried (Na$_2$SO$_4$), filtered and concentrated to dryness. The crude mixture was purified by flash column chromatography (silica, mobile phase: DCM/MeOH, gradient from 100:0 to 95:5) to afford intermediate I25 (200 mg, 59%, 92% purity).

Compound C$_{1-4}$ (3S)-1-[{[3,3-Difluoro-1-(1H-1,2,3-triazol-4-yl)cyclobutyl]amino}(oxo)acetyl]-N-(3,4,5-trifluorophenyl)pyrrolidine-3-carboxamide

C4

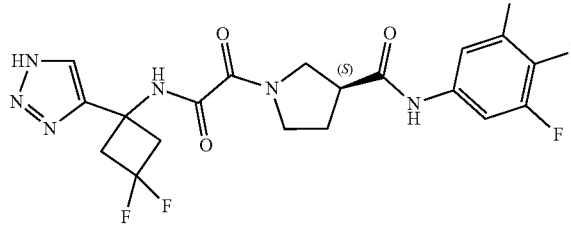

The reaction was performed under anhydrous conditions and under Ar atmosphere.

To a solution of intermediate I25 (0.20 g, 0.43 mmol, 92% purity) in a mixture of DMF (0.4 mL) and MeOH (0.045 mL) were added azidotrimethylsilane (85 μL, 0.64 mmol) and CuI (4.10 mg, 22 μmol). The reaction mixture was stirred at 100° C. using a single mode microwave (Biotage Initiator EXP60 system) for 20 min, then 10 min and again 10 min. The reaction mixture was filtered under PTFE filter. The filtrate was diluted with EtOAc (100 mL) and the organic layer was washed with NH$_4$OH (aq., 2×100 mL) and brine (2×100 mL), dried (Na$_2$SO$_4$), filtered and concentrated to dryness. The crude was purified by flash column chromatography (silica, mobile phase: DCM/MeOH, gradient from 100:0 to 95:5). A second purification was performed by flash column chromatography (C18, mobile phase: CH$_3$CN (0.05% HCOOH)/H$_2$O (0.1% HCOOH), gradient from 0:100 to 40:60). The residue was solubilized in EtOAc (30 mL) and the organic layer was washed with NH$_4$HCO$_3$ (0.2 wt. % in H$_2$O) (3×30 mL), dried (Na$_2$SO$_4$), filtered, concentrated to dryness and dried under vacuum at 50° C. overnight. The product was co-evaporated with EtOH (3×5 mL), and dried under vacuum at 50° C. overnight to afford compound C$_{1-4}$ (80 mg, 39%).

LCMS (method C): Rt=9.0 min, m/z calcd. for C$_{19}$H$_{17}$F$_5$N$_6$O$_3$ 472, m/z found 473 [M+H]$^+$; $^1$H NMR (400 MHz, DMSO-d$_6$, 80° C.) δ ppm 14.50-14.98 (m, 1H), 10.07-10.37 (m, 1H), 9.43 (br s, 1H), 7.71 (br d, J=5.8 Hz, 1H), 7.42-7.57 (m, 2H), 3.78-4.01 (m, 2H), 3.55-3.76 (m, 2H), 3.13-3.39 (m, 5H), 2.00-2.29 (m, 2H).

3.2.6 Synthesis of Compound C5

(3S)—N-(3-Chloro-4-fluorophenyl)-1-[{[3,3-difluoro-1-(1H-1,2,3-triazol-4-yl)cyclobutyl]amino}(oxo)acetyl]pyrrolidine-3-carboxamide

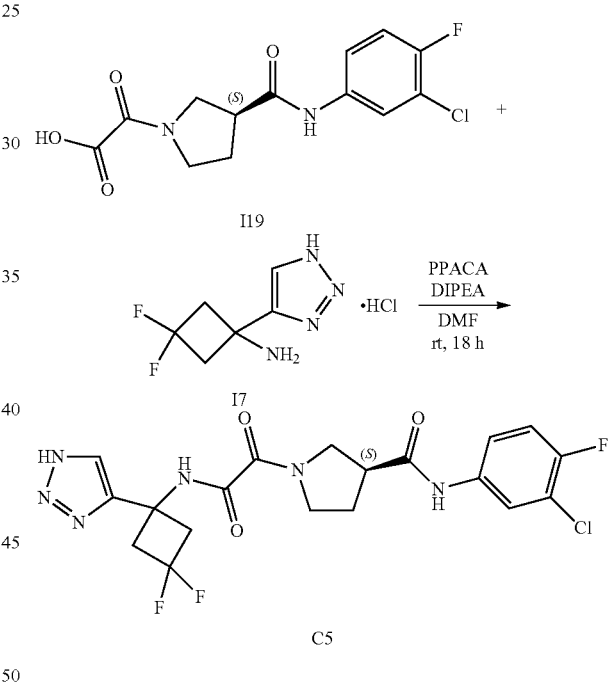

The reaction was performed under anhydrous conditions and under Ar atmosphere.

To a solution of intermediate I19 (230 mg, 0.57 mmol, 78% purity) in DMF (10 mL) were added intermediate I7 hydrochloride (240 mg, 1.14 mmol), PPACA (1.19 mL, 1.99 mmol, 50% purity) and DIPEA (497 μL, 2.85 mmol). The reaction mixture was stirred at room temperature for 18 h. The reaction mixture was combined with another fraction (0.16 mmol) and diluted with water (30 mL). The aqueous phase was extracted with EtOAc (3×40 mL). The combined organic layers were washed with brine (2×40 mL), dried (Na$_2$SO$_4$), filtered and concentrated under vacuum. The crude mixture was purified by reversed phase flash column chromatography (C18, mobile phase: MeCN/water, gradient from 2:98 to 100:0). The residue was co-evaporated with EtOH, and dried under vacuum for 4 days at 50° C. to afford compound C5 (167 mg, 49%) as a white solid.

LCMS (method C): Rt=8.90 min, m/z calcd. for $C_{19}H_{18}ClF_3N_6O_3$ 470, m/z found 471 [M+H]$^+$;

$^1$H NMR (400 MHz, DMSO-d$_6$, 81° C.) δ ppm 14.49-14.95 (m, 1H), 10.06 (br d, J=7.1 Hz, 1H), 9.42 (s, 1H), 7.83-7.97 (m, 1H), 7.71 (br d, J=4.6 Hz, 1H), 7.43-7.54 (m, 1H), 7.33 (td, J=9.1, 1.6 Hz, 1H), 3.78-4.02 (m, 2H), 3.56-3.76 (m, 2H), 3.15-3.39 (m, 5H), 1.98-2.30 (m, 2H).

3.2.7. Synthesis of Compound C6

(2S,3S)—N-(3-Cyano-4-fluorophenyl)-1-[{[3,3-difluoro-1-(1H-1,2,3-triazol-4-yl)cyclobutyl]amino}(oxo)acetyl]-2-methylpyrrolidine-3-carboxamide

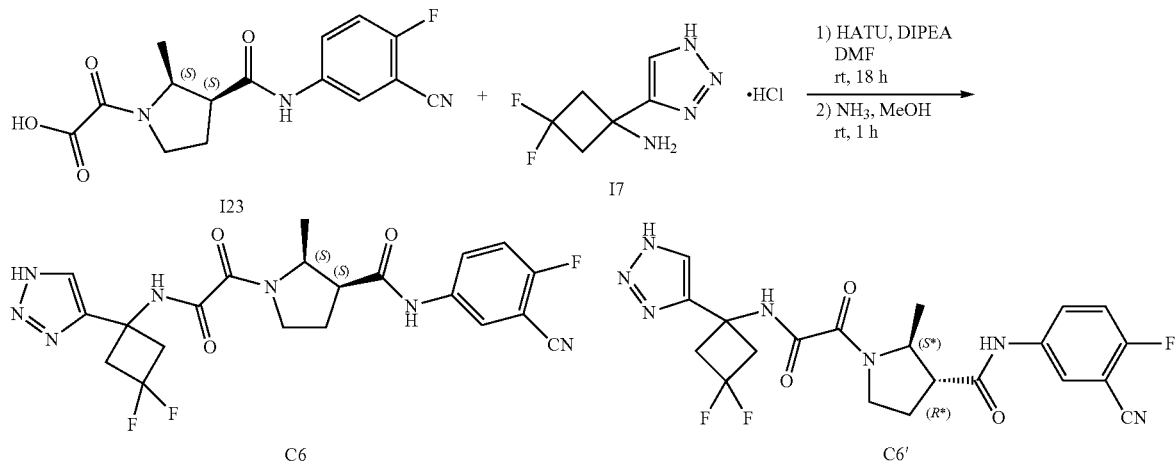

Compound C6 was prepared similarly as described for the synthesis of compound C3.

The product was finally purified via Prep SFC (stationary phase: Chiralpak Daicel IC 20×250 mm, mobile phase: CO$_2$, i-PrOH+0.4% i-PrNH$_2$) to afford compound C6 (112 mg, 30%) and the byproduct C6' (13 mg, 4%, 90% pure).

C6:

LCMS (method D): Rt=1.58 min, m/z calcd. for $C_{21}H_{20}F_3N_7O_3$ 475, m/z found 476 [M+H]$^+$;

$^1$H NMR (400 MHz, DMSO-d$_6$, 27° C.) δ ppm 0.93-1.07 (m, 3H) 1.92-2.05 (m, 1H) 2.22-2.39 (m, 1H) 3.08-3.30 (m, 5H) 3.37-3.88 (m, 2H) 4.47-4.91 (m, 1H) 7.46-7.55 (m, 1H) 7.73 (br s, 1H) 7.79-7.89 (m, 1H) 8.06-8.16 (m, 1H) 9.62-9.83 (m, 1H) 10.31-10.46 (m, 1H) 14.59-15.19 (m, 1H) (mixture of rotamers).

C6':

LCMS (method D): Rt=1.54 min m/z calcd. for $C_{21}H_{20}F_3N_7O_3$ 475, m/z found 476 [M+H]$^+$;

$^1$H NMR (600 MHz, DMSO-d$_6$, 87° C.) δ ppm 10.05-10.28 (m, 1H), 9.24-9.48 (m, 1H), 8.01-8.09 (m, 1H), 7.77-7.87 (m, 1H), 7.59-7.72 (m, 1H), 7.38-7.46 (m, 1H), 4.22-4.69 (m, 1H), 3.37-3.87 (m, 2H), 3.13-3.29 (m, 4H), 2.78-2.90 (m, 1H), 2.13-2.28 (m, 1H), 1.98-2.12 (m, 1H), 1.21-1.32 (m, 3H) (mixture of rotamers).

3.2.7 Synthesis of Compounds C7-C10

The final compounds in the table below were synthesized in two reaction steps according to the procedure reported for compound $C_{1-4}$

| Co. No. | Structure | Reagents step 1 |
|---|---|---|
| C9 | 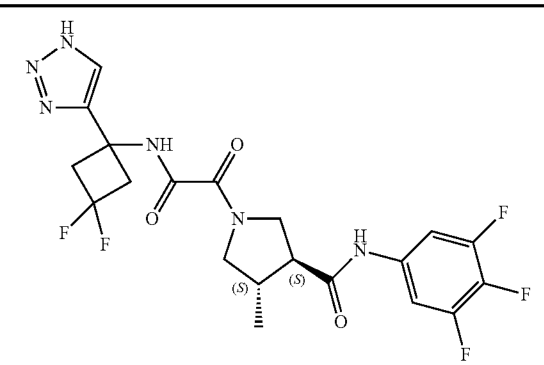 | I26 |

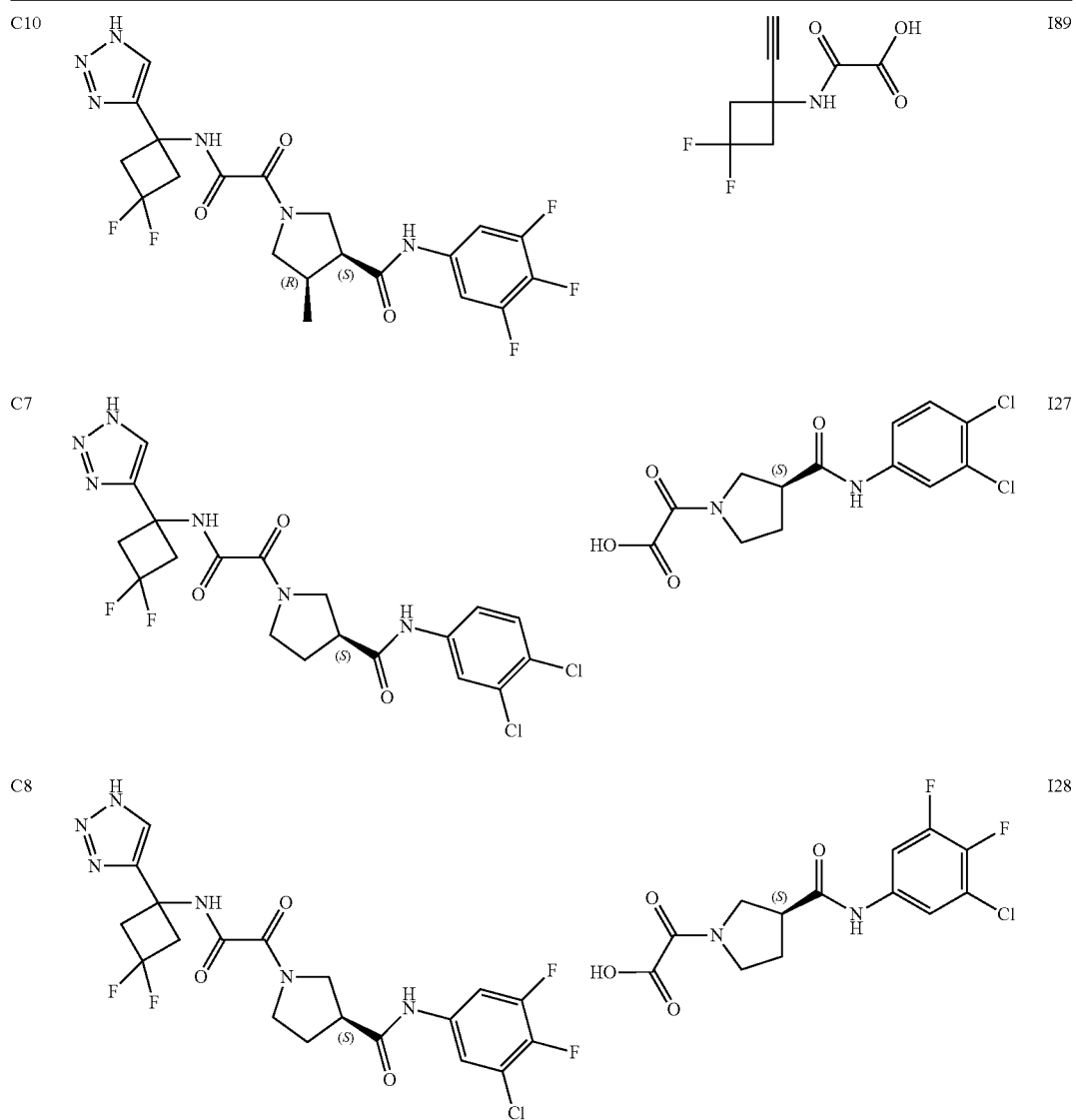
| Co. No. | Reagents step 1 | | Yield (%) |
|---|---|---|---|
| C9 | 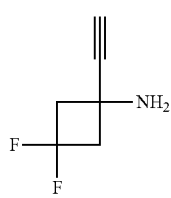 | I24 | 66 |
| C10 | 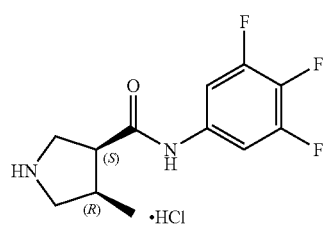 | I40 | 52 |

| | | | |
|---|---|---|---|
| C7 | 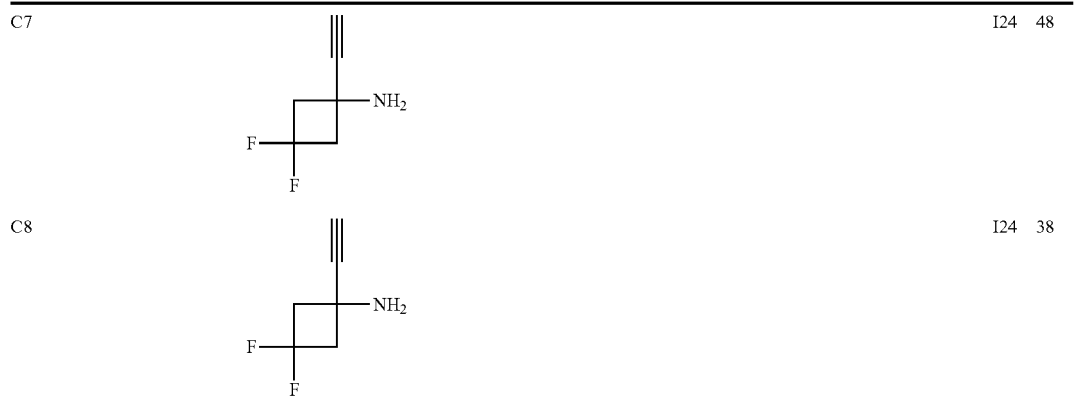 | I24 | 48 |
| C8 | | I24 | 38 |

3.2.8. Synthesis of Compound C21 and Analogues

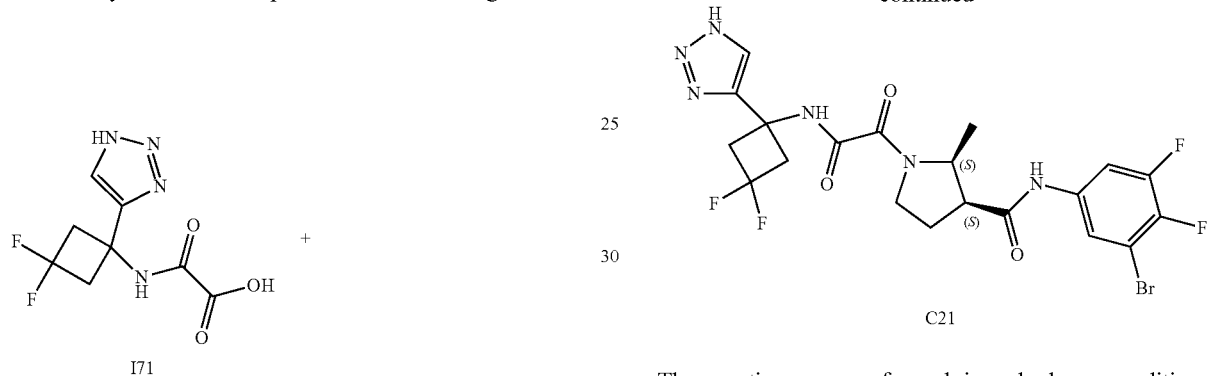

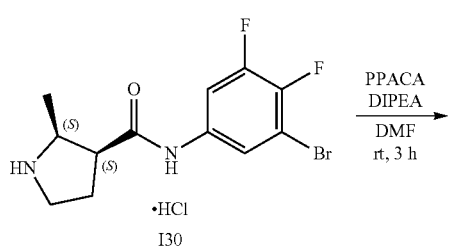

C21

The reaction was performed in anhydrous conditions under argon atmosphere

To a solution of intermediate I30 (146 mg, 0.36 mmol) in DMF (1.5 mL) at room temperature were added I71 (113 mg, 0.43 mmol), DIPEA (0.25 mL, 1.45 mmol) and PPACA (0.323 mL, 0.542 mmol). The reaction mixture was stirred at room temperature for 3 hours. The reaction mixture was diluted with EtOAc (100 mL) and the organic layer was washed with NaHCO$_3$ (sat., aq., 2×50 mL), HCl (1N, aq., 2×50 mL) and brine (2×50 mL), dried (Na$_2$SO$_4$), filtered and concentrated to dryness. The crude was purified by flash chromatography (silica, mobile phase: DCM/MeOH, gradient from 100:0 to 95:05). The fractions containing the desired product were co-evaporated with EtOH, dried under vacuum at 50° C. overnight to yield the title compound (2S,3S)—N-(3-bromo-4,5-difluorophenyl)-1-(2-((3,3-difluoro-1-(1H-1,2,3-triazol-4-yl)cyclobutyl)amino)-2-oxoacetyl)-2-methylpyrrolidine-3-carboxamide (120 mg, 61%) as a white powder.

The final compounds in the table below were synthesized according to the procedure reported for compound C21.

| Co. No. | Structure | Coupling partner 1 | Coupling partner 2 | Yield (%) |
|---|---|---|---|---|
| C26 | | I64 | I9 73 |
| C38 | | I11 | I78 34 |

| Co. No. | Structure | Coupling partner 1 | | Coupling partner 2 | | Yield (%) |
|---|---|---|---|---|---|---|
| C22 | (structure) | I71 | (structure) | I43 | (structure) ·HCl | 75 |
| C23 | (structure) | I71 | (structure) | I52 | (structure) ·HCl | 88 |

| Co. No. | Structure | Coupling partner 1 | Coupling partner 2 | Yield (%) |
|---|---|---|---|---|
| C24 | (structure with 3-chloro-4-fluoro-5-methylanilide) | I71 | I53 | 80 |
| C27 | (structure with 3,4-difluoro-5-methylanilide) | I71 | I54 | 77 |

-continued

| Co. No. | Structure | Coupling partner 1 | Coupling partner 2 | Yield (%) |
|---|---|---|---|---|
| C14 | 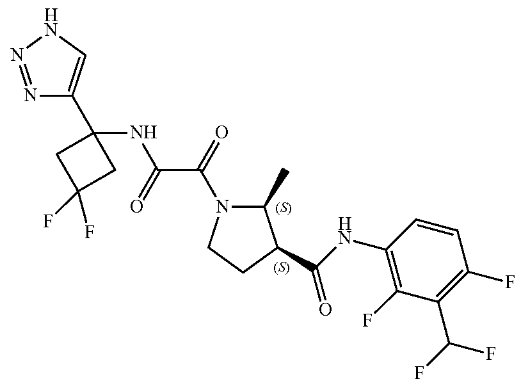 | I71 | I55 | 56 |
| C15 | 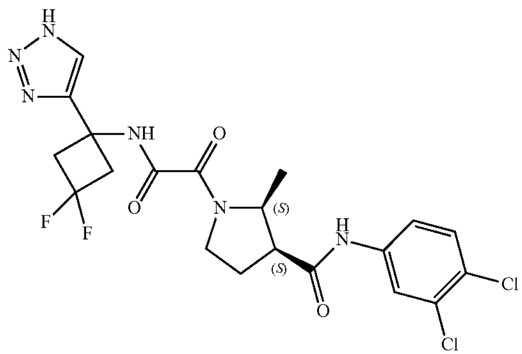 | I71 | I35 | 84 |

| Co. No. | Structure | Coupling partner 1 | | Coupling partner 2 | Yield (%) |
|---|---|---|---|---|---|
| C16 | (structure) | (structure) | I71 | (structure) ·HCl | I36 71 |
| C17 | (structure) | (structure) | I71 | (structure) ·HCl | I56 72 |

| Co. No. | Structure | Coupling partner 1 | | Coupling partner 2 | | Yield (%) |
|---|---|---|---|---|---|---|
| C18 | (triazole-cyclobutane(F,F)-NH-C(O)-C(O)-N-pyrrolidine(2S-Me,4S)-C(O)NH-(4-F,3-CF₃-phenyl)) | I71 | (triazole-cyclobutane(F,F)-C(NH-C(O)-C(O)OH)) | I57 | (2S-methyl-pyrrolidine-3S-C(O)NH-(4-F,3-CF₃-phenyl))·HCl | 80 |
| C20 | (triazole-cyclobutane(F,F)-NH-C(O)-C(O)-N-pyrrolidine(2S-Me,4S)-C(O)NH-(4-F,3-Cl-phenyl)) | I71 | (triazole-cyclobutane(F,F)-C(NH-C(O)-C(O)OH)) | I37 | (2S-methyl-pyrrolidine-3S-C(O)NH-(4-F,3-Cl-phenyl))·HCl | 46 |

-continued

| Co. No. | Structure | Coupling partner 1 | | Coupling partner 2 | | Yield (%) |
|---|---|---|---|---|---|---|
| C30 | (structure with 4-F, 3-CF₃ aryl) | I69 | (triazole oxoacetic acid) | I57 | (S,S)-2-methylpyrrolidine-3-carboxamide with 4-F-3-CF₃ aryl ·HCl | 91 |
| C25 | (structure with 3,4-diCl aryl) | I69 | (triazole oxoacetic acid) | I35 | (S,S)-2-methylpyrrolidine-3-carboxamide with 3,4-diCl aryl ·HCl | 89 |

| Co. No. | Structure | Coupling partner 1 | | Coupling partner 2 | | Yield (%) |
|---|---|---|---|---|---|---|
| C28 | 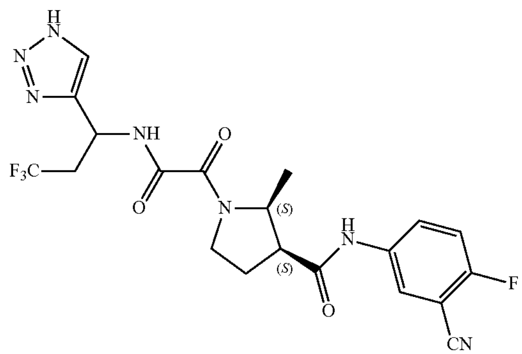 | I23 | | I67 | | 78 |
| C29 | 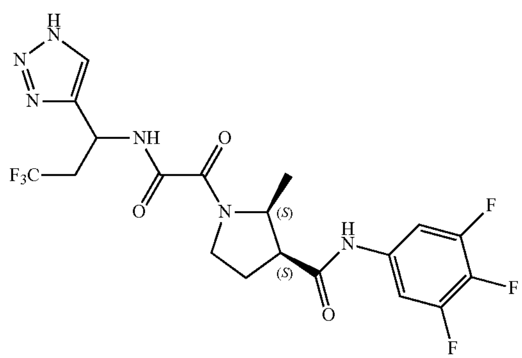 | I11 | | I67 | | 66 |

-continued

| Co. No. | Structure | Coupling partner 1 | | Coupling partner 2 | | Yield (%) |
|---|---|---|---|---|---|---|
| C31 | 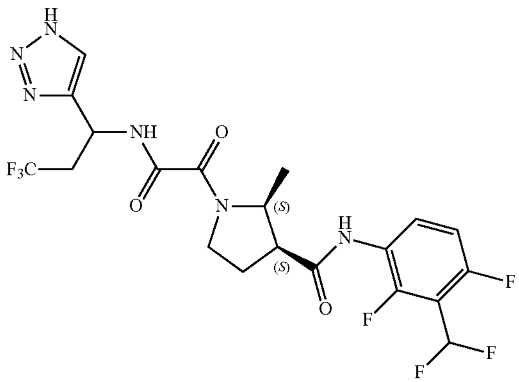 | I69 | | I55 | | 94 |
| C32 | 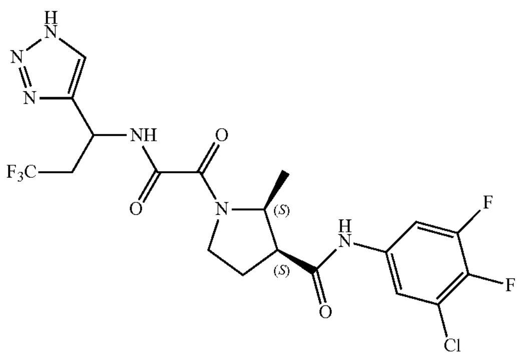 | I69 | | I36 | | 71 |

-continued

| Co. No. | Structure | Coupling partner 1 | | Coupling partner 2 | | Yield (%) |
|---|---|---|---|---|---|---|
| C34 | (structure with 3-chloro-4-fluoroanilide) | (triazole oxoacetic acid) | I69 | (S,S)-2-methylpyrrolidine-3-carboxamide, 3-chloro-4-fluoroanilide ·HCl | I37 | 79 |
| C37 | (structure with 3-chloro-2,4-difluoroanilide) | (triazole oxoacetic acid) | I69 | (S,S)-2-methylpyrrolidine-3-carboxamide, 3-chloro-2,4-difluoroanilide ·HCl | I56 | 75 |

| Co. No. | Structure | Coupling partner 1 | Coupling partner 2 | Yield (%) |
|---|---|---|---|---|
| C33 | 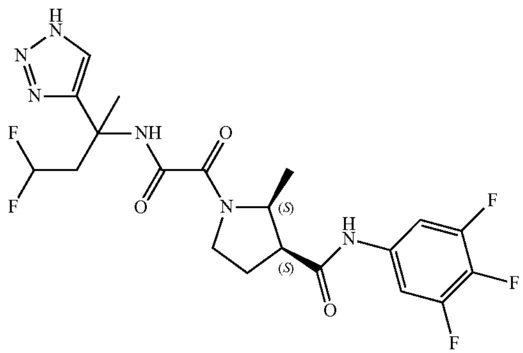 | I11 | I83 | 63 |
| C13 | 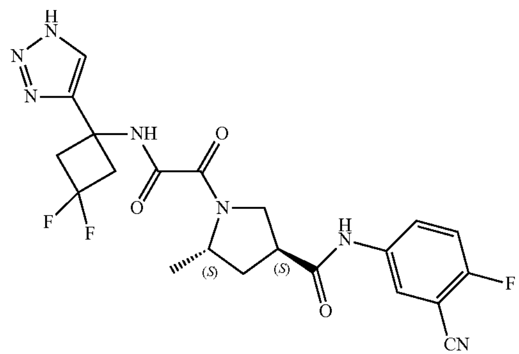 | I71 | I38 | 47 |

| Co. No. | Structure | Coupling partner 1 | Coupling partner 2 | Yield (%) |
|---|---|---|---|---|
| C19 | 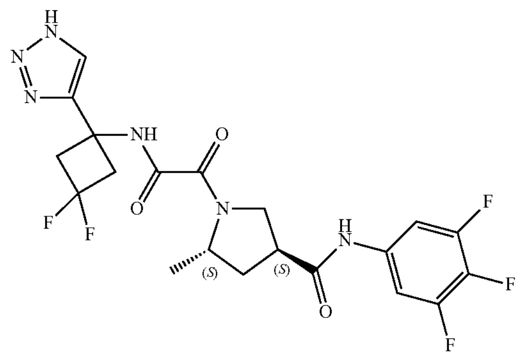 | I71 | I39 | 71 |
| C35 | 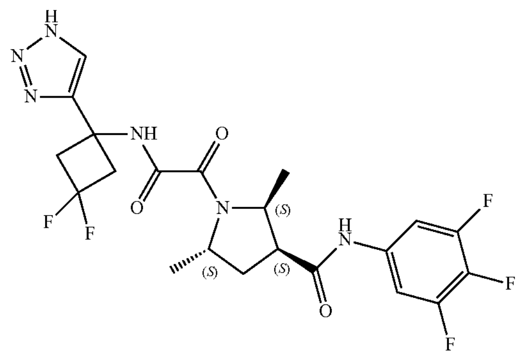 | I71 | I58 | 43 |

| Co. No. | Structure | Coupling partner 1 | Coupling partner 2 | Yield (%) |
|---|---|---|---|---|
| C36 | (structure) | I69 | I58 | 51 |
| C11 | (structure) | I71 | I59 | 65 |

| Co. No. | Structure | Coupling partner 1 | Coupling partner 2 | Yield (%) |
|---|---|---|---|---|
| C12 | 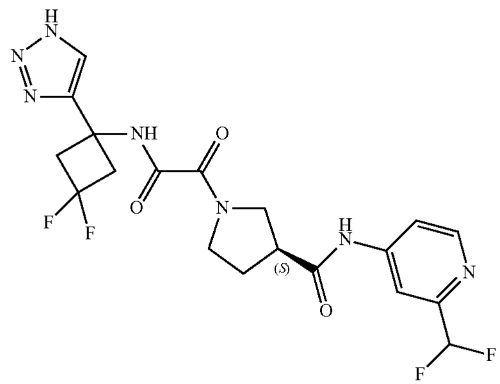 | I71 | I60 | 63 |
| C39 | 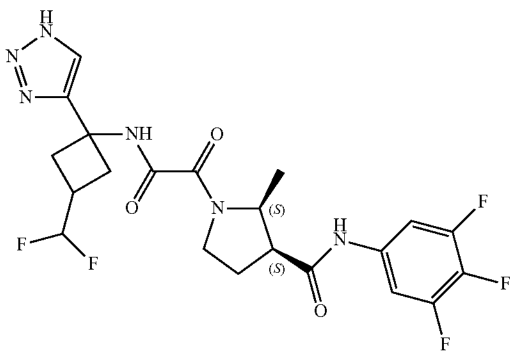 | I88 | I11 | 50 |

3.2.9 Separation of Chiral Compounds
Chiral compounds below were obtained by SFC separation of the corresponding mixture.

| Co. No. | Structure | Method |
|---|---|---|
| C30R* | 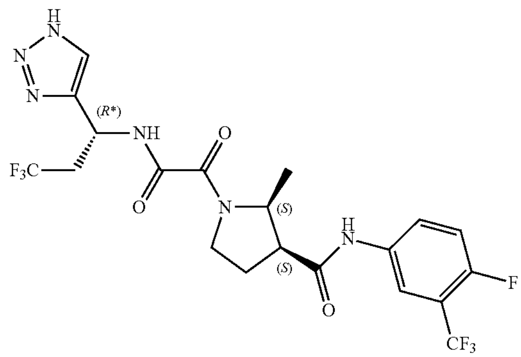 | (Stationary phase: Chiralpak Daicel IG 20 x 250 mm, Mobile phase: $CO_2$, EtOH + 0.4 iPrNH$_2$) |
| C30S* | 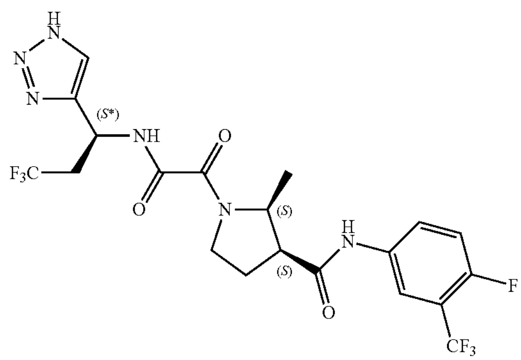 | (Stationary phase: Chiralpak Daicel IG 20 x 250 mm, Mobile phase: $CO_2$, EtOH + 0.4 iPrNH$_2$) |
| C25R* | 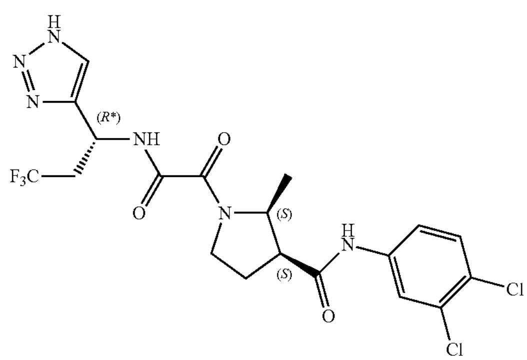 | (Stationary phase: Chiralpak Daicel IG 20 x 250 mm, Mobile phase: $CO_2$, MeOH + 0.4 iPrNH$_2$) |
| C25S* | 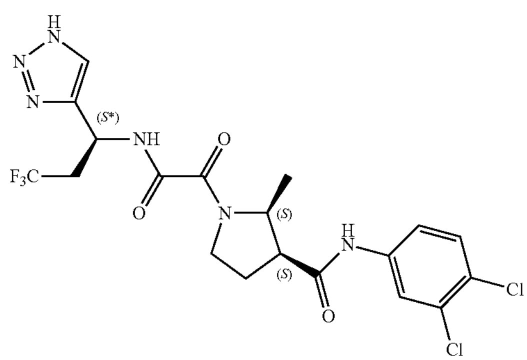 | (Stationary phase: Chiralpak Daicel IG 20 x 250 mm, Mobile phase: $CO_2$, MeOH + 0.4 iPrNH$_2$) |

-continued
| Co. No. | Structure | Method |
|---|---|---|
| C28R* | 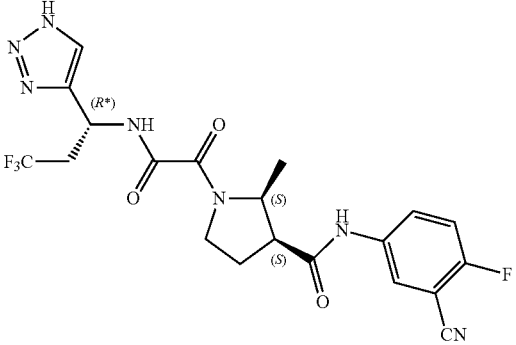 | (Stationary phase: Chiralpak Daicel IC 20 x 250 mm, Mobile phase: $CO_2$, iPrOH + 0.4 iPrNH$_2$) |
| C28S* | 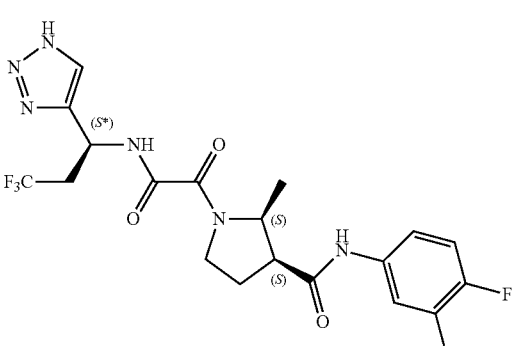 | (Stationary phase: Chiralpak Daicel IC 20 x 250 mm, Mobile phase: $CO_2$, iPrOH + 0.4 iPrNH$_2$) |
| C29R* | 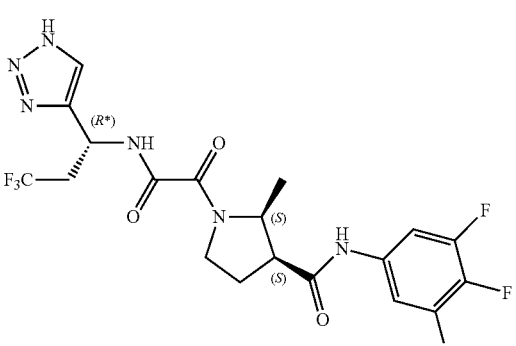 | (Stationary phase: Chiralpak Daicel IG 20 x 250 mm, Mobile phase: $CO_2$, EtOH + 0.4 iPrNH$_2$) |
| C29S* | 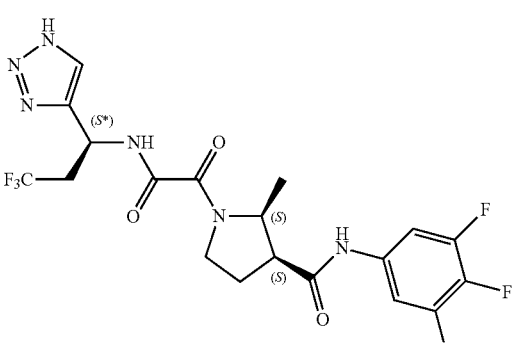 | (Stationary phase: Chiralpak Daicel IG 20 x 250 mm, Mobile phase: $CO_2$, EtOH + 0.4 iPrNH$_2$) |

| Co. No. | Structure | Method |
|---|---|---|
| C31R* | 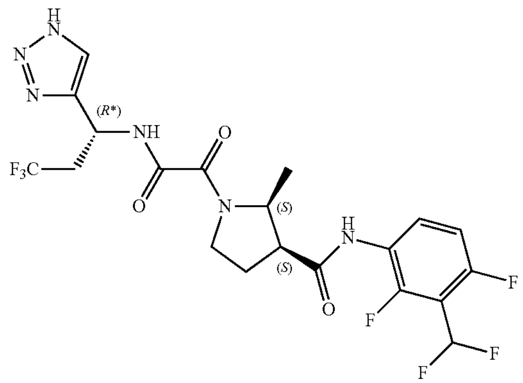 | (Stationary phase: Chiralpak Daicel AD 20 x 250 mm, Mobile phase: $CO_2$, MeOH + 0.4 iPrNH$_2$) |
| C31S* | 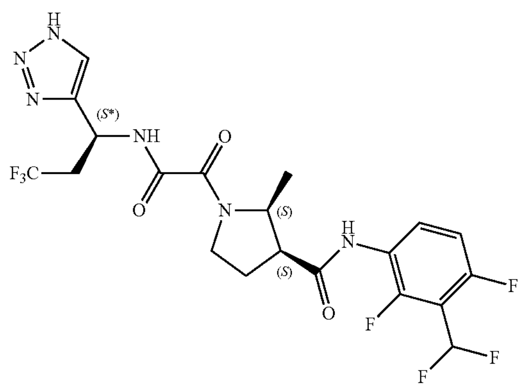 | (Stationary phase: Chiralpak Daicel AD 20 x 250 mm, Mobile phase: $CO_2$, MeOH + 0.4 iPrNH$_2$) |
| C32R* | 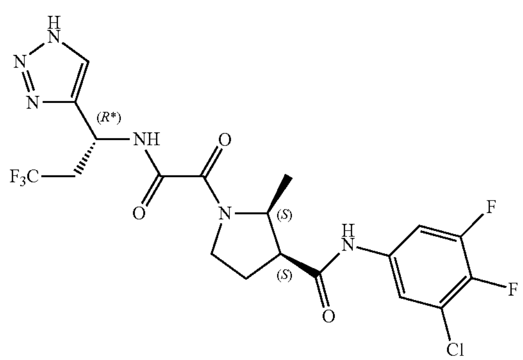 | (Stationary phase: Chiralpak Daicel IG 20 x 250 mm, Mobile phase: $CO_2$, EtOH + 0.4 iPrNH$_2$) |
| C32S* | 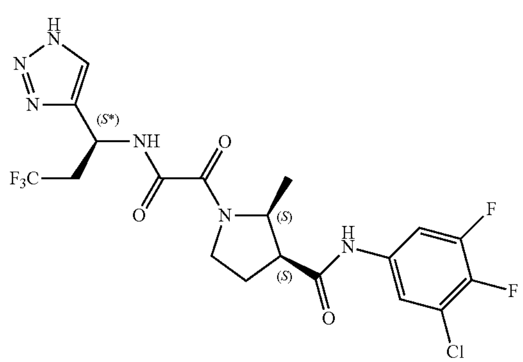 | (Stationary phase: Chiralpak Daicel IG 20 x 250 mm, Mobile phase: $CO_2$, EtOH + 0.4 iPrNH$_2$) |

-continued

| Co. No. | Structure | Method |
|---|---|---|
| C34R* | 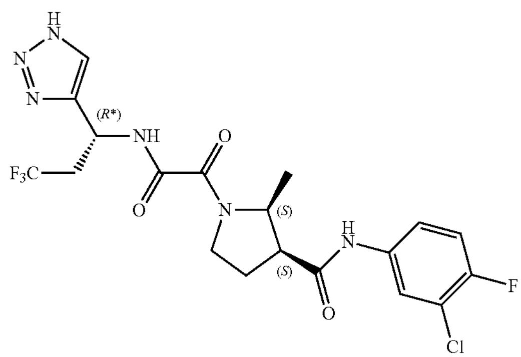 | (Stationary phase: Chiralpak Daicel IG 20 x 250 mm, Mobile phase: $CO_2$, MeOH + 0.4 $iPrNH_2$) |
| C34S* | 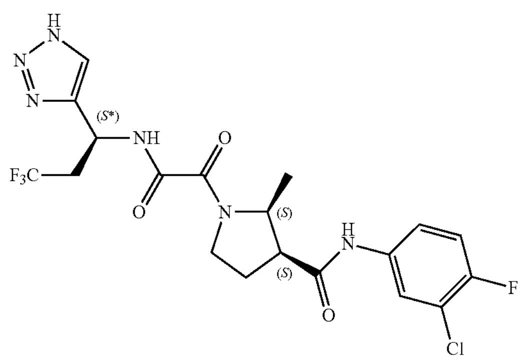 | (Stationary phase: Chiralpak Daicel IG 20 x 250 mm, Mobile phase: $CO_2$, MeOH + 0.4 $iPrNH_2$) |
| C37R* | 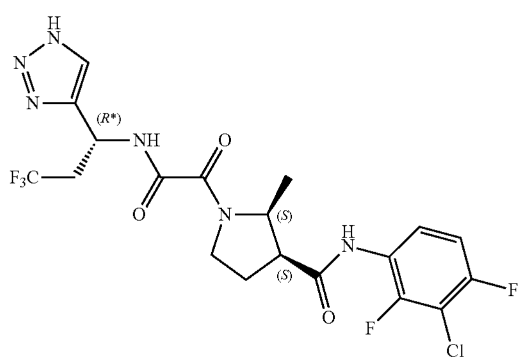 | (Stationary phase: Chiralpak Daicel IC 20 x 250 mm, Mobile phase: $CO_2$, EtOH + 0.4 $iPrNH_2$) |
| C37S* | 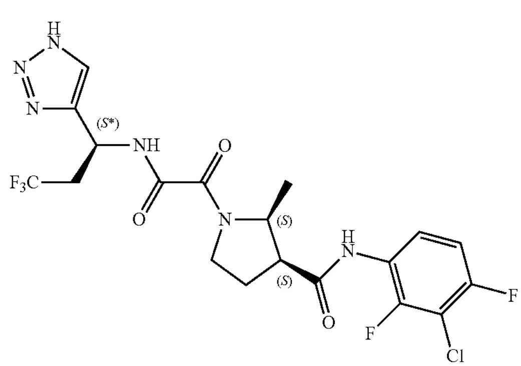 | (Stationary phase: Chiralpak Daicel IC 20 x 250 mm, Mobile phase: $CO_2$, EtOH + 0.4 $iPrNH_2$) |

-continued

| Co. No. | Structure | Method |
|---|---|---|
| C33R* | (structure) | (Stationary phase: Chiralpak Daicel AD 20 x 250 mm, Mobile phase: $CO_2$, MeOH + 0.4 iPrNH$_2$) |
| C33S* | (structure) | (Stationary phase: Chiralpak Daicel AD 20 x 250 mm, Mobile phase: $CO_2$, MeOH + 0.4 iPrNH$_2$) |
| C39t | (structure) Trans | (Stationary phase: Chiralpak Daicel IC 20 x 250 mm, Mobile phase: $CO_2$, EtOH + 0.4 iPrNH$_2$) |
| C39c | (structure) Cis | (Stationary phase: Chiralpak Daicel IC 20 x 250 mm, Mobile phase: $CO_2$, EtOH + 0.4 iPrNH$_2$) |

3.3. LCMS Data

| Co. No. | Rt (min) | [M + H]$^+$ | [M − H]$^−$ | LCMS Method |
|---|---|---|---|---|
| C3' | 1.72 | 487 | 485 | B |
| C6' | 1.54 | 476 | 474 | D |
| C7 | 9.4 | 487 | | C |
| C8 | 9.3 | 489 | | C |
| C9 | 9.4 | 487 | | C |
| C10 | 9.2 | 487 | | C |
| C11 | 7.8 | 454 | | C |
| C12 | 7.7 | 470 | | C |
| C13 | 1.6 | 476 | 474 | B |
| C14 | 9 | 519 | | C |
| C15 | 9.8 | 501 | | C |
| C16 | 9.8 | 503 | | C |
| C17 | 9.2 | 503 | | C |
| C18 | 9.6 | 519 | | C |
| C19 | 9.3 | 487 | | C |
| C20 | 9.3 | 485 | | C |
| C21 | 10.6 | 547 | | C |

-continued

| Co. No. | Rt (min) | [M + H]+ | [M − H]− | LCMS Method |
|---|---|---|---|---|
| C22 | 8.9 | 487 | | C |
| C23 | 9 | 483 | | C |
| C24 | 9.7 | 499 | | C |
| C25R* | 1.88 | 507 | 505 | B |
| C25S* | 1.88 | 507 | 505 | B |
| C26 | 10.1 | 522 | | C |
| C27 | 9.4 | 483 | | C |
| C28R* | 1.6 | 482 | 480 | F |
| C28S* | 1.59 | 482 | 480 | F |
| C29R* | 1.77 | 493 | 491 | F |
| C29S* | 1.77 | 493 | 491 | F |
| C30S* | 1.8 | 525 | 523 | F |
| C31R* | 1.68 | 525 | 523 | E |
| C31S* | 1.67 | 525 | 523 | E |
| C32R* | 1.92 | 509 | 507 | B |
| C32S* | 1.86 | 509 | 507 | B |
| C33R* | 1.78 | 489 | 487 | B |
| C33S* | 1.78 | 489 | 487 | B |
| C34R* | 1.75 | 491 | 489 | F |
| C34S* | 1.73 | 491 | 489 | F |
| C30R* | 1.81 | 525 | 523 | F |
| C35 | 9.7 | 501 | | C |
| C36 | 10.0 and 10.2 | 507 | | C |
| C37R* | 1.73 | 509 | 507 | B |
| C37S* | 1.73 | 509 | 507 | B |
| C38 | 1.81 | 501 | 499 | E |
| C39t | 1.79 | 501 | 499 | B |
| C39c | 1.74 | 501 | 499 | B |

3.4. SFC Data

| Co. No. | Rt (min) | [M + H]+ | [M − H]− | SFC_Method |
|---|---|---|---|---|
| C3' | 2.45 | 546 [M + iPrNH2]+ | 485 | SFC_A |
| C13 | 3.19 | 476 | 474 | SFC_B |
| C25R* | 6.75 | 566 [M + iPrNH2]+ | 505 | SFC_E |
| C25S* | 8.14 | 566 [M + iPrNH2]+ | 505 | SFC_E |
| C28R* | 3.08 | 541 [M + iPrNH2]+ | 480 | SFC_D |
| C28S* | 3.25 | 541 [M + iPrNH2]+ | 480 | SFC_D |
| C29R* | 3.99 | 552 [M + iPrNH2]+ | 491 | SFC_F |
| C29S* | 4.61 | 552 [M + iPrNH2]+ | 491 | SFC_F |
| C30S* | 4.08 | | 523 | SFC_G |
| C31R* | 5.81 | 584 [M + iPrNH2]+ | 523 | SFC_C |
| C31S* | 6.92 | 584 [M + iPrNH2]+ | 523 | SFC_C |
| C32R* | 4.93 | 568 [M + iPrNH2]+ | 507 | SFC_F |
| C32S* | 5.65 | 568 [M + iPrNH2]+ | 507 | SFC_F |
| C33R* | 4.12 | 548 [M + iPrNH2]+ | 487 | SFC_C |
| C33S* | 5.67 | 548 [M + iPrNH2]+ | 487 | SFC_C |
| C34R* | 6.17 | 550 [M + iPrNH2]+ | 489 | SFC_E |
| C34S* | 7.28 | 550 [M + iPrNH2]+ | 489 | SFC_E |
| C30R* | 3.56 | | 523 | SFC_G |
| C37R* | 2.03 | | 507 | SFC_H |
| C37S* | 2.13 | | 507 | SFC_H |
| C39t | 2.13 | 560 [M + iPrNH2]+ | | SFC_A |
| C39c | 2.26 | 560 [M + iPrNH2]+ | | SFC_A |

3.5. $^1$H NMR Data

| Co. No. | NMR |
|---|---|
| C3' | $^1$H NMR (400 MHz, DMSO-$d_6$, 27° C.) δ ppm 1.15-1.34 (m, 3 H) 1.93-2.13 (m, 1 H) 2.15-2.30 (m, 1 H) 2.75-2.90 (m, 1 H) 3.09-3.85 (m, 6 H) 4.18-4.66 (m, 1 H) 7.37-7.59 (m, 2 H) 7.61-7.82 (m, 1 H) 9.61-9.74 (m, 1 H) 10.35-10.51 (m, 1 H) 13.45-16.27 (m, 1 H) |
| C6' | $^1$H NMR (600 MHz, DMSO-d6, 87° C.) δ ppm 10.05-10.28 (m, 1 H), 9.24-9.48 (m, 1 H), 8.01-8.09 (m, 1 H), 7.77-7.87 (m, 1 H), 7.59-7.72 (m, 1 H), 7.38-7.46 (m, 1 H), 4.22-4.69 (m, 1 H), 3.37-3.87 (m, 2 H), 3.13-3.29 (m, 4 H), 2.78-2.90 (m, 1 H), 2.13-2.28 (m, 1 H), 1.98-2.12 (m, 1 H), 1.21-1.32 (m, 3 H) (mixture of rotamers) |
| C7 | $^1$H NMR (400 MHz, DMSO-$d_6$, 80° C.) δ ppm 2.02-2.25 (m, 2 H) 3.19-3.38 (m, 5 H) 3.42-4.01 (m, 5 H) 7.47-7.56 (m, 2 H) 7.69 (d, J = 5.6 Hz, 1 H) 7.96 (dd, J = 4.8, 2.0 Hz, 1 H) 9.41 (br s, 1 H) 10.15 (br s, 1 H) 14.42-14.95 (m, 1 H) (mixture of rotamers) |
| C8 | $^1$H NMR (400 MHz, DMSO-$d_6$, 80° C.) δ ppm 2.05-2.24 (m, 2 H) 3.20-3.35 (m, 5 H) 3.43-4.01 (m, 4 H) 7.59-7.68 (m, 2 H) 7.70 (d, J = 6.1 Hz, 1 H) 9.42 (br s, 1 H) 10.21 (br s, 1 H) 14.43-14.97 (m, 1 H) (mixture of rotamers) |
| C9 | $^1$H NMR (400 MHz, DMSO-$d_6$, 80° C.) δ ppm 1.05-1.11 (m, 3 H) 2.39-2.45 (m, 1 H) 2.68-2.83 (m, 1 H) 3.12-4.13 (m, 8 H) 7.50 (dt, J = 10.4, 6.0 Hz, 2 H) 7.69 (d, J = 6.5 Hz, 1 H) 9.42 (br s, 1 H) 10.25 (br s, 1 H) 14.60-14.84 (m, 1 H) (mixture of rotamers) |
| C10 | $^1$H NMR (400 MHz, DMSO-$d_6$, 80° C.) δ ppm 0.94-1.01 (m, 3 H) 2.64-2.68 (m, 1 H) 3.17-4.03 (m, 9 H) 7.45-7.54 (m, 2 H) 7.70 (br s, 1 H) 9.43 (br s, 1 H) 10.18-10.28 (m, 1 H) 14.47-14.82 (m, 1 H) (mixture of rotamers) |
| C11 | $^1$H NMR (400 MHz, DMSO-$d_6$, 80° C.) δ ppm 2.03-2.30 (m, 2 H) 3.17-3.39 (m, 5 H) 3.43-4.02 (m, 4 H) 7.49 (t, J = 4.5 Hz, 1 H) 7.71 (d, J = 5.9 Hz, 1 H) 7.75 (br d, J = 2.9 Hz, 1 H) 8.26 (d, J = 4.9 Hz, 1 H) 9.43 (br s, 1 H) 10.31-10.63 (m, 1 H) 14.51-14.96 (m, 1 H) (mixture of rotamers) |
| C12 | $^1$H NMR (400 MHz, DMSO-$d_6$, 80° C.)) δ ppm 2.03-2.29 (m, 2 H) 3.20-3.37 (m, 5 H) 3.43-4.03 (m, 4 H) 6.83 (t, J = 55.2 Hz, 1 H) 7.62-7.75 (m, 2 H) 7.88-7.97 (m, 1 H) 8.52 (d, J = 5.4 Hz, 1 H) 9.43 (s, 1 H) 10.41-10.54 (m, 1 H) 14.63-14.82 (m, 1 H) (mixture of rotamers) |
| C13 | $^1$H NMR (400 MHz, DMSO-$d_6$, 27° C.) δ ppm 1.18 (dd, J = 24.5, 6.4 Hz, 3 H) 1.99 (s, 1 H) 2.10-2.24 (m, 1 H) 3.10-3.42 (m, 5 H) 3.66 (d, J = 8.8 Hz, 1 H) 3.77-3.96 (m, 1 H) 4.17-4.57 (m, 1 H) 7.50 (td, J = 9.1, 3.6 Hz, 1 H) 7.63 (br s, 1 H) 7.79-7.87 (m, 1 H) 8.06-8.18 (m, 1 H) 9.70 (br d, J = 13.0 Hz, 1 H) 10.46 (d, J = 17.6 Hz, 1 H) 14.63-15.20 (m, 1 H) |
| C14 | $^1$H NMR (400 MHz, DMSO-$d_6$, 80° C.) δ ppm 1.06-1.14 (m, 3 H) 1.96-2.10 (m, 1 H) 2.25-2.38 (m, 1 H) 3.17-3.38 (m, 5 H) 3.43-3.88 (m, 2 H) 4.52-4.96 (m, 1 H) 7.12-7.42 (m, 2 H) 7.68-7.76 (m, 1 H) 7.85-7.94 (m, 1 H) 9.39-9.51 (m, 1 H) 9.74-9.90 (m, 1 H) 14.51-14.99 (m, 1 H) (mixture of rotamers) |

-continued

| Co. No. | NMR |
|---|---|
| C15 | ¹H NMR (400 MHz, DMSO-d₆, 80° C.) δ ppm 1.01-1.09 (m, 3 H) 1.96-2.10 (m, 1 H) 2.33 (br d, J = 10.0 Hz, 1 H) 3.17-3.38 (m, 5 H) 3.40-3.88 (m, 2 H) 4.52-4.93 (m, 1 H) 7.47-7.60 (m, 2 H) 7.72 (br d, J = 3.6 Hz, 1 H) 7.92-8.00 (m, 1 H) 9.37-9.54 (m, 1 H) 10.01-10.17 (m, 1 H) 14.60-14.89 (m, 1 H) (mixture of rotamers) |
| C16 | ¹H NMR (400 MHz, DMSO-d₆, 80° C.) δ ppm 1.00-1.09 (m, 3 H) 1.96-2.10 (m, 1 H) 2.24-2.40 (m, 1 H) 3.17-3.38 (m, 5 H) 3.42-3.89 (m, 2 H) 4.52-4.93 (m, 1 H) 7.59-7.76 (m, 3 H) 9.38-9.55 (m, 1 H) 10.07-10.22 (m, 1 H) 14.57-14.95 (m, 1 H) (mixture of rotamers) |
| C17 | ¹H NMR (400 MHz, DMSO-d₆, 80° C.) δ ppm 1.06-1.14 (m, 3 H) 1.97-2.09 (m, 1 H) 2.26-2.37 (m, 1 H) 3.21-3.37 (m, 5 H) 3.42-3.89 (m, 2 H) 4.52-4.95 (m, 1 H) 7.23-7.32 (m, 1 H) 7.63-7.77 (m, 2 H) 9.37-9.53 (m, 1 H) 9.74-9.89 (m, 1 H) 14.55-14.94 (m, 1 H) (mixture of rotamers) |
| C18 | ¹H NMR (400 MHz, DMSO-d₆, 80° C.) δ ppm 1.01-1.14 (m, 3 H) 1.96-2.10 (m, 1 H) 2.27-2.40 (m, 1 H) 3.21-3.38 (m, 5 H) 3.43-3.90 (m, 2 H) 4.53-4.94 (m, 1H) 7.40-7.49 (m, 1 H) 7.72 (d, J = 4.4 Hz, 1 H) 7.83-7.90 (m, 1 H) 8.03-8.10 (m, 1 H) 9.38-9.53 (m, 1 H) 10.08-10.23 (m, 1 H) 14.49-15.01 (m, 1 H) (mixture of rotamers) |
| C19 | ¹H NMR (400 MHz, DMSO-d₆, 80° C.) δ ppm 1.15-1.26 (m, 3 H) 1.85-2.03 (m, 1 H) 2.15-2.25 (m, 1 H) 3.20-4.00 (m, 7 H) 4.21-4.61 (m, 1 H) 7.43-7.54 (m, 2 H) 7.65-7.76 (m, 1 H) 9.39-9.50 (m, 1 H) 10.17-10.29 (m, 1 H) 14.65-14.80 (m, 1 H) (mixture of rotamers) |
| C20 | ¹H NMR (400 MHz, DMSO-d₆, 80° C.) δ ppm 1.02-1.10 (m, 3 H) 1.96-2.09 (m, 1 H) 2.28-2.39 (m, 1 H) 3.16-3.39 (m, 5 H) 3.43-3.90 (m, 2 H) 4.51-4.92 (m, 1 H) 7.33 (td, J = 9.1, 2.9 Hz, 1 H) 7.45-7.53 (m, 1 H) 7.72 (d, J = 3.6 Hz, 1 H) 7.84-7.92 (m, 1 H) 9.38-9.53 (m, 1 H) 9.94-10.07 (m, 1 H) 14.65-14.85 (m, 1 H) (mixture of rotamers) |
| C3' | 1H NMR (400 MHz, DMSO-d6, 27° C.) d ppm 1.15-1.34 (m, 3 H) 1.93-2.13 (m, 1 H) 2.15-2.30 (m, 1 H) 2.75-2.90 (m, 1 H) 3.09-3.85 (m, 6 H) 4.18-4.66 (m, 1 H) 7.37-7.59 (m, 2 H) 7.61-7.82 (m, 1 H) 9.61-9.74 (m, 1 H) 10.35-10.51 (m, 1 H) 13.45-16.27 (m, 1 H) (mixture of rotamers) |
| C21 | ¹H NMR (400 MHz, DMSO-d₆, 70° C.) δ ppm 1.00-1.09 (m, 3 H) 1.97-2.08 (m, 1 H) 2.28-2.38 (m, 1 H) 3.15-3.37 (m, 5 H) 3.76 (m, J = 149.2 Hz, 2 H) 4.51-4.92 (m, 1 H) 7.71 (br d, J = 4.3 Hz, 3 H) 9.39-9.54 (m, 1H) 10.05-10.22(m, 1 H) 14.48-15.04 (m, 1 H) (mixture of rotamers) |
| C22 | ¹H NMR (400 MHz, DMSO-d₆, 70° C.) δ ppm 1.06-1.13 (m, 3 H) 1.97-2.08 (m, 1 H) 2.26-2.36 (m, 1 H) 3.18-3.35 (m, 5 H) 3.43-3.87 (m, 2 H) 4.52-4.93 (m, 1 H) 7.21-7.31 (m, 1 H) 7.44-7.53 (m, 1 H) 7.72 (d, J = 2.4 Hz, 1 H) 9.40-9.52 (m, 1 H) 9.79-9.91 (m, 1 H) 14.62-14.87 (m, 1 H) (mixture of rotamers) |
| C23 | ¹H NMR (400 MHz, DMSO-d₆) δ ppm 1.01-1.08 (m, 3 H) 1.92-2.02 (m, 1 H) 2.17 (br s, 3 H) 2.23-2.34 (m, 1 H) 3.16-3.29 (m, 5 H) 3.41-3.86 (m, 2 H) 4.49-4.88 (m, 1 H) 6.99-7.07 (m, 1 H) 7.50 (q, J = 7.9 Hz, 1 H) 7.75 (br d, J = 7.0 Hz, 1 H) 9.68-9.85 (m, 2 H) 14.81-15.03 (m, 1 H) (mixture of rotamers) |
| C24 | ¹H NMR (400 MHz, DMSO-d₆) δ ppm 0.95-1.04 (m, 3 H) 1.92-2.03 (m, 1 H) 2.26 (t, J = 2.3 Hz, 3 H) 2.27-2.35 (m, 1 H) 3.08-3.29 (m, 5 H) 3.40-3.86 (m, 2 H) 4.47-4.87 (m, 1 H) 7.34-7.40 (m, 1 H) 7.68-7.79 (m, 2 H) 9.67-9.80 (m, 1 H) 10.08-10.18 (m, 1 H) 14.84-14.99 (m, 1 H) (mixture of rotamers) |
| C25R* | ¹H NMR (400 MHz, DMSO-d6, 100° C.) d ppm 1.05 (d, J = 6.8 Hz, 3 H) 1.89-2.09 (m, 1 H) 2.21-2.38 (m, 1 H) 2.80-3.30 (m, 3 H) 3.40-3.99 (m, 2 H) 4.48-5.11 (m, 1 H) 5.33-5.54 (m, 1 H) 7.43-7.59 (m, 2 H) 7.75 (s, 1 H) 7.88-7.99 (m, 1 H) 8.82-9.13 (m, 1 H) 9.84-10.14 (m, 1 H) (mixture of rotamers) |
| C25S* | ¹H NMR (400 MHz, DMSO-d6, 100° C.) d ppm 1.03 (br dd, J = 23.1, 6.5 Hz, 3 H) 1.91-2.11 (m, 1 H) 2.18-2.38 (m, 1 H) 2.85-3.96 (m, 5 H) 4.48-5.08 (m, 1 H) 5.35-5.54 (m, 1 H) 7.47-7.53 (m, 2 H) 7.70-7.79 (m, 1 H) 7.92 (s, 1 H) 8.86-9.10 (m, 1 H) 9.90-10.06 (m, 1 H) (mixture of rotamers) |
| C26 | ¹H NMR (400 MHz, DMSO-d₆, 80° C.) δ ppm 0.97-1.09 (m, 3 H) 1.97-2.08 (m, 1 H) 2.26-2.37 (m, 1 H) 3.18-4.10 (m, 7 H) 4.51-4.94 (m, 1 H) 7.49 (dt, J = 10.1, 5.2 Hz, 2 H) 9.41-9.57 (m, 1 H) 10.07-10.18 (m, 1 H) 14.79-15.14 (m, 1 H) (mixture of rotamers) |
| C27 | ¹H NMR (400 MHz, DMSO-d₆) δ ppm 0.95-1.04 (m, 3 H) 1.92-2.04 (m, 1 H) 2.25-2.38 (m, 4 H) 3.07-3.28 (m, 5 H) 3.43-3.86 (m, 2 H) 4.48-4.87 (m, 1 H) 7.20 (br t, J = 6.7 Hz, 1 H) 7.57 (dtd, J = 12.9, 6.6, 6.6, 2.5 Hz, 1 H) 7.75 (br d, J = 8.3 Hz, 1 H) 9.67-9.80 (m, 1 H) 10.10-10.21 (m, 1 H) 14.80-15.05 (m, 1 H) (mixture of rotamers) |
| C28R* | ¹H NMR (400 MHz, DMSO-d6, 27° C.) d ppm 0.95-1.07 (m, 3 H) 1.86-2.13 (m, 1 H) 2.24-2.39 (m, 1 H) 2.69-4.07 (m, 5 H) 4.47-5.15 (m, 1 H) 5.34-5.57 (m, 1 H) 7.44-7.60 (m, 1 H) 7.71-7.95 (m, 2 H) 8.03-8.23 (m, 1 H) 9.24-9.49 (m, 1 H) 10.24-10.53 (m, 1 H) (mixture of rotamers) |
| C28S* | ¹H NMR (400 MHz, DMSO-d6, 27° C.) d ppm 0.94-1.04 (m, 3 H) 1.91-2.08 (m, 1 H) 2.23-2.38 (m, 1 H) 2.90-3.95 (m, 5 H) 4.47-5.09 (m, 1 H) 5.36-5.51 (m, 1 H) 7.44-7.54 (m, 1 H) 7.75-7.91 (m, 2 H) 8.07-8.17 (m, 1 H) 9.25-9.51 (m, 1 H) 10.31-10.51 (m, 1 H) 13.83-15.57 (m, 1 H) (mixture of rotamers) |
| C29R* | ¹H NMR (400 MHz, DMSO-d6, 27° C.) d ppm 0.96-1.03 (m, 3 H) 1.91-2.07 (m, 1 H) 2.20-2.38 (m, 1 H) 2.75-4.04 (m, 5 H) 4.48-5.10 (m, 1 H) 5.37-5.53 (m, 1 H) 7.42-7.59 (m, 2 H) 7.77-7.89 (m, 1 H) 9.26-9.46 (m, 1 H) 10.28-10.50 (m, 1 H) (mixture of rotamers) |

| Co. No. | NMR |
|---|---|
| C29S* | ¹H NMR (400 MHz, DMSO-d6, 27° C.) d ppm 0.90-1.03 (m, 3 H) 1.91-2.06 (m, 1 H) 2.19-2.39 (m, 1 H) 2.88-3.94 (m, 5 H) 4.48-5.11 (m, 1 H) 5.36-5.52 (m, 1 H) 7.43-7.58 (m, 2 H) 7.75-7.91 (m, 1 H) 9.26-9.46 (m, 1 H) 10.28-10.49 (m, 1 H) (mixture of rotamers) |
| C30S* | ¹H NMR (400 MHz, DMSO-d6, 27° C.) d ppm 0.93-1.06 (m, 3 H) 1.92-2.08 (m, 1 H) 2.24-2.39 (m, 1 H) 2.90-3.97 (m, 5 H) 4.50-5.10 (m, 1 H) 5.38-5.51 (m, 1 H) 7.42-7.54 (m, 1 H) 7.73-7.90 (m, 2 H) 8.06-8.14 (m, 1 H) 9.28-9.46 (m, 1 H) 10.28-10.44 (m, 1 H) (mixture of rotamers) |
| C31R* | ¹H NMR (400 MHz, DMSO-d6, 27° C.) d ppm 1.00-1.10 (m, 3 H) 1.90-2.06 (m, 1 H) 2.18-2.39 (m, 1 H) 2.86-4.00 (m, 5 H) 4.50-5.13 (m, 1 H) 5.37-5.53 (m, 1 H) 7.14-7.54 (m, 2 H) 7.78-8.00 (m, 2 H) 9.22-9.51 (m, 1 H) 9.89-10.32 (m, 1 H) 13.91-16.26 (m, 1 H) (mixture of rotamers) |
| C31S* | ¹H NMR (400 MHz, DMSO-d6, 27° C.) d ppm 0.97-1.11 (m, 3 H) 1.91-2.06 (m, 1 H) 2.18-2.37 (m, 1 H) 2.88-3.96 (m, 5 H) 4.50-5.08 (m, 1 H) 5.37-5.50 (m, 1 H) 7.13-7.56 (m, 2 H) 7.79-7.84 (m, 1 H) 7.85-7.94 (m, 1 H) 9.27-9.45 (m, 1 H) 9.95-10.14 (m, 1 H) (mixture of rotamers) |
| C32R* | ¹H NMR (400 MHz, DMSO-d6, 27° C.) d ppm 0.93-1.05 (m, 3 H) 1.87-2.07 (m, 1 H) 2.20-2.39 (m, 1 H) 2.85-3.99 (m, 5 H) 4.49-5.13 (m, 1 H) 5.37-5.53 (m, 1 H) 7.52-7.72 (m, 2 H) 7.75-7.93 (m, 1 H) 9.23-9.46 (m, 1 H) 10.27-10.50 (m, 1 H) (mixture of rotamers) |
| C32S* | ¹H NMR (400 MHz, DMSO-d6, 27° C.) d ppm 0.91-1.05 (m, 3 H) 1.90-2.08 (m, 1 H) 2.19-2.39 (m, 1 H) 2.89-3.95 (m, 5 H) 4.42-5.07 (m, 1 H) 5.37-5.50 (m, 1 H) 7.58-7.70 (m, 2 H) 7.78-7.89 (m, 1 H) 9.12-9.56 (m, 1 H) 10.36 (br d, J = 30.8 Hz, 1 H) (mixture of rotamers) |
| C33R* | ¹H NMR (400 MHz, DMSO-d6, 27° C.) d ppm 0.90-1.07 (m, 3 H) 1.62-1.76 (m, 3 H) 1.90-2.06 (m, 1 H) 2.17-2.38 (m, 1 H) 2.65-2.92 (m, 2 H) 3.07-3.90 (m, 3 H) 4.43-4.95 (m, 1 H) 6.03 (tdt, J = 55.7, 55.7, 7.1, 4.5, 4.5 Hz, 1 H) 7.42-7.56 (m, 2 H) 7.82 (s, 1 H) 8.74-8.92 (m, 1 H) 10.28-10.44 (m, 1 H) (mixture of rotamers) |
| C33S* | ¹H NMR (400 MHz, DMSO-d6, 27° C.) d ppm 0.92-1.04 (m, 3 H) 1.61-1.76 (m, 3 H) 1.91-2.05 (m, 1 H) 2.17-2.37 (m, 1 H) 2.62-2.93 (m, 2 H) 3.05-3.91 (m, 3 H) 4.43-5.00 (m, 1 H) 5.82-6.27 (m, 1 H) 7.40-7.58 (m, 2 H) 7.82 (s, 1 H) 8.60-9.08 (m, 1 H) 10.20-10.71 (m, 1 H) (mixture of rotamers) |
| C34R* | ¹H NMR (400 MHz, DMSO-d6, 27° C.) d ppm 0.97-1.05 (m, 3 H) 1.89-2.07 (m, 1 H) 2.21-2.39 (m, 1 H) 2.87-3.08 (m, 2 H) 3.08-3.26 (m, 1 H) 3.38-3.98 (m, 2 H) 4.48-5.10 (m, 1 H) 5.33-5.57 (m, 1 H) 7.31-7.42 (m, 1 H) 7.42-7.52 (m, 1 H) 7.76-7.88 (m, 1 H) 7.89-7.96 (m, 1 H) 9.29-9.45 (m, 1 H) 10.17-10.30 (m, 1 H) 14.04-15.92 (m, 1 H) (mixture of rotamers) |
| C34S* | ¹H NMR (400 MHz, DMSO-d6, 27° C.) d ppm 0.92-1.06 (m, 3 H) 1.89-2.06 (m, 1 H) 2.19-2.41 (m, 1 H) 2.89-3.94 (m, 5 H) 4.48-5.05 (m, 1 H) 5.38-5.49 (m, 1 H) 7.33-7.41 (m, 1 H) 7.43-7.52 (m, 1 H) 7.77-7.85 (m, 1 H) 7.89-7.97 (m, 1 H) 9.23-9.58 (m, 1 H) 10.09-10.42 (m, 1 H) (mixture of rotamers) |
| C30R* | ¹H NMR (400 MHz, DMSO-d6, 27° C.) d ppm 0.99-1.03 (m, 3 H) 1.91-2.07 (m, 1 H) 2.19-2.41 (m, 1 H) 2.87-3.09 (m, 2 H) 3.10-3.99 (m, 3 H) 4.48-5.14 (m, 1 H) 5.35-5.55 (m, 1 H) 7.48 (t, J = 9.8 Hz, 1 H) 7.78-7.90 (m, 2 H) 8.06-8.14 (m, 1 H) 9.20-9.58 (m, 1 H) 10.17-10.58 (m, 1 H) 13.70-16.12 (m, 1 H) (mixture of rotamers) |
| C35 | ¹H NMR (400 MHz, DMSO-d₆, 80° C.) δ ppm 0.93-1.24 (m, 6 H) 1.62-1.76 (m, 1 H) 2.39-2.47 (m, 1 H) 3.19-4.98 (m, 7 H) 7.44-7.52 (m, 2 H) 7.67-7.74 (m, 1 H) 9.39-9.48 (m, 1 H) 10.07-10.20 (m, 1 H) 14.62-14.85 (m, 1 H) (mixture of rotamers) |
| C36 | ¹H NMR (400 MHz, DMSO-d₆, 80° C.) δ ppm 0.89-1.24 (m, 6 H) 1.61-1.79 (m, 1 H) 2.40-2.47 (m, 1 H) 2.93-3.02 (m, 2 H) 3.27-3.48 (m, 1 H) 4.18-5.17 (m, 2 H) 5.46 (td, J = 8.7, 4.9 Hz, 1 H) 7.45-7.52 (m, 2 H) 7.72-7.82 (m, 1 H) 9.04-9.13 (m, 1 H) 10.06-10.23 (m, 1 H) 14.71-14.86 (m, 1 H) (mixture of rotamers) |
| C37R* | ¹H NMR (400 MHz, DMSO-d6, 80° C.) d ppm 1.05-1.11 (m, 3 H) 1.91-2.08 (m, 1 H) 2.18-2.38 (m, 1 H) 2.61-4.04 (m, 5 H) 4.46-5.16 (m, 1 H) 5.34-5.53 (m, 1 H) 7.20-7.30 (m, 1 H) 7.60-7.70 (m, 1 H) 7.77 (s, 1 H) 8.94-9.20 (m, 1 H) 9.49-10.33 (m, 1 H) (mixture of rotamers) |
| C37S* | ¹H NMR (400 MHz, DMSO-d6, 80° C.) d ppm 0.99-1.14 (m, 3 H) 1.92-2.11 (m, 1 H) 2.19-2.39 (m, 1 H) 2.86-4.12 (m, 5 H) 4.47-5.08 (m, 1 H) 5.44 (qd, J = 8.4, 5.1 Hz, 1 H) 7.25 (if, J = 9.0, 2.2 Hz, 1 H) 7.65 (tt, J = 8.8, 5.5 Hz, 1 H) 7.77 (d, J = 4.7 Hz, 1 H) 9.09 (br dd, J = 28.5, 8.8 Hz, 1 H) 9.82 (br d, J = 18.9 Hz, 1 H) 14.19-15.52 (m, 1 H) (mixture of rotamers) |
| C38 | ¹H NMR (400 MHz, DMSO-d6, 80° C.) d ppm 0.94-1.11 (m, 3 H) 1.94-2.09 (m, 1 H) 2.21-2.37 (m, 4 H) 3.09-3.87 (m, 7 H) 4.47-4.91 (m, 1 H) 7.43-7.56 (m, 2 H) 9.17-9.61 (m, 1 H) 9.73-10.85 (m, 1 H) (mixture of rotamers) |
| C39t | ¹H NMR (400 MHz, METHANOL-d4, 27° C.) d ppm 1.07-1.21 (m, 3 H) 1.98-2.16 (m, 1 H) 2.34-2.57 (m, 1 H) 2.62-2.82 (m, 4 H) 2.89-3.06 (m, 1 H) 3.09-3.27 (m, 1 H) 3.49-4.05 (m, 2 H) 4.49-5.02 (m, 1 H) 5.96 (if, J = 57.11, 4.51 Hz, 1 H) 7.34-7.47 (m, 2 H) 7.71 (br s, 1 H) (mixture of rotamers) |
| C39c | ¹H NMR (400 MHz, DMSO-d6, 100° C.) d ppm 0.96-1.11 (m, 3 H) 1.90-2.10 (m, 1 H) 2.20-2.38 (m, 1 H) 2.99 (s, 6 H) 3.38-3.90 (m, 2 H) 4.44-5.02 (m, 1 H) 6.07 (td, J = 57.22, 3.96 Hz, 1 H) 7.38-7.56 (m, 2 H) 7.70 (s, 1 H) 8.90-9.12 (m, 1 H) 10.03-10.21 (m, 1 H) 13.20-15.57 (m, 1 H) (mixture of rotamers) |

4. Anti-HBV Activity of Compounds of Formula (I)

The anti HBV activity was measured using the HepG2.117 cell line, a stable, inducible HBV producing cell line, which replicates HBV in the absence of doxicycline (Tet-off system). The HepG2 cell line is available from ATCC® under number HB-8065. Transfection of the HepG2 cell line can be as described in Sun and Nassal 2006 Journal of Hepatology 45 (2006) 636-645 "Stable HepG2- and Huh7-based human hepatoma cell lines for efficient regulated expression of infectious hepatitis B virus".

For the antiviral assay, HBV replication was induced, followed by a treatment with serially diluted compound in 96-well plates. After 3 days of treatment, the antiviral activity was determined by quantification of intracellular HBV DNA using real-time PCR and an HBV specific primer set and probe.

Cytotoxicity of the compounds was tested using HepG2 or HepG2.117 cells, incubated for 3 days in the presence of compounds. The viability of the cells was assessed using the Perkin Elmer ATPlite Luminescence Assay System."

Results

TABLE 4

| Compound number | HBV-AVE-HepG2.117 $EC_{50}$ (μM; mean value) | TOX-HepG2.117 $CC_{50}$ (μM; mean value) |
| --- | --- | --- |
| C1 | 0.15 | >50 |
| C1•HCl | 0.27 | >50 |
| C2 | 0.079 | >50 |
| C3 | 0.011 | >50 |
| C3' | >2.5 | >50 |
| C4 | 0.053 | >50 |
| C5 | 0.040 | >50 |
| C6 | 0.044 | >50 |
| C6' | 2.906 | >50 |
| C7 | 0.100 | >50 |
| C8 | 0.045 | >50 |
| C9 | 0.204 | >50 |
| C10 | 0.578 | >50 |
| C11 | 1.499 | >50 |
| C12 | 1.286 | >50 |
| C13 | 0.061 | >50 |
| C14 | 0.019 | >50 |
| C15 | 0.014 | 35.2 |
| C16 | 0.006 | >50 |
| C17 | 0.010 | >50 |
| C18 | 0.012 | >50 |
| C19 | 0.019 | >50 |
| C20 | 0.012 | >50 |
| C3' | >2.5 | >50 |
| C21 | 0.012 | >50 |
| C22 | 0.026 | >50 |
| C23 | 0.016 | >50 |
| C24 | 0.012 | >50 |
| C25R* | 0.017 | 25.7 |
| C25S* | 0.074 | >50 |
| C26 | 0.176 | >50 |
| C27 | 0.012 | >50 |
| C28R* | 0.032 | >50 |
| C28S* | 0.070 | >50 |
| C29R* | 0.014 | >50 |
| C29S* | 0.042 | >50 |
| C30S* | 0.060 | >50 |
| C31R* | 0.021 | >50 |
| C31S* | 0.056 | >50 |
| C32R* | 0.007 | >50 |
| C32S* | 0.031 | >50 |
| C33R* | 0.034 | >50 |
| C33S* | 0.040 | >50 |
| C34R* | 0.003 | >50 |
| C34S* | 0.035 | >50 |
| C30R* | 0.037 | >50 |
| C35 | 0.011 | >50 |
| C36 | <0.010 | >50 |
| C37R* | 0.014 | >50 |

TABLE 4-continued

| Compound number | HBV-AVE-HepG2.117 $EC_{50}$ (μM; mean value) | TOX-HepG2.117 $CC_{50}$ (μM; mean value) |
| --- | --- | --- |
| C37S* | 0.043 | >50 |
| C38 | 0.012 | >50 |
| C39t | 0.033 | >50 |
| C39c | 0.062 | >50 |

Induction or Non-Induction of HBc Speckling

HepG2.117 cells were cultured in the presence of DMSO or test compound in absence of doxycycline.

After formaldehyde fixation and Triton-X-100 permeabilization, Hepatitis B virus core protein (HBc) was immunolabeled with a primary anti-HBc antibody. ALEXA 488-conjugated secondary antibody was used for fluorescent detection of the primary HBV Core signal. CELLMASK Deep Red and HOECHST 33258 were used for the detection of cytoplasm and nucleus respectively, which allowed the segmentation of cellular compartments.

An image analysis software that allows to detect different morphological phenotypes was used to determine the level of HBV core in the cytoplasm or nucleus (high content imaging assay).

The invention claimed is:

1. A compound of formula (I)

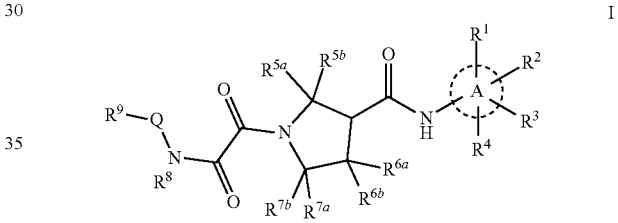

including the stereoisomers or tautomeric forms thereof, wherein:

Ⓐ represents a 6-membered aryl ring optionally containing one or more heteroatom(s), the heteroatom or each of the heteroatoms being nitrogen;

$R^1$, $R^2$ and $R^3$ are each independently selected from the group consisting of H, F, Cl, Br, $CHF_2$, $CH_2F$, $CF_3$, CN, $C_{1-4}$alkyl and $C_{3-6}$cycloalkyl;

$R^4$ is selected from the group consisting of H and F;

$R^{5a}$ and $R^{5b}$ are each independently selected from the group consisting of H, $C_{1-4}$alkyl optionally substituted with one or more F, and $C_{3-6}$cycloalkyl optionally substituted with one or more F;

$R^{6a}$ and $R^{6b}$ are each independently selected from the group consisting of H, $C_{1-4}$alkyl optionally substituted with one or more F, and $C_{3-6}$cycloalkyl optionally substituted with one or more F;

$R^{7a}$ and $R^{7b}$ are each independently selected from the group consisting of H, $C_{1-4}$alkyl optionally substituted with one or more F, and $C_{3-6}$cycloalkyl optionally substituted with one or more F;

Q is selected from the group consisting of
$C_{1-5}$alkyl, optionally substituted with one or more substituents selected from the group consisting of halogen;
$C_{2-3}$alkenyl substituted with halogen,
3- to 6-membered monocyclic saturated rings,
up to 9-membered polycyclic saturated rings, wherein the (3- to 6-membered monocyclic or up to 9-membered polycyclic) saturated rings:
optionally and independently contain one or more heteroatoms, the heteroatoms being independently selected from N, O and S, and/or
are optionally and independently substituted with one or more substituents selected from the group consisting of F, oxo, OH, C(=O)NHCH$_3$ and C$_{1-4}$alkyl optionally substituted with one or more F;
$R^8$ is H;
$R^9$ is selected from the group consisting of
phenyl,
phenyl substituted with one or more substituents each independently selected from the group consisting of halogen, CN, CF$_3$, CF$_2$H, CH$_2$F, C$_{1-4}$alkyl, C$_{3-6}$cycloalkyl, OH and OC$_{1-4}$alkyl,
pyridyl,
pyridyl substituted with one or more substituents each independently selected from the group consisting of halogen, CN, CF$_3$, CF$_2$H, CH$_2$F, C$_{1-4}$alkyl, C$_{3-6}$cycloalkyl, OH and OC$_{1-4}$alkyl,
pyrimidyl,
pyrimidyl substituted with one or more substituents each independently selected from the group consisting of halogen, CN, CF$_3$, CF$_2$H, CH$_2$F, C$_{1-4}$alkyl, C$_{3-6}$cycloalkyl, OH and OC$_{1-4}$alkyl,
pyrazinyl,
pyrazinyl substituted with one or more substituents each independently selected from the group consisting of halogen, CN, CF$_3$, CF$_2$H, CH$_2$F, C$_{1-4}$alkyl, C$_{3-6}$cycloalkyl, OH and OC$_{1-4}$alkyl,
pyridazinyl,
pyridazinyl substituted with one or more substituents each independently selected from the group consisting of halogen, CN, CF$_3$, CF$_2$H, CH$_2$F, C$_{1-4}$alkyl, C$_{3-6}$cycloalkyl, OH and OC$_{1-4}$alkyl,
5-membered unsaturated heterocycles containing one to 4 heteroatoms, the heteroatoms being each independently selected from N, O and S, and
5-membered unsaturated heterocycles containing one to 4 heteroatoms, the heteroatoms being each independently selected from N, O and S, substituted with one or more substituents selected from the group consisting of halogen, CN, CF$_3$, CF$_2$H, CH$_2$F, C$_{1-4}$alkyl, C$_{3-6}$cycloalkyl, OH and OC$_{1-4}$alkyl;
or a pharmaceutically acceptable salt or a solvate thereof.

2. The compound of claim 1, wherein Q is C$_{1-5}$alkyl substituted with one or more substituents selected from the group consisting of halogen; or is a 3- to 6-membered monocyclic saturated ring optionally containing one or more heteroatoms, the heteroatoms being independently selected from N, O and S, and optionally substituted with one or more substituents selected from the group consisting of F, oxo, OH, C(=O)NHCH$_3$, C$_{1-4}$alkyl, and C$_{1-4}$alkyl substituted with one or more F.

3. The compound of claim 1, wherein Q is a 3-6 membered monocyclic saturated ring optionally containing one or more heteroatoms, the heteroatoms being independently selected from N, O and S, and wherein Q is substituted with one or more substituents selected from the group consisting of F, oxo, OH, C(=O)NHCH$_3$, and C$_{1-4}$alkyl optionally substituted with one or more F.

4. The compound of claim 1, wherein $R^9$ is a 5-membered unsaturated heterocycle containing one to four heteroatoms, the heteroatoms being selected from N, O and S, and optionally substituted with one or more substituents selected from the group consisting of halogen, CN, CF$_3$, CF$_2$H, CHF$_2$, C$_{1-4}$alkyl, C$_{3-6}$cycloalkyl, OH and OC$_{1-4}$alkyl.

5. The compound of claim 1, wherein $R^1$, $R^2$ and $R^3$ are each independently selected from the group consisting of H, F, Cl, Br, CHF$_2$, CF$_3$, CN, and C$_{1-4}$alkyl; and $R^4$ is H or F.

6. The compound of claim 1, wherein (A) represents phenyl.

7. The compound of claim 1, wherein Q is cyclobutyl substituted with one or more fluorine.

8. The compound of claim 1, wherein
(A) represents phenyl;
$R^1$, $R^2$ and $R^3$ are each independently selected from the group consisting of H, F, Cl, Br, CHF$_2$, CF$_3$, CN, and C$_{1-4}$alkyl;
$R^4$ is H or F;
$R^{5a}$ and $R^{5b}$ are each independently selected from the group consisting of H and methyl;
$R^{6a}$ and $R^{6b}$ are each independently selected from the group consisting of H and methyl;
$R^{7a}$ and $R^{7b}$ are each independently selected from the group consisting of H and methyl;
Q is selected from the group consisting of CH$_2$CF$_3$ and 3,3-difluorocyclobutyl;
$R^8$ is H; and
$R^9$ is a triazolyl and optionally substituted with one or more substituents selected from the group consisting of halogen and C$_{1-4}$alkyl.

9. A pharmaceutical composition, which comprises at least one compound of claim 1, and which further comprises at least one pharmaceutically acceptable carrier.

10. A process for the preparation of the pharmaceutical composition of claim 9, comprising combining an effective amount of the compound of formula (I), in intimate admixture with a pharmaceutically acceptable carrier.

11. A method of treating chronic hepatitis B in an individual in need thereof, comprising administering to the individual a therapeutically effective amount of the compound of claim 1.

12. A method of treating an HBV infection or an HBV-induced disease in an individual in need thereof, comprising administering to the individual a therapeutically effective amount of the compound of claim 1.

13. A process for the preparation of a compound of formula (I) according to claim 1, comprising the reaction between a compound of formula (II), wherein formula (II) is and a compound of formula (III),
wherein formula (III) is in the presence of a base, and a coupling reagent,
to form a compound of formula (I), and wherein:
(A) represents a 6-membered aryl ring optionally containing one or more heteroatom(s), the heteroatom or each of the heteroatoms being nitrogen;
$R^1$, $R^2$ and $R^3$ are each independently selected from the group consisting of H, F, Cl, Br, $CHF_2$, $CH_2F$, $CF_3$, CN, $C_{1-4}$alkyl and $C_{3-6}$cycloalkyl;
$R^4$ is selected from the group consisting of H and F;
$R^{5a}$ and $R^{5b}$ are each independently selected from the group consisting of H, $C_{1-4}$alkyl optionally substituted with one or more F, and $C_{3-6}$cycloalkyl optionally substituted with one or more F;
$R^{6a}$ and $R^{6b}$ are each independently selected from the group consisting of H, $C_{1-4}$alkyl optionally substituted with one or more F, and $C_{3-6}$cycloalkyl optionally substituted with one or more F;
$R^{7a}$ and $R^{7b}$ are each independently selected from the group consisting of H, $C_{1-4}$alkyl optionally substituted with one or more F, and $C_{3-6}$cycloalkyl optionally substituted with one or more F;
Q is selected from the group consisting of
  $C_{1-5}$alkyl, optionally substituted with one or more substituents selected from the group consisting of halogen;
  $C_{2-3}$alkenyl substituted with halogen,
  3- to 6-membered monocyclic saturated rings,
  up to 9-membered polycyclic saturated rings,
  wherein the (3- to 6-membered monocyclic or up to 9-membered polycyclic) saturated rings:
    optionally and independently contain one or more heteroatoms, the heteroatoms being independently selected from N, O and S, and/or
    are optionally and independently substituted with one or more substituents selected from the group consisting of F, oxo, OH, C(=O)NHCH₃ and $C_{1-4}$alkyl optionally substituted with one or more F;
$R^8$ is H; and
$R^9$ is selected from the group consisting of
  phenyl,
  phenyl substituted with one or more substituents each independently selected from the group consisting of halogen, CN, $CF_3$, $CF_2H$, $CH_2F$, $C_{1-4}$alkyl, $C_{3-6}$cycloalkyl, OH and $OC_{1-4}$alkyl,
  pyridyl,
  pyridyl substituted with one or more substituents each independently selected from the group consisting of halogen, CN, $CF_3$, $CF_2H$, $CH_2F$, $C_{1-4}$alkyl, $C_{3-6}$cycloalkyl, OH and $OC_{1-4}$alkyl,
  pyrimidyl,
  pyrimidyl substituted with one or more substituents each independently selected from the group consisting of halogen, CN, $CF_3$, $CF_2H$, $CH_2F$, $C_{1-4}$alkyl, $C_{3-6}$cycloalkyl, OH and $OC_{1-4}$alkyl,
  pyrazinyl,
  pyrazinyl substituted with one or more substituents each independently selected from the group consisting of halogen, CN, $CF_3$, $CF_2H$, $CH_2F$, $C_{1-4}$alkyl, $C_{3-6}$cycloalkyl, OH and $OC_{1-4}$alkyl,
  pyridazinyl,
  pyridazinyl substituted with one or more substituents each independently selected from the group consisting of halogen, CN, $CF_3$, $CF_2H$, $CH_2F$, $C_{1-4}$alkyl, $C_{3-6}$cycloalkyl, OH and $OC_{1-4}$alkyl,
  5-membered unsaturated heterocycles containing one to 4 heteroatoms, the heteroatoms being each independently selected from N, O and S, and
  5-membered unsaturated heterocycles containing one to 4 heteroatoms, the heteroatoms being each independently selected from N, O and S, substituted with one or more substituents selected from the group consisting of halogen, CN, $CF_3$, $CF_2H$, $CH_2F$, $C_{1-4}$alkyl, $C_{3-6}$cycloalkyl, OH and $OC_{1-4}$alkyl.

14. The compound of claim 1, wherein the $C_{2-3}$alkenyl is substituted with one or more F.

15. The compound of claim 7, wherein Q is difluorocyclobutyl.

16. The compound of claim 7, wherein Q is 3,3-difluorocyclobutyl.

17. The process of claim 13, wherein the base is DIPEA.

18. The process of claim 13, wherein the coupling agent is HATU.

19. A compound selected from the group consisting of:

-continued
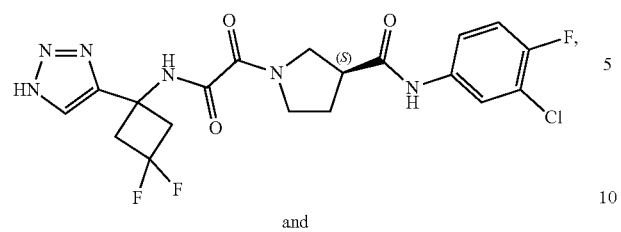
C5
and
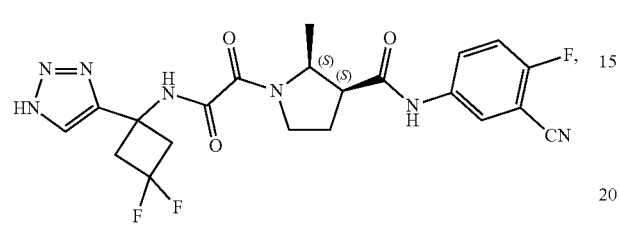
C6
\* \* \* \* \*